(12) United States Patent
Nasu et al.

(10) Patent No.: US 10,510,977 B2
(45) Date of Patent: Dec. 17, 2019

(54) COMPOUND, LIGHT-EMITTING MATERIAL, AND ORGANIC LIGHT-EMITTING DEVICE

(71) Applicants: KYULUX, INC., Fukuoka-shi, Fukuoka (JP); KYUSHU UNIVERSITY, NATIONAL UNIVERSITY CORPORATION, Fukuoka-shi, Fukuoka (JP)

(72) Inventors: Keiro Nasu, Fukuoka (JP); Chihaya Adachi, Fukuoka (JP); Hajime Nakanotani, Fukuoka (JP); YuSeok Yang, Fukuoka (JP); Hiroko Nomura, Fukuoka (JP)

(73) Assignees: KYULUX, INC., Fukuoka (JP); KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 0 days.

(21) Appl. No.: 16/066,718

(22) PCT Filed: Dec. 28, 2016

(86) PCT No.: PCT/JP2016/089034
§ 371 (c)(1),
(2) Date: Jun. 28, 2018

(87) PCT Pub. No.: WO2017/115835
PCT Pub. Date: Jul. 6, 2017

(65) Prior Publication Data
US 2019/0016704 A1 Jan. 17, 2019

(30) Foreign Application Priority Data

Dec. 28, 2015 (JP) .................................. 2015-256571
Apr. 12, 2016 (JP) .................................. 2016-079893

(51) Int. Cl.
*H01L 51/50* (2006.01)
*H01L 51/00* (2006.01)
(Continued)

(52) U.S. Cl.
CPC ........ *H01L 51/5096* (2013.01); *C07D 209/86* (2013.01); *H01L 51/0072* (2013.01);
(Continued)

(58) Field of Classification Search
CPC combination set(s) only.
See application file for complete search history.

(56) References Cited

U.S. PATENT DOCUMENTS

2011/0042664 A1* 2/2011 Katoh .................. H01L 51/004
257/40
2014/0291660 A1* 10/2014 Takaku ................ H01L 51/006
257/40

(Continued)

FOREIGN PATENT DOCUMENTS

JP          5366106 B1      12/2013
KR    10-2015-0061174       8/2015
(Continued)

OTHER PUBLICATIONS

International Preliminary Report on Patentability for corresponding PCT International Application No. PCT/JP2016/089034 dated Jul. 3, 2018 with English translation.
(Continued)

*Primary Examiner* — Mamadou L Diallo
(74) *Attorney, Agent, or Firm* — Browdy and Neimark, PLLC

(57) ABSTRACT

A compound having a structure represented by the following general formula emits delayed fluorescent light, and is useful as a light-emitting material. One or more of $R^1$, $R^2$,
(Continued)

$R^3$, $R^4$, and $R^5$ represent a 9-carbazolyl group having a substituent at at least one of 1-position and 8-position, or a 10-phenoxazyl group or 10-phenothiazyl group having a substituent at at least one of 1-position and 9-position. The balance thereof represents a hydrogen atom or a substituent.

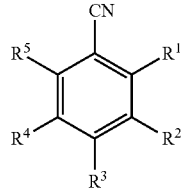

11 Claims, 5 Drawing Sheets

(51) Int. Cl.
  *H01L 51/52* (2006.01)
  *C07D 209/86* (2006.01)
(52) U.S. Cl.
  CPC ...... *H01L 51/5016* (2013.01); *H01L 51/5092* (2013.01); *H01L 51/5206* (2013.01); *H01L 51/5221* (2013.01); *H01L 51/5012* (2013.01); *H01L 51/5056* (2013.01); *H01L 51/5072* (2013.01)

(56) References Cited

U.S. PATENT DOCUMENTS

| 2015/0105564 | A1* | 4/2015 | Adachi | C07D 209/18 548/440 |
| 2017/0062731 | A1* | 3/2017 | Ogiwara | C07D 405/14 |
| 2017/0237016 | A1* | 8/2017 | Haketa | C07D 401/14 257/40 |
| 2018/0170914 | A1* | 6/2018 | Miyata | C07D 405/14 |
| 2019/0013481 | A1* | 1/2019 | Nasu | C07D 209/86 |

FOREIGN PATENT DOCUMENTS

| WO | 2014/146752 A1 | 9/2014 |
| WO | 2015/022987 A1 | 2/2015 |
| WO | 2015/087795 A1 | 6/2015 |
| WO | 2016/086885 A1 | 6/2016 |

OTHER PUBLICATIONS

International Search Report for corresponding PCT International Application No. PCT/JP2016/089034.

* cited by examiner

COMPOUND, LIGHT-EMITTING MATERIAL, AND ORGANIC LIGHT-EMITTING DEVICE

TECHNICAL FIELD

The present invention relates to a compound that is useful as a light-emitting material, and an organic light-emitting device using the same.

BACKGROUND ART

An organic light-emitting device, such as an organic electroluminescent device (organic EL device), has been actively studied for enhancing the light emission efficiency thereof. In particular, various studies for enhancing the light emission efficiency have been made by newly developing and combining an electron transporting material, a hole transporting material, a light-emitting material, and the like constituting an organic electroluminescent device. There are studies focusing on a compound emitting delayed fluorescent light.

Delayed fluorescent light is fluorescent light emitted through such a mechanism that a compound in an excited state through application of energy undergoes reverse intersystem crossing from the excited triplet state to the excited singlet state, and then the excited singlet state returns to the ground state to emit the fluorescent light, and the delayed fluorescent light is fluorescent light that is observed with a delay from the fluorescent light directly emitted from the excited singlet state (normal fluorescent light). With the use of the compound capable of emitting delayed fluorescent light as a light-emitting material of an organic electroluminescent device, the energy of the excited triplet state, which has a large formation probability, can be converted to fluorescent light and thus can be effectively utilized for light emission, from which a high light emission efficiency can be expected. Accordingly, compounds emitting delayed fluorescent light have been actively developed, and there have been some proposals of the utilization of the compound as a light-emitting material.

For example, PTL 1 describes that a compound having a benzene ring having substituted thereon two cyano groups and one or more carbazolyl group or the like is a compound capable of emitting delayed fluorescent light. The literature describes that the use of the compound as a light-emitting material of an organic electroluminescent device and the like can enhance the light emission efficiency.

CITATION LIST

Patent Literature

PTL 1: Japanese Patent No. 5,366,106

SUMMARY OF INVENTION

Technical Problem

However, it is still unclear as to what type of chemical structure can generally emit delayed fluorescent light. For example, compounds that are similar to the compound described in PTL 1 do not necessarily emit delayed fluorescent light, and it is difficult to estimate from the structure as to whether or not delayed fluorescent light is emitted therefrom. Accordingly, for employing compounds capable of emitting delayed fluorescent light from a wider range of compounds, it is considered that a compound capable of emitting delayed fluorescent light is necessarily discovered and utilized from outside the range of the compounds proposed by PTL 1.

Under the circumstances, the present inventors have made earnest investigations for discovering a compound emitting delayed fluorescent light even though having a structure that is not described in PTL 1. The inventors have made earnest investigations for eliciting the general formula of the compound and generalizing the structure of an organic light-emitting device having a high light emission efficiency.

Solution to Problem

As a result of the earnest investigations, the inventors have found that a compound capable of emitting delayed fluorescent light exists in compounds having a structure containing a benzene ring having only one cyano group substituted thereon. The inventors have reached knowledge that the use of the compound capable of emitting delayed fluorescent light as a light-emitting material can provide an organic light-emitting device having a high light emission efficiency. The invention is proposed based on the knowledge and specifically has the following constitution.

[1] A compound having a structure represented by the following general formula (1):

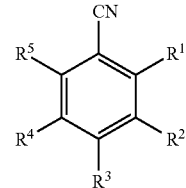

General Formula (1)

wherein in the general formula (1), one or more of $R^1$, $R^2$, $R^3$, $R^4$, and $R^5$ each independently represent a 9-carbazolyl group having a substituent at at least one of 1-position and 8-position, a 10-phenoxazyl group having a substituent at at least one of 1-position and 9-position or a 10-phenothiazyl group having a substituent at at least one of 1-position and 9-position. The balance thereof represents a hydrogen atom or a substituent, provided that the substituent excludes a 9-carbazolyl group having a substituent at at least one of 1-position and 8-position, a 10-phenoxazyl group having a substituent at at least one of i-position and 9-position or a 10-phenothiazyl group having a substituent at at least one of 1-position and 9-position. One or more of carbon atoms constituting ring skeletons of the 9-carbazolyl group, the 10-phenoxazyl group, and the 10-phenothiazyl group may be replaced by a nitrogen atom.

[2] The compound according to the item [1], wherein the substituent represents a substituted or unsubstituted alkyl group, a substituted or unsubstituted alkoxy group, a substituted or unsubstituted thioalkoxy group, a substituted or unsubstituted aryl group, a substituted or unsubstituted heteroaryl group, a substituted or unsubstituted aryloxy group, a substituted or unsubstituted heteroaryloxy group, a substituted or unsubstituted thioaryloxy group, a substituted or unsubstituted thioheteroaryloxy group, a secondary amino group, a tertiary amino group, or a substituted or unsubstituted silyl group.

[3] The compound according to the item [1] or [2], wherein one to three of $R^1$, $R^2$, $R^3$, $R^4$, and $R^5$ each independently represent a 9-carbazolyl group having a substituent at at least one of 1-position and 8-position, a 10-phenoxazyl group having a substituent at at least one of 1-position and 9-position or a 10-phenothiazyl group having a substituent at at least one of 1-position and 9-position, at least one of the balance thereof each independently represents a 9-carbazolyl group unsubstituted at the 1-position and the 8-position, a 10-phenoxazyl group unsubstituted at the 1-position and the 9-position or a 10-phenothiazyl group unsubstituted at the 1-position and the 9-position, and one or more of carbon atoms constituting ring skeletons of the 9-carbazolyl group, the 10-phenoxazyl group, and the 10-phenothiazyl group may be replaced by a nitrogen atom.

[4] The compound according to any one of the items [1] to [3], wherein two to four of $R^1$, $R^2$, $R^3$, $R^4$, and $R^5$ each independently represent a substituted or unsubstituted 9-carbazolyl group, a substituted or unsubstituted 10-phenoxazyl group or a substituted or unsubstituted 10-phenothiazyl group.

[5] The compound according to any one of the items [1] to [4], wherein $R^1$, $R^3$, and $R^5$ each independently represent a substituted or unsubstituted 9-carbazolyl group, a substituted or unsubstituted 10-phenoxazyl group or a substituted or unsubstituted 10-phenothiazyl group.

[6] The compound according to the item [5], wherein $R^3$ represents a 9-carbazolyl group having a substituent at at least one of 1-position and 8-position, a 10-phenoxazyl group having a substituent at at least one of 1-position and 9-position or a 10-phenothiazyl group having a substituent at at least one of 1-position and 9-position.

[7] The compound according to the item [6], wherein $R^1$ and $R^5$ each independently represent a 9-carbazolyl group unsubstituted at the 1-position and the 8-position, a 10-phenoxazyl group unsubstituted at the 1-position and the 9-position or a 10-phenothiazyl group unsubstituted at the 1-position and the 9-position.

[8] The compound according to any one of the items [1] to [4], wherein $R^2$ and $R^4$ each independently represent a substituted or unsubstituted 9-carbazolyl group, a substituted or unsubstituted 10-phenoxazyl group or a substituted or unsubstituted 10-phenothiazyl group.

[9] The compound according to the item [8], wherein $R^2$ and $R^4$ each independently represent a 9-carbazolyl group having a substituent at at least one of 1-position and 8-position, a 10-phenoxazyl group having a substituent at at least one of 1-position and 9-position or a 10-phenothiazyl group having a substituent at at least one of 1-position and 9-position.

[10] A light-emitting material containing the compound according to any one of the items [1] to [9].

[11] The light-emitting material according to the item [10], wherein the light-emitting material emits delayed fluorescent light.

[12] An organic light-emitting device containing a substrate having thereon a light-emitting layer containing the light-emitting material according to the item [10] or [11].

[13] The organic light-emitting device according to the item [12], wherein the organic light-emitting device is an organic electroluminescent device.

[14] The organic light-emitting device according to the item [12] or [13], wherein the light-emitting layer contains the compound according to any one of the items [1] to [9] and a host material.

[15] A delayed fluorescent material having a structure represented by the general formula (1).

Advantageous Effects of Invention

The compound of the invention is useful as a light-emitting material. The compound of the invention can emit delayed fluorescent light, and the triplet excitation energy thereof can be effectively utilized for light emission. Accordingly, the organic light-emitting device using the compound of the invention as a light-emitting material can achieve a high light emission efficiency.

DESCRIPTION OF EMBODIMENTS

Figure 1:
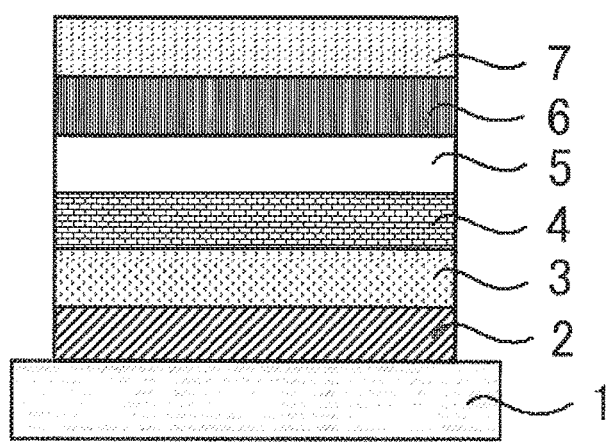
FIG. 1 is a schematic cross sectional view showing an example of a layer structure of an organic electroluminescent device.

The contents of the invention will be described in detail below. The constitutional elements may be described below with reference to representative embodiments and specific examples of the invention, but the invention is not limited to the embodiments and the examples. In the description herein, a numerical range expressed as "to" means a range that includes the upper limit and/or the lower limit. In the invention, the hydrogen atom that is present in the compound used in the invention is not particularly limited in isotope species, and for example, all the hydrogen atoms in the molecule may be $^1H$, and all or a part of them may be $^2H$ (deuterium (D)).

Compound Represented by General Formula (1)

The light-emitting material of the invention contains a compound having a structure represented by the following general formula (1).

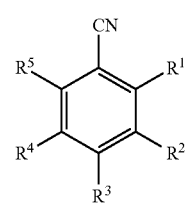

General Formula (1)

In the general formula (1), one or more of $R^1$, $R^2$, $R^3$, $R^4$, and $R^5$ each independently represent a 9-carbazolyl group having a substituent at at least one of 1-position and 8-position, a 10-phenoxazyl group having a substituent at at least one of 1-position and 9-position or a 10-phenothiazyl group having a substituent at at least one of i-position and 9-position.

The 9-carbazolyl group having a substituent at at least one of 1-position and 8-position, the 10-phenoxazyl group having a substituent at at least one of 1-position and 9-position or the 10-phenothiazyl group having a substituent at at least one of 1-position and 9-position (hereinafter, the groups may be collectively referred to as "9-carbazolyl group and the like having a substituent at a specific position") may be only one or two or more of $R^1$, $R^2$, $R^3$, $R^4$, and $R^5$.

In the case where only one of $R^1$, $R^2$, $R^3$, $R^4$, and $R^5$ is the 9-carbazolyl group and the like having a substituent at a specific position, any one of $R^2$, $R^3$, and $R^4$ is preferably the 9-carbazolyl group and the like having a substituent at a specific position, and more preferably, $R^3$ is the 9-carbazolyl group and the like having a substituent at a specific position. In the case where two of $R^1$, $R^2$, $R^3$, $R^4$, and $R^5$ are the 9-carbazolyl group and the like having a substituent at a specific position, $R^1$ and $R^5$ or $R^2$ and $R^4$ are preferably the 9-carbazolyl group and the like having a substituent at a specific position, and more preferably, $R^2$ and $R^4$ are the 9-carbazolyl group and the like having a substituent at a specific position. In the case where three of $R^1$, $R^2$, $R^3$, $R^4$, and $R^5$ are the 9-carbazolyl group and the like having a substituent at a specific position, $R^2$, $R^3$ and $R^4$ are preferably the 9-carbazolyl group and the like having a substituent at a specific position. In the case where four of $R^1$, $R^2$, $R^1$, $R^4$, and $R^5$ are the 9-carbazolyl group and the like having a substituent at a specific position, $R^1$, $R^2$, $R^4$ and $R^5$ are preferably the 9-carbazolyl group and the like having a substituent at a specific position. The preferred compound is a compound in which $R^3$ in the general formula (1) is the 9-carbazolyl group and the like having a substituent at a specific position and a compound in which $R^2$ and $R^4$ in the general formula (1) are the 9-carbazolyl group and the like having a substituent at a specific position. When there is a plurality of the 9-carbazolyl group and the like having a substituent at a specific position in the general formula (1), they may be the same or different from each other but are preferably the same. Also, in the compound represented by the general formula (1), $R^1$ and $R^5$, and $R^2$ and $R^4$ are preferably the same, respectively.

In the 9-carbazolyl group having a substituent at at least one of 1-position and 8-position, the position having a substituent may be only the 1-position, only the 8-position or both the 1-position and the 8-position but is preferably both the 1-position and the 8-position. When the 9-carbazolyl group has substituents at both the 1-position and the 8-position, the substituents may be the same or different from each other but are preferably the same. The positions of the 9-carbazolyl group except the 1-position and the 8-position may have substituents or may be unsubstituted. In the case where the 9-carbazolyl group has a substituent, the substitution position is preferably at least one of the 3-position and the 6-position. That is, the substitution positions of only the 3-position, only the 6-position or both the 3-position and the 6-position are all preferable.

In the 10-phenoxazyl group having a substituent at at least one of 1-position and 9-position, the position having a substituent may be only the 1-position, only the 9-position or both the 1-position and the 9-position but is preferably both the 1-position and the 9-position. When the 10-phenoxazyl group has substituents at both the 1-position and the 9-position, the substituents may be the same or different from each other but are preferably the same. The positions of the 10-phenoxazyl group except the 1-position and the 9-position may have substituents or may be unsubstituted. In the case where the 10-phenoxazyl group has a substituent, the substitution position is preferably at least one of the 3-position and the 7-position. That is, the substitution positions of only the 3-position, only the 7-position or both the 3-position and the 7-position are all preferable.

In the 10-phenothiazyl group having a substituent at at least one of 1-position and 9-position, the position having a substituent may be only the 1-position, only the 9-position or both the 1-position and the 9-position but is preferably both the 1-position and the 9-position. When the 10-phenothiazyl group has substituents at both the 1-position and the 9-position, the substituents may be the same or different from each other but are preferably the same. The positions of the 10-phenothiazyl group except the 1-position and the 9-position may have substituents or may be unsubstituted. In the case where the 10-phenothiazyl group has a substituent, the substitution position is preferably at least one of the 3-position and the 7-position. That is, the substitution positions of only the 3-position, only the 7-position or both the 3-position and the 7-position are all preferable.

Of the 9-carbazolyl group and the like having a substituent at a specific position, the 9-carbazolyl group having a substituent at at least one of 1-position and 8-position is preferable, the 9-carbazolyl group having substituents both at the 1-position and the 8-position is more preferable, and the 9-carbazolyl group having substituents both at the 1-position and the 8-position and both at the 3-position and the 6-position is further preferable.

As the substituent that can be substituted for the 9-carbazolyl group having a substituent at at least one of 1-position and 8-position, the 10-phenoxazyl group having a substituent at at least one of 1-position and 9-position or the 10-phenothiazyl group having a substituent at at least one of 1-position and 9-position, a hydroxy group, a halogen atom, a cyano group, an alkyl group, an alkoxy group, a thioalkoxy group, a secondary amino group, a tertiary amino group, an acyl group, an aryl group, a heteroaryl group, an aryloxy group, a heteroaryloxy group, a thioaryloxy group, a thioheteroaryloxy group, an alkenyl group, an alkynyl group, an alkoxycarbonyl group, an alkylsulfonyl group, a haloalkyl group, an amid group, an alkylamide group, a silyl group, a trialkylsilylalkyl group, a trialkylsilylalkenyl group, a trialkylsilylalkynyl group, a nitro group and the like may be exemplified. In these specific examples, the substituent that is capable of being further substituted with a substituent may be substituted. The preferred substituent is a substituted or unsubstituted alkyl group, a substituted or unsubstituted alkoxy group, a substituted or unsubstituted thioalkoxy group, a substituted or unsubstituted aryl group, a substituted or unsubstituted heteroaryl group, a substituted or unsubstituted aryloxy group, a substituted or unsubstituted heteroaryloxy group, a substituted or unsubstituted thioaryloxy group, a substituted or unsubstituted thioheteroaryloxy group, a secondary amino group, a tertiary amino group or a substituted or unsubstituted silyl group. The more preferred substitute is a substituted or unsubstituted alkyl group, a substituted or unsubstituted alkoxy group, a substituted or unsubstituted aryl group, and a substituted or unsubstituted heteroaryl group. The particularly preferred substitute is a substituted or unsubstituted alkyl group. The carbon number of the substitutes is 1 to 20, more preferably 1 to 10, and further preferably 1 to 5 in the substituted or unsubstituted alkyl group, is 1 to 20 in the substituted or unsubstituted alkoxy group and the substituted or unsubstituted thioalkoxy group, is 6 to 40 in the substituted or unsubstituted aryl group, the substituted or unsubstituted aryloxy group and the substituted or unsubstituted thioaryloxy group, is 3 to 40 in the substituted or unsubstituted heteroaryl group, the substituted or unsubstituted heteroaryloxy group and the substituted or unsubstituted thioheteroaryloxy group, is 1 to 20 in the secondary amino group and the tertiary amino group, and is 3 to 20 in the silyl group substituted with an alkyl group. Here, in the case where each substituent is further substituted with a substituent (for example, in the case of the substituted alkyl group and the like), the carbon number means a summed carbon number of the carbon number of a substituted substituent and the carbon number of a substituent substituted for the substituent.

In the case where one to four of $R^1$, $R^2$, $R^3$, $R^4$, and $R^5$ in the general formula (1) each independently represent a 9-carbazolyl group having a substituent at at least one of 1-position and 8-position, a 10-phenoxazyl group having a substituent at at least one of 1-position and 9-position or a 10-phenothiazyl group having a substituent at at least one of 1-position and 9-position, the balance thereof represents a hydrogen atom or a substituent, provided that the substituent excludes a 9-carbazolyl group having a substituent at at least one of 1-position and 8-position, a 10-phenoxazyl group having a substituent at at least one of 1-position and 9-position or a 10-phenothiazyl group having a substituent at at least one of 1-position and 9-position. For the preferred range of the substituent, reference may be made to the preferred range of the substituent that can be substituted for the 9-carbazolyl group having a substituent at at least one of 1-position and 8-position, and the like. However, the "substituted or unsubstituted heteroaryl group" does not include a 9-carbazolyl group having a substituent at at least one of 1-position and 8-position, a 10-phenoxazyl group having a substituent at at least one of 1-position and 9-position or a 10-phenothiazyl group having a substituent at at least one of 1-position and 9-position.

In the case where one to three of $R^1$, $R^2$, $R^3$, $R^4$, and $R^5$ each independently represent a 9-carbazolyl group having a substituent at at least one of 1-position and 8-position, a 10-phenoxazyl group having a substituent at at least one of 1-position and 9-position or a 10-phenothiazyl group having a substituent at at least one of 1-position and 9-position (the 9-carbazolyl group and the like having a substituent at a specific position), at least one of the balance thereof each independently is preferably a 9-carbazolyl group of which the 1-position and the 8-position are not substituted, a 10-phenoxazyl group of which the 1-position and the 9-position are not substituted or a 10-phenothiazyl group of which the 1-position and the 9-position are not substituted (hereinafter, the groups may be collectively referred to as "9-carbazolyl group and the like of which specific positions are not substituted"). Also, a substitute except the cyano group is preferably selected. Particularly, in the case where one of $R^1$, $R^2$, $R^3$, $R^4$, and $R^5$ represent the 9-carbazolyl group and the like having a substituent at a specific position, at least two of the remaining four are preferably the 9-carbazolyl group and the like of which specific positions are not substituted. Among of them, more preferably, $R^3$ is the 9-carbazolyl group and the like having a substituent at a specific position and $R^1$ and $R^5$ are the 9-carbazolyl group and the like of which specific positions are not substituted. In the meantime, in the case where two or three of $R^1$, $R^2$, $R^3$, $R^4$, and $R^5$ are the 9-carbazolyl group and the like having a substituent at a specific position, at least one of the balance thereof is preferably the 9-carbazolyl group and the like of which specific positions are not substituted. However, all of the balance is also preferably a hydrogen atom.

In the 9-carbazolyl group of which the 1-position and the 8-position are not substituted, the positions except the 1-position and the 8-position may have substituents or may be unsubstituted. In the case where the 9-carbazolyl group has a substituent, the substitution position is preferably at least one of the 3-position and the 6-position. In the 10-phenoxazyl group of which the 1-position and the 9-position are not substituted and the 10-phenothiazyl group of which the 1-position and the 9-position are not substituted, the positions except the 1-position and the 9-position may have substituents or may be unsubstituted. In the case where the 10-phenoxazyl group and the 10-phenothiazyl group have a substituent, the substitution position is preferably at least one of the 3-position and the 7-position. For the preferred ranges of the substituent that can be substituted for the 9-carbazolyl group and the like of which specific positions are not substituted, reference may be made to the preferred ranges of the substituent that can be substituted for the 9-carbazolyl group having a substituent at at least one of 1-position and 8-position, and the like.

Of the 9-carbazolyl group and the like of which specific positions are not substituted, a 9-carbazolyl group of which the 1-position and the 8-position are not substituted is preferable, and a 9-carbazolyl group of which all of the 1-position to the 8-position are not substituted is more preferable.

The compound represented by the general formula (1) of the present invention is preferably a compound in which two to four of $R^1$, $R^2$, $R^3$, $R^4$, and $R^5$ each independently represent a substituted or unsubstituted 9-carbazolyl group, a substituted or unsubstituted 10-phenoxazyl group or a substituted or unsubstituted 10-phenothiazyl group, and is more preferably a compound in which $R^1$, $R^3$, and $R^5$ each independently represent a substituted or unsubstituted 9-carbazolyl group, a substituted or unsubstituted 10-phenoxazyl group or a substituted or unsubstituted 10-phenothiazyl group, and is further preferably a compound in which $R^2$ and $R^4$ each independently represent a substituted or unsubstituted 9-carbazolyl group, a substituted or unsubstituted 10-phenoxazyl group or a substituted or unsubstituted 10-phenothiazyl group. In the case where the 9-carbazolyl group, the 10-phenoxazyl group or the 10-phenothiazyl group has a plurality of substitutes, the substitutes may be the same or different from each other.

Also, one or more of carbon atoms constituting ring skeletons of the 9-carbazolyl group, the 10-phenoxazyl group or the 10-phenothiazyl group in each of $R^1$, $R^2$, $R^3$, $R^4$, and $R^5$ may be replaced by a nitrogen atom. The number of carbon atoms that are replaced by a nitrogen atom is not particularly limited, and is preferably from 1 to 4, and more preferably 1 or 2.

In the below, specific examples of "9-carbazolyl group having a substituent at at least one of 1-position and 8-position" represented by one or more of $R^1$, $R^2$, $R^3$, $R^4$, and $R^5$ in the general formula (1), specific examples of "substitute" represented by the balance except one or more of $R^1$, $R^2$, $R^3$, $R^4$, and $R^5$, and specific examples of a compound represented by the general formula (1) are exemplified. In the present invention, "9-carbazolyl group having a substituent at at least one of 1-position and 8-position" represented by one or more of $R^1$, $R^2$, $R^3$, $R^4$, and $R^5$ in the general formula (1), "substitute" represented by the balance except one or more of $R^1$, $R^2$, $R^3$, $R^4$, and $R^5$, and a compound represented by the general formula (1) are not construed as being limited to the specific examples.

First, the specific examples (m-D1 to m-D9) of "9-carbazolyl group having a substituent at at least one of 1-position and 8-position" represented by one or more of $R^1$, $R^2$, $R^3$, $R^4$, and $R^5$ in the general formula (1) are enumerated.

The specific examples (Cz, Cz1 to Cz11) of "substitute" represented by the balance except the "one or more" of $R^1$, $R^2$, $R^3$, $R^4$, and $R^5$ in the general formula (1) are enumerated.

Cz6
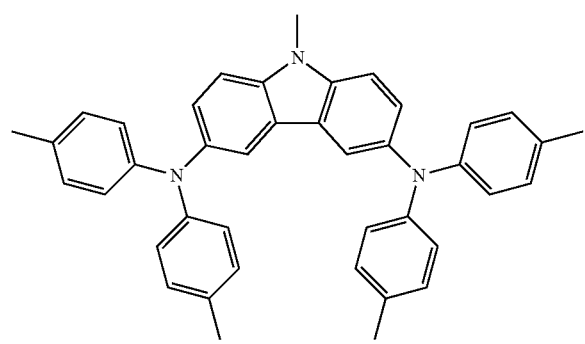
Cz12
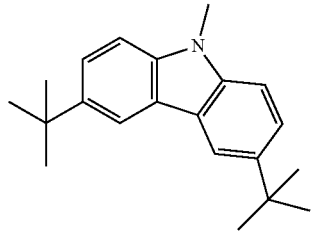
The specific examples of a compound represented by the general formula (1) are enumerated.
Cz7
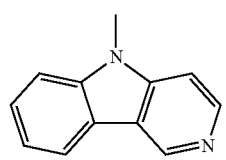
Cz8
Compound 291
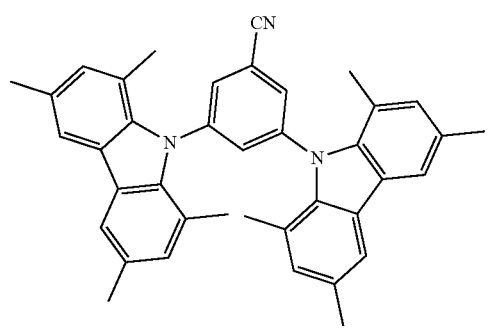
Cz9
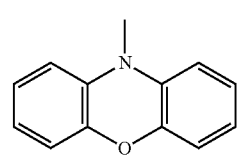
Compound 241
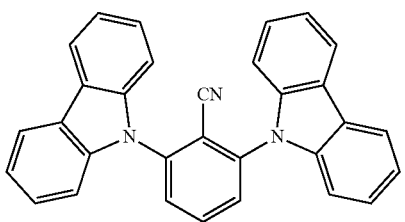
Cz10
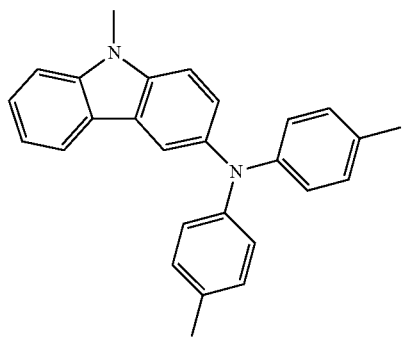
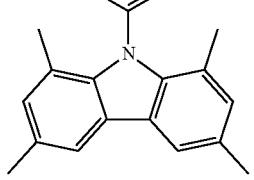
Compound 135
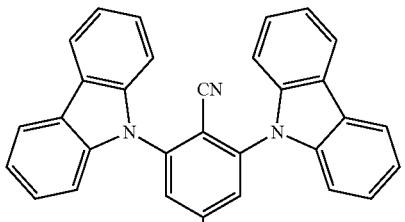
Cz11
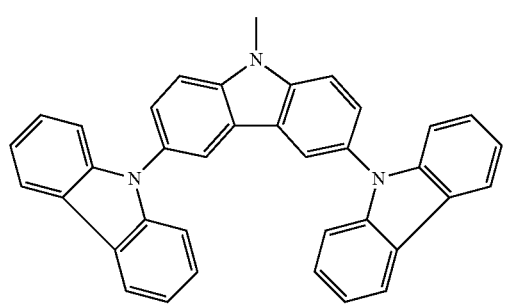
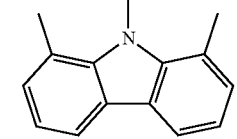
The specific examples including the three compound examples are shown in below Tables.

TABLE 1-1

| No | R¹ | R² | R³ | R⁴ | R⁵ |
|---|---|---|---|---|---|
| 1 | m-D1 | Cz | Cz | Cz | Cz |
| 2 | Cz | m-D1 | Cz | Cz | Cz |
| 3 | Cz | Cz | m-D1 | Cz | Cz |
| 4 | m-D1 | Cz | Cz | Cz | H |
| 5 | Cz | m-D1 | Cz | Cz | H |
| 6 | Cz | Cz | m-D1 | Cz | H |
| 7 | Cz | Cz | Cz | m-D1 | H |
| 8 | m-D1 | Cz | Cz | H | Cz |
| 9 | Cz | m-D1 | Cz | H | Cz |
| 10 | Cz | Cz | m-D1 | H | Cz |
| 11 | Cz | Cz | Cz | H | m-D1 |
| 12 | m-D1 | Cz | H | Cz | Cz |
| 13 | Cz | m-D1 | H | Cz | Cz |
| 14 | m-D1 | Cz | Cz | H | H |
| 15 | Cz | m-D1 | Cz | H | H |
| 16 | Cz | Cz | m-D1 | H | H |
| 17 | m-D1 | Cz | H | Cz | H |
| 18 | Cz | m-D1 | H | Cz | H |
| 19 | Cz | Cz | H | m-D1 | H |
| 20 | m-D1 | H | Cz | Cz | H |
| 21 | Cz | H | m-D1 | Cz | H |
| 22 | Cz | H | Cz | m-D1 | H |
| 23 | H | m-D1 | Cz | Cz | H |
| 24 | H | Cz | m-D1 | Cz | H |
| 25 | m-D1 | Cz | H | H | Cz |
| 26 | Cz | m-D1 | H | H | Cz |
| 27 | Cz | Cz | H | H | m-D1 |
| 28 | m-D1 | H | Cz | H | Cz |
| 29 | Cz | H | m-D1 | H | Cz |
| 30 | m-D1 | Cz | H | H | H |
| 31 | Cz | m-D1 | H | H | H |
| 32 | m-D1 | H | Cz | H | H |
| 33 | Cz | H | m-D1 | H | H |
| 34 | H | m-D1 | Cz | H | H |
| 35 | H | Cz | m-D1 | H | H |
| 36 | m-D1 | H | H | Cz | H |
| 37 | Cz | H | H | m-D1 | H |
| 38 | H | m-D1 | H | Cz | H |
| 39 | m-D1 | H | H | H | Cz |
| 40 | m-D1 | H | H | H | H |
| 41 | H | m-D1 | H | H | H |
| 42 | H | H | m-D1 | H | H |
| 43 | m-D1 | m-D1 | Cz | Cz | H |
| 44 | m-D1 | Cz | m-D1 | Cz | H |
| 45 | m-D1 | Cz | Cz | m-D1 | H |
| 46 | Cz | m-D1 | m-D1 | Cz | H |
| 47 | Cz | m-D1 | Cz | m-D1 | H |
| 48 | Cz | Cz | m-D1 | m-D1 | H |
| 49 | m-D1 | m-D1 | Cz | H | Cz |
| 50 | m-D1 | Cz | m-D1 | H | Cz |
| 51 | m-D1 | Cz | Cz | H | m-D1 |
| 52 | Cz | m-D1 | m-D1 | H | Cz |
| 53 | Cz | m-D1 | Cz | H | m-D1 |
| 54 | Cz | Cz | m-D1 | H | m-D1 |
| 55 | m-D1 | m-D1 | H | Cz | Cz |
| 56 | m-D1 | Cz | H | m-D1 | Cz |
| 57 | m-D1 | Cz | H | Cz | m-D1 |
| 58 | Cz | m-D1 | H | m-D1 | Cz |

TABLE 1-2

| No | R¹ | R² | R³ | R⁴ | R⁵ |
|---|---|---|---|---|---|
| 59 | m-D1 | m-D1 | Cz | H | H |
| 60 | m-D1 | Cz | m-D1 | H | H |
| 61 | Cz | m-D1 | m-D1 | H | H |
| 62 | m-D1 | m-D1 | H | Cz | H |
| 63 | m-D1 | m-D1 | H | m-D1 | H |
| 64 | Cz | m-D1 | H | m-D1 | H |
| 65 | m-D1 | H | m-D1 | Cz | H |
| 66 | m-D1 | H | Cz | m-D1 | H |
| 67 | Cz | H | m-D1 | m-D1 | H |
| 68 | H | m-D1 | m-D1 | Cz | H |
| 69 | H | m-D1 | Cz | m-D1 | H |
| 70 | m-D1 | m-D1 | H | H | Cz |
| 71 | m-D1 | Cz | H | H | m-D1 |
| 72 | Cz | m-D1 | H | H | m-D1 |
| 73 | m-D1 | H | m-D1 | H | Cz |
| 74 | m-D1 | H | Cz | H | m-D1 |
| 75 | m-D1 | m-D1 | H | H | H |
| 76 | m-D1 | H | m-D1 | H | H |
| 77 | H | m-D1 | m-D1 | H | H |
| 78 | m-D1 | H | H | m-D1 | H |
| 79 | H | m-D1 | H | m-D1 | H |
| 80 | m-D1 | H | H | H | m-D1 |
| 81 | m-D1 | m-D1 | m-D1 | Cz | Cz |
| 82 | m-D1 | m-D1 | Cz | m-D1 | Cz |
| 83 | m-D1 | m-D1 | Cz | Cz | m-D1 |
| 84 | m-D1 | Cz | m-D1 | m-D1 | Cz |
| 85 | m-D1 | Cz | m-D1 | Cz | m-D1 |
| 86 | m-D1 | m-D1 | m-D1 | Cz | H |
| 87 | m-D1 | m-D1 | Cz | m-D1 | H |
| 88 | m-D1 | Cz | m-D1 | Cz | H |
| 89 | Cz | m-D1 | m-D1 | m-D1 | H |
| 90 | m-D1 | m-D1 | m-D1 | H | Cz |
| 91 | m-D1 | m-D1 | Cz | H | m-D1 |
| 92 | m-D1 | Cz | m-D1 | H | m-D1 |
| 93 | Cz | m-D1 | m-D1 | H | m-D1 |
| 94 | m-D1 | m-D1 | H | m-D1 | Cz |
| 95 | m-D1 | m-D1 | H | Cz | m-D1 |
| 96 | m-D1 | m-D1 | m-D1 | H | H |
| 97 | m-D1 | m-D1 | H | m-D1 | H |
| 98 | m-D1 | H | m-D1 | m-D1 | H |
| 99 | H | m-D1 | m-D1 | m-D1 | H |
| 100 | m-D1 | m-D1 | m-D1 | m-D1 | Cz |
| 101 | m-D1 | m-D1 | m-D1 | Cz | m-D1 |
| 102 | m-D1 | m-D1 | Cz | m-D1 | m-D1 |
| 103 | m-D1 | m-D1 | m-D1 | m-D1 | H |
| 104 | m-D1 | m-D1 | m-D1 | H | m-D1 |
| 105 | m-D1 | m-D1 | H | m-D1 | m-D1 |
| 106 | m-D1 | H | m-D1 | m-D1 | m-D1 |
| 107 | m-D2 | Cz | Cz | Cz | Cz |
| 108 | Cz | m-D2 | Cz | Cz | Cz |
| 109 | Cz | Cz | m-D2 | Cz | Cz |
| 110 | m-D2 | Cz | Cz | Cz | H |
| 111 | Cz | m-D2 | Cz | Cz | H |
| 112 | Cz | Cz | m-D2 | Cz | H |
| 113 | Cz | Cz | Cz | m-D2 | H |
| 114 | m-D2 | Cz | Cz | H | Cz |
| 115 | Cz | m-D2 | Cz | H | Cz |
| 116 | Cz | Cz | m-D2 | H | Cz |
| 117 | Cz | Cz | Cz | H | m-D2 |

TABLE 1-3

| No | R¹ | R² | R³ | R⁴ | R⁵ |
|---|---|---|---|---|---|
| 118 | m-D2 | Cz | H | Cz | Cz |
| 119 | Cz | m-D2 | H | Cz | Cz |
| 120 | m-D2 | Cz | Cz | H | H |
| 121 | Cz | m-D2 | Cz | H | H |
| 122 | Cz | Cz | m-D2 | H | H |
| 123 | m-D2 | Cz | H | Cz | H |
| 124 | Cz | m-D2 | H | Cz | H |
| 125 | Cz | Cz | H | m-D2 | H |
| 126 | m-D2 | H | Cz | Cz | H |
| 127 | Cz | H | m-D2 | Cz | H |
| 128 | Cz | H | Cz | m-D2 | H |
| 129 | H | m-D2 | Cz | Cz | H |
| 130 | H | Cz | m-D2 | Cz | H |
| 131 | m-D2 | Cz | H | H | Cz |
| 132 | Cz | m-D2 | H | H | Cz |
| 133 | Cz | Cz | H | H | m-D2 |
| 134 | m-D2 | H | Cz | H | Cz |
| 135 | Cz | H | m-D2 | H | Cz |
| 136 | m-D2 | Cz | H | H | H |
| 137 | Cz | m-D2 | H | H | H |
| 138 | m-D2 | H | Cz | H | H |
| 139 | Cz | H | m-D2 | H | H |
| 140 | H | m-D2 | Cz | H | H |
| 141 | H | Cz | m-D2 | H | H |
| 142 | m-D2 | H | H | Cz | H |
| 143 | Cz | H | H | m-D2 | H |
| 144 | H | m-D2 | H | Cz | H |
| 145 | m-D2 | H | H | H | Cz |
| 146 | m-D2 | H | H | H | H |

TABLE 1-3-continued

| | | | | | |
|---|---|---|---|---|---|
| 147 | H | m-D2 | H | H | H |
| 148 | H | H | m-D2 | H | H |
| 149 | m-D2 | m-D2 | Cz | Cz | H |
| 150 | m-D2 | Cz | m-D2 | Cz | H |
| 151 | m-D2 | Cz | Cz | m-D2 | H |
| 152 | Cz | m-D2 | m-D2 | Cz | H |
| 153 | Cz | m-D2 | Cz | m-D2 | H |
| 154 | Cz | Cz | m-D2 | m-D2 | H |
| 155 | m-D2 | m-D2 | Cz | H | Cz |
| 156 | m-D2 | Cz | m-D2 | H | Cz |
| 157 | m-D2 | Cz | Cz | H | m-D2 |
| 158 | Cz | m-D2 | m-D2 | H | Cz |
| 159 | Cz | m-D2 | Cz | H | m-D2 |
| 160 | Cz | Cz | m-D2 | H | m-D2 |
| 161 | m-D2 | m-D2 | H | Cz | Cz |
| 162 | m-D2 | Cz | H | m-D2 | Cz |
| 163 | m-D2 | Cz | H | Cz | m-D2 |
| 164 | Cz | m-D2 | H | m-D2 | Cz |
| 165 | m-D2 | m-D2 | Cz | H | H |
| 166 | m-D2 | Cz | m-D2 | H | H |
| 167 | Cz | m-D2 | m-D2 | H | H |
| 168 | m-D2 | m-D2 | H | Cz | H |
| 169 | m-D2 | Cz | H | m-D2 | H |
| 170 | Cz | m-D2 | H | m-D2 | H |
| 171 | m-D2 | H | m-D2 | Cz | H |
| 172 | m-D2 | H | Cz | m-D2 | H |
| 173 | Cz | H | m-D2 | m-D2 | H |
| 174 | H | m-D2 | m-D2 | Cz | H |
| 175 | H | m-D2 | Cz | m-D2 | H |
| 176 | m-D2 | m-D2 | H | H | Cz |

TABLE 1-4

| | | | | | |
|---|---|---|---|---|---|
| 177 | m-D2 | Cz | H | H | m-D2 |
| 178 | Cz | m-D2 | H | H | m-D2 |
| 179 | m-D2 | H | m-D2 | H | Cz |
| 180 | m-D2 | H | Cz | H | m-D2 |
| 181 | m-D2 | m-D2 | H | H | H |
| 182 | m-D2 | H | m-D2 | H | H |
| 183 | H | m-D2 | m-D2 | H | H |
| 184 | m-D2 | H | H | m-D2 | H |
| 185 | H | m-D2 | H | m-D2 | H |
| 186 | m-D2 | H | H | H | m-D2 |
| 187 | m-D2 | m-D2 | m-D2 | Cz | Cz |
| 188 | m-D2 | m-D2 | Cz | m-D2 | Cz |
| 189 | m-D2 | m-D2 | Cz | Cz | m-D2 |
| 190 | m-D2 | Cz | m-D2 | m-D2 | Cz |
| 191 | m-D2 | Cz | m-D2 | Cz | m-D2 |
| 192 | m-D2 | m-D2 | m-D2 | Cz | H |
| 193 | m-D2 | m-D2 | Cz | m-D2 | H |
| 194 | m-D2 | Cz | m-D2 | m-D2 | H |
| 195 | Cz | m-D2 | m-D2 | m-D2 | H |
| 196 | m-D2 | m-D2 | m-D2 | H | Cz |
| 197 | m-D2 | m-D2 | Cz | H | m-D2 |
| 198 | m-D2 | Cz | m-D2 | H | m-D2 |
| 199 | Cz | m-D2 | m-D2 | H | m-D2 |
| 200 | m-D2 | m-D2 | H | m-D2 | Cz |
| 201 | m-D2 | m-D2 | H | Cz | m-D2 |
| 202 | m-D2 | Cz | m-D2 | H | H |
| 203 | m-D2 | m-D2 | H | m-D2 | H |
| 204 | m-D2 | H | m-D2 | m-D2 | H |
| 205 | H | m-D2 | m-D2 | m-D2 | H |
| 206 | m-D2 | m-D2 | m-D2 | m-D2 | Cz |
| 207 | m-D2 | m-D2 | m-D2 | Cz | m-D2 |
| 208 | m-D2 | m-D2 | Cz | m-D2 | m-D2 |
| 209 | m-D2 | m-D2 | m-D2 | m-D2 | H |
| 210 | m-D2 | m-D2 | m-D2 | H | m-D2 |
| 211 | m-D2 | m-D2 | H | m-D2 | m-D2 |
| 212 | m-D2 | m-D2 | m-D2 | m-D2 | m-D2 |
| 213 | m-D3 | Cz | Cz | Cz | Cz |
| 214 | Cz | m-D3 | Cz | Cz | Cz |
| 215 | Cz | Cz | m-D3 | Cz | Cz |
| 216 | m-D3 | Cz | Cz | Cz | H |
| 217 | Cz | m-D3 | Cz | Cz | H |
| 218 | Cz | Cz | m-D3 | Cz | H |
| 219 | Cz | Cz | Cz | m-D3 | H |
| 220 | m-D3 | Cz | Cz | H | Cz |

TABLE 1-4-continued

| | | | | | |
|---|---|---|---|---|---|
| 221 | Cz | m-D3 | Cz | H | Cz |
| 222 | Cz | Cz | m-D3 | H | Cz |
| 223 | Cz | Cz | Cz | H | m-D3 |
| 224 | m-D3 | Cz | H | Cz | Cz |
| 225 | Cz | m-D3 | H | Cz | Cz |
| 226 | m-D3 | Cz | Cz | H | H |
| 227 | Cz | m-D3 | Cz | H | H |
| 228 | Cz | Cz | m-D3 | H | H |
| 229 | m-D3 | Cz | H | Cz | H |
| 230 | Cz | m-D3 | H | Cz | H |
| 231 | Cz | Cz | H | m-D3 | H |
| 232 | m-D3 | H | Cz | Cz | H |
| 233 | Cz | H | m-D3 | Cz | H |
| 234 | Cz | H | Cz | m-D3 | H |
| 235 | H | m-D3 | Cz | Cz | H |

TABLE 1-5

| | | | | | |
|---|---|---|---|---|---|
| 236 | H | Cz | m-D3 | Cz | H |
| 237 | m-D3 | Cz | H | H | Cz |
| 238 | Cz | m-D3 | H | H | Cz |
| 239 | Cz | Cz | H | H | m-D3 |
| 240 | m-D3 | H | Cz | H | Cz |
| 241 | Cz | H | m-D3 | H | Cz |
| 242 | m-D3 | Cz | H | H | H |
| 243 | Cz | m-D3 | H | H | H |
| 244 | m-D3 | H | Cz | H | H |
| 245 | Cz | H | m-D3 | H | H |
| 246 | H | m-D3 | Cz | H | H |
| 247 | H | Cz | m-D3 | H | H |
| 248 | m-D3 | H | H | Cz | H |
| 249 | Cz | H | H | m-D3 | H |
| 250 | H | m-D3 | H | Cz | H |
| 251 | m-D3 | H | H | H | Cz |
| 252 | m-D3 | H | H | H | H |
| 253 | H | m-D3 | H | H | H |
| 254 | H | H | m-D3 | H | H |
| 255 | m-D3 | m-D3 | Cz | Cz | H |
| 256 | m-D3 | Cz | m-D3 | Cz | H |
| 257 | m-D3 | Cz | Cz | m-D3 | H |
| 258 | Cz | m-D3 | m-D3 | Cz | H |
| 259 | Cz | m-D3 | Cz | m-D3 | H |
| 260 | Cz | Cz | m-D3 | m-D3 | H |
| 261 | m-D3 | m-D3 | Cz | H | Cz |
| 262 | m-D3 | Cz | m-D3 | H | Cz |
| 263 | m-D3 | Cz | Cz | H | m-D3 |
| 264 | Cz | m-D3 | m-D3 | H | Cz |
| 265 | Cz | m-D3 | Cz | H | m-D3 |
| 266 | Cz | Cz | m-D3 | H | m-D3 |
| 267 | m-D3 | m-D3 | H | Cz | Cz |
| 268 | m-D3 | Cz | H | m-D3 | Cz |
| 269 | m-D3 | Cz | H | Cz | m-D3 |
| 270 | Cz | m-D3 | H | m-D3 | Cz |
| 271 | m-D3 | m-D3 | Cz | H | H |
| 272 | m-D3 | Cz | m-D3 | H | H |
| 273 | Cz | m-D3 | m-D3 | H | H |
| 274 | m-D3 | m-D3 | H | Cz | H |
| 275 | m-D3 | Cz | H | m-D3 | H |
| 276 | Cz | m-D3 | H | m-D3 | H |
| 277 | m-D3 | H | m-D3 | Cz | H |
| 278 | m-D3 | H | Cz | m-D3 | H |
| 279 | Cz | H | m-D3 | m-D3 | H |
| 280 | H | m-D3 | m-D3 | Cz | H |
| 281 | H | m-D3 | Cz | m-D3 | H |
| 282 | m-D3 | m-D3 | H | H | Cz |
| 283 | m-D3 | Cz | H | H | m-D3 |
| 284 | Cz | m-D3 | H | H | m-D3 |
| 285 | m-D3 | H | m-D3 | H | Cz |
| 286 | m-D3 | H | Cz | H | m-D3 |
| 287 | m-D3 | m-D3 | H | H | H |
| 288 | m-D3 | H | m-D3 | H | H |
| 289 | H | m-D3 | m-D3 | H | H |
| 290 | m-D3 | H | H | m-D3 | H |
| 291 | H | m-D3 | H | m-D3 | H |
| 292 | m-D3 | H | H | H | m-D3 |

TABLE 1-5-continued

| 293 | m-D3 | m-D3 | m-D3 | Cz | Cz |
| 294 | m-D3 | m-D3 | Cz | m-D3 | Cz |

TABLE 1-6

| 295 | m-D3 | m-D3 | Cz | Cz | m-D3 |
| 296 | m-D3 | Cz | m-D3 | m-D3 | Cz |
| 297 | m-D3 | Cz | m-D3 | Cz | m-D3 |
| 298 | m-D3 | m-D3 | m-D3 | Cz | H |
| 299 | m-D3 | m-D3 | Cz | m-D3 | H |
| 300 | m-D3 | Cz | m-D3 | Cz | H |
| 301 | Cz | m-D3 | m-D3 | m-D3 | H |
| 302 | m-D3 | m-D3 | m-D3 | H | Cz |
| 303 | m-D3 | m-D3 | Cz | H | m-D3 |
| 304 | m-D3 | Cz | m-D3 | H | m-D3 |
| 305 | Cz | m-D3 | m-D3 | H | m-D3 |
| 306 | m-D3 | m-D3 | H | m-D3 | Cz |
| 307 | m-D3 | m-D3 | H | Cz | m-D3 |
| 308 | m-D3 | m-D3 | m-D3 | H | H |
| 309 | m-D3 | m-D3 | H | m-D3 | H |
| 310 | m-D3 | H | m-D3 | m-D3 | H |
| 311 | H | m-D3 | m-D3 | m-D3 | H |
| 312 | m-D3 | m-D3 | m-D3 | m-D3 | Cz |
| 313 | m-D3 | m-D3 | m-D3 | Cz | m-D3 |
| 314 | m-D3 | m-D3 | Cz | m-D3 | m-D3 |
| 315 | m-D3 | m-D3 | m-D3 | H | m-D3 |
| 316 | m-D3 | m-D3 | m-D3 | H | m-D3 |
| 317 | m-D3 | m-D3 | H | m-D3 | m-D3 |
| 318 | m-D3 | m-D3 | m-D3 | m-D3 | m-D3 |
| 319 | Cz | Cz | m-D4 | Cz | Cz |
| 320 | m-D4 | Cz | Cz | Cz | H |
| 321 | Cz | Cz | Cz | m-D4 | H |
| 322 | m-D4 | Cz | Cz | H | Cz |
| 323 | Cz | Cz | m-D4 | H | Cz |
| 324 | Cz | m-D4 | H | Cz | Cz |
| 325 | Cz | m-D4 | Cz | H | H |
| 326 | Cz | Cz | m-D4 | H | H |
| 327 | H | m-D4 | Cz | Cz | H |
| 328 | H | Cz | m-D4 | Cz | H |
| 329 | m-D4 | H | Cz | H | Cz |
| 330 | Cz | H | m-D4 | H | Cz |
| 331 | m-D4 | Cz | H | H | H |
| 332 | H | m-D4 | H | Cz | H |
| 333 | m-D4 | m-D4 | Cz | H | Cz |
| 334 | m-D4 | Cz | m-D4 | H | Cz |
| 335 | Cz | m-D4 | m-D4 | H | Cz |
| 336 | m-D4 | Cz | H | Cz | Cz |
| 337 | Cz | m-D4 | H | m-D4 | Cz |
| 338 | m-D4 | Cz | m-D4 | H | H |
| 339 | H | m-D4 | m-D4 | Cz | H |
| 340 | m-D4 | Cz | m-D4 | H | H |
| 341 | m-D4 | H | m-D4 | H | Cz |
| 342 | m-D4 | H | Cz | H | m-D4 |
| 343 | H | m-D4 | m-D4 | H | H |
| 344 | m-D4 | Cz | m-D4 | Cz | m-D4 |
| 345 | m-D4 | m-D4 | m-D4 | Cz | H |
| 346 | m-D4 | m-D4 | Cz | m-D4 | H |
| 347 | m-D4 | m-D4 | m-D4 | H | Cz |
| 348 | m-D4 | m-D4 | H | m-D4 | Cz |
| 349 | m-D4 | m-D4 | H | Cz | m-D4 |
| 350 | m-D4 | m-D4 | H | m-D4 | H |
| 351 | H | m-D4 | m-D4 | m-D4 | H |
| 352 | m-D4 | m-D4 | m-D4 | m-D4 | Cz |
| 353 | m-D4 | m-D4 | m-D4 | m-D4 | H |

TABLE 1-7

| 354 | m-D4 | m-D4 | H | m-D4 | m-D4 |
| 355 | m-D4 | m-D4 | m-D4 | m-D4 | m-D4 |
| 356 | Cz | Cz | m-D5 | Cz | Cz |
| 357 | m-D5 | Cz | Cz | Cz | H |
| 358 | Cz | Cz | Cz | m-D5 | H |
| 359 | m-D5 | Cz | Cz | H | Cz |
| 360 | Cz | Cz | m-D5 | H | Cz |
| 361 | Cz | m-D5 | H | Cz | Cz |
| 362 | Cz | m-D5 | Cz | H | H |
| 363 | Cz | Cz | m-D5 | H | H |
| 364 | H | m-D5 | Cz | Cz | H |
| 365 | H | Cz | m-D5 | Cz | H |
| 366 | m-D5 | H | Cz | H | Cz |
| 367 | Cz | H | m-D5 | H | Cz |
| 368 | m-D5 | Cz | H | H | H |
| 369 | H | m-D5 | H | Cz | H |
| 370 | m-D5 | m-D5 | Cz | H | Cz |
| 371 | m-D5 | Cz | m-D5 | H | Cz |
| 372 | Cz | m-D5 | m-D5 | H | Cz |
| 373 | m-D5 | Cz | H | Cz | Cz |
| 374 | Cz | m-D5 | H | m-D5 | Cz |
| 375 | m-D5 | Cz | m-D5 | H | H |
| 376 | H | m-D5 | m-D5 | Cz | H |
| 377 | H | m-D5 | Cz | m-D5 | H |
| 378 | m-D5 | H | m-D5 | H | Cz |
| 379 | m-D5 | H | Cz | H | m-D5 |
| 380 | H | m-D5 | m-D5 | H | H |
| 381 | m-D5 | Cz | m-D5 | Cz | m-D5 |
| 382 | m-D5 | m-D5 | m-D5 | Cz | H |
| 383 | m-D5 | m-D5 | Cz | m-D5 | H |
| 384 | m-D5 | m-D5 | m-D5 | H | Cz |
| 385 | m-D5 | m-D5 | H | m-D5 | Cz |
| 386 | m-D5 | m-D5 | H | Cz | m-D5 |
| 387 | m-D5 | m-D5 | H | m-D5 | H |
| 388 | H | m-D5 | m-D5 | m-D5 | H |
| 389 | m-D5 | m-D5 | m-D5 | m-D5 | Cz |
| 390 | m-D5 | m-D5 | m-D5 | m-D5 | H |
| 391 | m-D5 | m-D5 | H | m-D5 | m-D5 |
| 392 | m-D5 | m-D5 | m-D5 | m-D5 | m-D5 |
| 393 | Cz | Cz | m-D6 | Cz | Cz |
| 394 | m-D6 | Cz | Cz | Cz | H |
| 395 | Cz | Cz | Cz | m-D6 | H |
| 396 | m-D6 | Cz | Cz | H | Cz |
| 397 | Cz | Cz | m-D6 | H | Cz |
| 398 | Cz | m-D6 | H | Cz | Cz |
| 399 | Cz | m-D6 | Cz | H | H |
| 400 | Cz | Cz | m-D6 | H | H |
| 401 | H | m-D6 | Cz | Cz | H |
| 402 | H | Cz | m-D6 | Cz | H |
| 403 | m-D6 | H | Cz | H | Cz |
| 404 | Cz | H | m-D6 | H | Cz |
| 405 | m-D6 | Cz | H | H | H |
| 406 | H | m-D6 | H | Cz | H |
| 407 | m-D6 | m-D6 | Cz | H | Cz |
| 408 | m-D6 | Cz | m-D6 | H | Cz |
| 409 | Cz | m-D6 | m-D6 | H | Cz |
| 410 | m-D6 | m-D6 | H | Cz | Cz |
| 411 | Cz | m-D6 | H | m-D6 | Cz |
| 412 | m-D6 | Cz | m-D6 | H | H |

TABLE 1-8

| 413 | H | m-D6 | m-D6 | Cz | H |
| 414 | H | m-D6 | Cz | m-D6 | H |
| 415 | m-D6 | H | m-D6 | H | Cz |
| 416 | m-D6 | H | Cz | H | m-D6 |
| 417 | H | m-D6 | m-D6 | H | H |
| 418 | m-D6 | Cz | m-D6 | Cz | m-D6 |
| 419 | m-D6 | m-D6 | m-D6 | Cz | H |
| 420 | m-D6 | m-D6 | Cz | m-D6 | H |
| 421 | m-D6 | m-D6 | m-D6 | H | Cz |
| 422 | m-D6 | m-D6 | H | m-D6 | Cz |
| 423 | m-D6 | m-D6 | H | Cz | m-D6 |
| 424 | m-D6 | m-D6 | H | m-D6 | H |
| 425 | H | m-D6 | m-D6 | m-D6 | H |
| 426 | m-D6 | m-D6 | m-D6 | m-D6 | Cz |
| 427 | m-D6 | m-D6 | m-D6 | m-D6 | H |
| 428 | m-D6 | m-D6 | H | m-D6 | m-D6 |
| 429 | m-D6 | m-D6 | m-D6 | m-D6 | m-D6 |
| 430 | Cz | Cz | m-D7 | Cz | Cz |
| 431 | m-D7 | Cz | Cz | Cz | H |
| 432 | Cz | Cz | Cz | m-D7 | H |
| 433 | m-D7 | Cz | Cz | H | Cz |
| 434 | Cz | Cz | m-D7 | H | Cz |
| 435 | Cz | m-D7 | H | Cz | Cz |

TABLE 1-8-continued

| | | | | | |
|---|---|---|---|---|---|
| 436 | Cz | m-D7 | Cz | H | H |
| 437 | Cz | Cz | m-D7 | H | H |
| 438 | H | m-D7 | Cz | Cz | H |
| 439 | H | Cz | m-D7 | Cz | H |
| 440 | m-D7 | H | Cz | H | Cz |
| 441 | Cz | H | m-D7 | H | Cz |
| 442 | m-D7 | Cz | H | H | H |
| 443 | H | m-D7 | H | Cz | H |
| 444 | m-D7 | m-D7 | Cz | H | H |
| 445 | m-D7 | Cz | m-D7 | H | Cz |
| 446 | Cz | m-D7 | m-D7 | H | Cz |
| 447 | m-D7 | m-D7 | H | Cz | Cz |
| 448 | Cz | m-D7 | H | m-D7 | Cz |
| 449 | m-D7 | Cz | m-D7 | H | H |
| 450 | H | m-D7 | m-D7 | Cz | H |
| 451 | H | m-D7 | Cz | m-D7 | H |
| 452 | m-D7 | H | m-D7 | H | Cz |
| 453 | m-D7 | H | Cz | H | m-D7 |
| 454 | H | m-D7 | m-D7 | H | H |
| 455 | m-D7 | Cz | m-D7 | Cz | m-D7 |
| 456 | m-D7 | m-D7 | m-D7 | Cz | H |
| 457 | m-D7 | m-D7 | Cz | m-D7 | H |
| 458 | m-D7 | m-D7 | m-D7 | H | Cz |
| 459 | m-D7 | m-D7 | H | m-D7 | Cz |
| 460 | m-D7 | m-D7 | H | Cz | m-D7 |
| 461 | m-D7 | m-D7 | H | m-D7 | H |
| 462 | H | m-D7 | m-D7 | m-D7 | H |
| 463 | m-D7 | m-D7 | m-D7 | m-D7 | Cz |
| 464 | m-D7 | m-D7 | m-D7 | m-D7 | H |
| 465 | m-D7 | m-D7 | H | m-D7 | m-D7 |
| 466 | m-D7 | m-D7 | m-D7 | m-D7 | m-D7 |
| 467 | Cz | Cz | m-D8 | Cz | Cz |
| 468 | m-D8 | Cz | Cz | Cz | H |
| 469 | Cz | Cz | Cz | m-D8 | H |
| 470 | m-D8 | Cz | Cz | H | Cz |
| 471 | Cz | Cz | m-D8 | H | Cz |

TABLE 1-9

| | | | | | |
|---|---|---|---|---|---|
| 472 | Cz | m-D8 | H | Cz | Cz |
| 473 | Cz | m-D8 | Cz | H | H |
| 474 | Cz | Cz | m-D8 | H | H |
| 475 | H | m-D8 | Cz | Cz | H |
| 476 | H | Cz | m-D8 | Cz | H |
| 477 | m-D8 | H | Cz | H | Cz |
| 478 | Cz | H | m-D8 | H | Cz |
| 479 | m-D8 | Cz | H | H | H |
| 480 | H | m-D8 | H | Cz | H |
| 481 | m-D8 | m-D8 | Cz | H | Cz |
| 482 | m-D8 | Cz | m-D8 | H | Cz |
| 483 | Cz | m-D8 | m-D8 | H | Cz |
| 484 | m-D8 | Cz | H | Cz | Cz |
| 485 | Cz | m-D8 | H | m-D8 | Cz |
| 486 | m-D8 | Cz | m-D8 | H | H |
| 487 | H | m-D8 | m-D8 | Cz | H |
| 488 | H | m-D8 | Cz | m-D8 | H |
| 489 | m-D8 | H | m-D8 | H | Cz |
| 490 | m-D8 | H | Cz | H | m-D8 |
| 491 | H | m-D8 | m-D8 | H | H |
| 492 | m-D8 | Cz | m-D8 | Cz | m-D8 |
| 493 | m-D8 | m-D8 | m-D8 | Cz | H |
| 494 | m-D8 | m-D8 | Cz | m-D8 | H |
| 495 | m-D8 | m-D8 | m-D8 | H | Cz |
| 496 | m-D8 | m-D8 | H | m-D8 | Cz |
| 497 | m-D8 | m-D8 | H | Cz | m-D8 |
| 498 | m-D8 | m-D8 | H | m-D8 | H |
| 499 | H | m-D8 | m-D8 | m-D8 | H |
| 500 | m-D8 | m-D8 | m-D8 | m-D8 | Cz |
| 501 | m-D8 | m-D8 | m-D8 | m-D8 | H |
| 502 | m-D8 | m-D8 | H | m-D8 | m-D8 |
| 503 | m-D8 | m-D8 | m-D8 | m-D8 | m-D8 |
| 504 | Cz | Cz | m-D9 | Cz | Cz |
| 505 | m-D9 | Cz | Cz | Cz | H |
| 506 | Cz | Cz | Cz | m-D9 | H |
| 507 | m-D9 | Cz | Cz | H | Cz |
| 508 | Cz | Cz | m-D9 | H | Cz |
| 509 | Cz | m-D9 | H | Cz | Cz |

TABLE 1-9-continued

| | | | | | |
|---|---|---|---|---|---|
| 510 | Cz | m-D9 | Cz | H | H |
| 511 | Cz | Cz | m-D9 | H | H |
| 512 | H | m-D9 | Cz | Cz | H |
| 513 | H | Cz | m-D9 | Cz | H |
| 514 | m-D9 | H | Cz | H | Cz |
| 515 | Cz | H | m-D9 | H | Cz |
| 516 | m-D9 | Cz | H | H | H |
| 517 | H | m-D9 | H | Cz | H |
| 518 | m-D9 | m-D9 | Cz | H | Cz |
| 519 | m-D9 | Cz | m-D9 | H | Cz |
| 520 | Cz | m-D9 | m-D9 | H | Cz |
| 521 | m-D9 | m-D9 | H | Cz | Cz |
| 522 | Cz | m-D9 | H | m-D9 | Cz |
| 523 | m-D9 | Cz | m-D9 | H | H |
| 524 | H | m-D9 | m-D9 | Cz | H |
| 525 | H | m-D9 | Cz | m-D9 | H |
| 526 | m-D9 | H | m-D9 | H | Cz |
| 527 | m-D9 | H | Cz | H | m-D9 |
| 528 | H | m-D9 | m-D9 | H | H |
| 529 | m-D9 | Cz | m-D9 | Cz | m-D9 |
| 530 | m-D9 | m-D9 | m-D9 | Cz | H |

TABLE 1-10

| | | | | | |
|---|---|---|---|---|---|
| 531 | m-D9 | m-D9 | Cz | m-D9 | H |
| 532 | m-D9 | m-D9 | m-D9 | H | Cz |
| 533 | m-D9 | m-D9 | H | m-D9 | Cz |
| 534 | m-D9 | m-D9 | H | Cz | m-D9 |
| 535 | m-D9 | m-D9 | H | m-D9 | H |
| 536 | H | m-D9 | m-D9 | m-D9 | H |
| 537 | m-D9 | m-D9 | m-D9 | m-D9 | Cz |
| 538 | m-D9 | m-D9 | m-D9 | m-D9 | H |
| 539 | m-D9 | m-D9 | H | m-D9 | m-D9 |
| 540 | m-D9 | m-D9 | m-D9 | m-D9 | m-D9 |

TABLE 1-11

| No | $R^1$ | $R^2$ | $R^3$ | $R^4$ | $R^5$ |
|---|---|---|---|---|---|
| 541 | m-D1 | Cz1 | Cz1 | Cz1 | Cz1 |
| 542 | Cz1 | m-D1 | Cz1 | Cz1 | Cz1 |
| 543 | Cz1 | Cz1 | m-D1 | Cz1 | Cz1 |
| 544 | m-D1 | Cz1 | Cz1 | Cz1 | H |
| 545 | Cz1 | m-D1 | Cz1 | Cz1 | H |
| 546 | Cz1 | Cz1 | m-D1 | Cz1 | H |
| 547 | Cz1 | Cz1 | Cz1 | m-D1 | H |
| 548 | m-D1 | Cz1 | Cz1 | H | Cz1 |
| 549 | Cz1 | m-D1 | Cz1 | H | Cz1 |
| 550 | Cz1 | Cz1 | m-D1 | H | Cz1 |
| 551 | Cz1 | Cz1 | Cz1 | H | m-D1 |
| 552 | m-D1 | Cz1 | H | Cz1 | Cz1 |
| 553 | Cz1 | m-D1 | H | Cz1 | Cz1 |
| 554 | m-D1 | Cz1 | Cz1 | H | H |
| 555 | Cz1 | m-D1 | Cz1 | H | H |
| 556 | Cz1 | Cz1 | m-D1 | H | H |
| 557 | m-D1 | Cz1 | H | Cz1 | H |
| 558 | Cz1 | m-D1 | H | Cz1 | H |
| 559 | Cz1 | Cz1 | H | m-D1 | H |
| 560 | m-D1 | H | Cz1 | Cz1 | H |
| 561 | Cz1 | H | m-D1 | Cz1 | H |
| 562 | Cz1 | H | Cz1 | m-D1 | H |
| 563 | H | Cz1 | m-D1 | Cz1 | H |
| 564 | H | Cz1 | Cz1 | m-D1 | H |
| 565 | m-D1 | Cz1 | H | H | Cz1 |
| 566 | Cz1 | m-D1 | H | H | Cz1 |
| 567 | Cz1 | Cz1 | H | H | m-D1 |
| 568 | m-D1 | H | Cz1 | H | Cz1 |
| 569 | Cz1 | H | m-D1 | H | Cz1 |
| 570 | m-D1 | Cz1 | H | H | H |
| 571 | Cz1 | m-D1 | H | H | H |
| 572 | m-D1 | H | Cz1 | H | H |
| 573 | Cz1 | H | m-D1 | H | H |
| 574 | H | m-D1 | Cz1 | H | H |
| 575 | H | Cz1 | m-D1 | H | H |
| 576 | m-D1 | H | H | Cz1 | H |

TABLE 1-11-continued

| No | R¹ | R² | R³ | R⁴ | R⁵ |
|---|---|---|---|---|---|
| 577 | Cz1 | H | H | m-D1 | H |
| 578 | H | m-D1 | H | Cz1 | H |
| 579 | m-D1 | H | H | H | Cz1 |
| 580 | m-D1 | m-D1 | Cz1 | Cz1 | H |
| 581 | m-D1 | Cz1 | m-D1 | Cz1 | H |
| 582 | m-D1 | Cz1 | Cz1 | m-D1 | H |
| 583 | Cz1 | m-D1 | m-D1 | Cz1 | H |
| 584 | Cz1 | m-D1 | Cz1 | m-D1 | H |
| 585 | Cz1 | Cz1 | m-D1 | m-D1 | H |
| 586 | m-D1 | m-D1 | Cz1 | H | Cz1 |
| 587 | m-D1 | Cz1 | m-D1 | H | Cz1 |
| 588 | m-D1 | Cz1 | Cz1 | H | m-D1 |
| 589 | Cz1 | m-D1 | m-D1 | H | Cz1 |
| 590 | Cz1 | m-D1 | Cz1 | H | m-D1 |
| 591 | Cz1 | Cz1 | m-D1 | H | m-D1 |
| 592 | m-D1 | m-D1 | H | Cz1 | Cz1 |
| 593 | m-D1 | Cz1 | H | m-D1 | Cz1 |
| 594 | m-D1 | Cz1 | H | Cz1 | m-D1 |
| 595 | Cz1 | m-D1 | H | m-D1 | Cz1 |
| 596 | m-D1 | m-D1 | Cz1 | H | H |
| 597 | m-D1 | Cz1 | m-D1 | H | H |
| 598 | m-D1 | Cz1 | m-D1 | H | H |

TABLE 1-12

| No | R¹ | R² | R³ | R⁴ | R⁵ |
|---|---|---|---|---|---|
| 599 | m-D1 | m-D1 | H | Cz1 | H |
| 600 | m-D1 | Cz1 | H | m-D1 | H |
| 601 | Cz1 | m-D1 | H | m-D1 | H |
| 602 | m-D1 | H | m-D1 | Cz1 | H |
| 603 | m-D1 | H | Cz1 | m-D1 | H |
| 604 | Cz1 | H | m-D1 | m-D1 | H |
| 605 | H | m-D1 | m-D1 | Cz1 | H |
| 606 | H | m-D1 | Cz1 | m-D1 | H |
| 607 | m-D1 | m-D1 | H | H | Cz1 |
| 608 | m-D1 | Cz1 | H | H | m-D1 |
| 609 | Cz1 | m-D1 | H | H | m-D1 |
| 610 | m-D1 | H | m-D1 | H | Cz1 |
| 611 | m-D1 | H | Cz1 | H | m-D1 |
| 612 | m-D1 | m-D1 | m-D1 | Cz1 | Cz1 |
| 613 | m-D1 | m-D1 | Cz1 | m-D1 | Cz1 |
| 614 | m-D1 | m-D1 | Cz1 | Cz1 | m-D1 |
| 615 | m-D1 | Cz1 | m-D1 | m-D1 | Cz1 |
| 616 | m-D1 | Cz1 | m-D1 | Cz1 | m-D1 |
| 617 | m-D1 | m-D1 | m-D1 | Cz1 | H |
| 618 | m-D1 | m-D1 | Cz1 | m-D1 | H |
| 619 | m-D1 | Cz1 | m-D1 | Cz1 | H |
| 620 | Cz1 | m-D1 | m-D1 | m-D1 | H |
| 621 | m-D1 | m-D1 | m-D1 | H | Cz1 |
| 622 | m-D1 | m-D1 | Cz1 | H | m-D1 |
| 623 | m-D1 | Cz1 | m-D1 | H | m-D1 |
| 624 | Cz1 | m-D1 | m-D1 | H | m-D1 |
| 625 | m-D1 | m-D1 | H | m-D1 | Cz1 |
| 626 | m-D1 | m-D1 | H | Cz1 | m-D1 |
| 627 | m-D1 | m-D1 | m-D1 | Cz1 | Cz1 |
| 628 | m-D1 | m-D1 | Cz1 | m-D1 | m-D1 |
| 629 | m-D1 | m-D1 | Cz1 | m-D1 | m-D1 |
| 630 | m-D2 | Cz1 | Cz1 | Cz1 | Cz1 |
| 631 | Cz1 | m-D2 | Cz1 | Cz1 | Cz1 |
| 632 | Cz1 | Cz1 | m-D2 | Cz1 | Cz1 |
| 633 | m-D2 | Cz1 | Cz1 | Cz1 | H |
| 634 | Cz1 | m-D2 | Cz1 | Cz1 | H |
| 635 | Cz1 | Cz1 | m-D2 | Cz1 | H |
| 636 | Cz1 | Cz1 | Cz1 | m-D2 | H |
| 637 | m-D2 | Cz1 | Cz1 | H | Cz1 |
| 638 | Cz1 | m-D2 | Cz1 | H | Cz1 |
| 639 | Cz1 | Cz1 | m-D2 | H | Cz1 |
| 640 | Cz1 | Cz1 | Cz1 | H | m-D2 |
| 641 | m-D2 | Cz1 | H | Cz1 | Cz1 |
| 642 | Cz1 | m-D2 | H | Cz1 | Cz1 |
| 643 | m-D2 | Cz1 | Cz1 | H | H |
| 644 | Cz1 | Cz1 | Cz1 | H | H |
| 645 | Cz1 | Cz1 | m-D2 | H | H |
| 646 | m-D2 | Cz1 | H | Cz1 | H |
| 647 | Cz1 | Cz1 | H | Cz1 | H |
| 648 | Cz1 | Cz1 | H | m-D2 | H |

TABLE 1-12-continued

| No | R¹ | R² | R³ | R⁴ | R⁵ |
|---|---|---|---|---|---|
| 649 | m-D2 | H | Cz1 | Cz1 | H |
| 650 | Cz1 | H | m-D2 | Cz1 | H |
| 651 | Cz1 | H | Cz1 | m-D2 | H |
| 652 | H | m-D2 | Cz1 | Cz1 | H |
| 653 | H | Cz1 | m-D2 | Cz1 | H |
| 654 | m-D2 | Cz1 | H | H | Cz1 |
| 655 | Cz1 | m-D2 | H | H | Cz1 |
| 656 | Cz1 | Cz1 | H | H | m-D2 |
| 657 | m-D2 | H | Cz1 | H | Cz1 |

TABLE 1-13

| No | R¹ | R² | R³ | R⁴ | R⁵ |
|---|---|---|---|---|---|
| 658 | Cz1 | H | m-D2 | H | Cz1 |
| 659 | m-D2 | Cz1 | H | H | H |
| 660 | Cz1 | m-D2 | H | H | H |
| 661 | m-D2 | H | Cz1 | H | H |
| 662 | Cz1 | H | m-D2 | H | H |
| 663 | H | m-D2 | Cz1 | H | H |
| 664 | H | Cz1 | m-D2 | H | H |
| 665 | m-D2 | H | H | Cz1 | H |
| 666 | Cz1 | H | H | m-D2 | H |
| 667 | H | m-D2 | H | Cz1 | H |
| 668 | m-D2 | H | H | H | Cz1 |
| 669 | m-D2 | m-D2 | Cz1 | Cz1 | H |
| 670 | m-D2 | Cz1 | m-D2 | Cz1 | H |
| 671 | m-D2 | Cz1 | Cz1 | m-D2 | H |
| 672 | Cz1 | m-D2 | m-D2 | Cz1 | H |
| 673 | Cz1 | m-D2 | Cz1 | m-D2 | H |
| 674 | Cz1 | Cz1 | m-D2 | m-D2 | H |
| 675 | m-D2 | m-D2 | Cz1 | H | Cz1 |
| 676 | m-D2 | Cz1 | m-D2 | H | Cz1 |
| 677 | m-D2 | Cz1 | Cz1 | H | m-D2 |
| 678 | Cz1 | m-D2 | m-D2 | H | Cz1 |
| 679 | Cz1 | m-D2 | Cz1 | H | m-D2 |
| 680 | Cz1 | Cz1 | m-D2 | H | m-D2 |
| 681 | m-D2 | m-D2 | H | Cz1 | Cz1 |
| 682 | m-D2 | Cz1 | H | m-D2 | Cz1 |
| 683 | m-D2 | Cz1 | H | Cz1 | m-D2 |
| 684 | Cz1 | m-D2 | H | m-D2 | Cz1 |
| 685 | m-D2 | m-D2 | Cz1 | H | H |
| 686 | m-D2 | Cz1 | m-D2 | H | H |
| 687 | Cz1 | m-D2 | m-D2 | H | H |
| 688 | m-D2 | m-D2 | H | Cz1 | H |
| 689 | m-D2 | Cz1 | H | m-D2 | H |
| 690 | Cz1 | m-D2 | H | m-D2 | H |
| 691 | m-D2 | H | m-D2 | Cz1 | H |
| 692 | m-D2 | H | Cz1 | m-D2 | H |
| 693 | Cz1 | H | m-D2 | m-D2 | H |
| 694 | H | m-D2 | m-D2 | Cz1 | H |
| 695 | H | m-D2 | Cz1 | m-D2 | H |
| 696 | m-D2 | m-D2 | H | H | Cz1 |
| 697 | m-D2 | Cz1 | H | H | m-D2 |
| 698 | Cz1 | m-D2 | H | H | m-D2 |
| 699 | m-D2 | H | m-D2 | H | Cz1 |
| 700 | m-D2 | H | Cz1 | H | m-D2 |
| 701 | m-D2 | m-D2 | m-D2 | Cz1 | Cz1 |
| 702 | m-D2 | m-D2 | Cz1 | m-D2 | Cz1 |
| 703 | m-D2 | m-D2 | Cz1 | Cz1 | m-D2 |
| 704 | m-D2 | Cz1 | m-D2 | m-D2 | Cz1 |
| 705 | m-D2 | Cz1 | m-D2 | Cz1 | m-D2 |
| 706 | m-D2 | m-D2 | m-D2 | Cz1 | H |
| 707 | m-D2 | m-D2 | Cz1 | m-D2 | H |
| 708 | m-D2 | Cz1 | m-D2 | Cz1 | H |
| 709 | Cz1 | m-D2 | m-D2 | m-D2 | H |
| 710 | m-D2 | m-D2 | m-D2 | H | Cz1 |
| 711 | m-D2 | m-D2 | Cz1 | H | m-D2 |
| 712 | m-D2 | Cz1 | m-D2 | H | m-D2 |
| 713 | Cz1 | m-D2 | m-D2 | H | m-D2 |
| 714 | m-D2 | m-D2 | H | m-D2 | Cz1 |
| 715 | m-D2 | m-D2 | H | Cz1 | m-D2 |
| 716 | m-D2 | m-D2 | m-D2 | m-D2 | Cz1 |

TABLE 1-14

| | | | | | |
|---|---|---|---|---|---|
| 717 | m-D2 | m-D2 | m-D2 | Cz1 | m-D2 |
| 718 | m-D2 | m-D2 | Cz1 | m-D2 | m-D2 |
| 719 | m-D3 | Cz1 | Cz1 | Cz1 | Cz1 |
| 720 | Cz1 | m-D3 | Cz1 | Cz1 | Cz1 |
| 721 | Cz1 | Cz1 | m-D3 | Cz1 | Cz1 |
| 722 | m-D3 | Cz1 | Cz1 | Cz1 | H |
| 723 | Cz1 | m-D3 | Cz1 | Cz1 | H |
| 724 | Cz1 | Cz1 | m-D3 | Cz1 | H |
| 725 | Cz1 | Cz1 | Cz1 | m-D3 | H |
| 726 | m-D3 | Cz1 | Cz1 | H | Cz1 |
| 727 | Cz1 | m-D3 | Cz1 | H | Cz1 |
| 728 | Cz1 | Cz1 | m-D3 | H | Cz1 |
| 729 | Cz1 | Cz1 | Cz1 | H | m-D3 |
| 730 | m-D3 | Cz1 | H | Cz1 | Cz1 |
| 731 | Cz1 | m-D3 | H | Cz1 | Cz1 |
| 732 | m-D3 | Cz1 | Cz1 | H | H |
| 733 | Cz1 | m-D3 | Cz1 | H | H |
| 734 | Cz1 | Cz1 | m-D3 | H | H |
| 735 | m-D3 | Cz1 | H | Cz1 | H |
| 736 | Cz1 | m-D3 | H | Cz1 | H |
| 737 | Cz1 | Cz1 | H | m-D3 | H |
| 738 | m-D3 | H | Cz1 | Cz1 | H |
| 739 | Cz1 | H | m-D3 | Cz1 | H |
| 740 | Cz1 | H | Cz1 | m-D3 | H |
| 741 | H | m-D3 | Cz1 | Cz1 | H |
| 742 | H | Cz1 | m-D3 | Cz1 | H |
| 743 | m-D3 | Cz1 | H | H | Cz1 |
| 744 | Cz1 | m-D3 | H | H | Cz1 |
| 745 | Cz1 | Cz1 | H | H | m-D3 |
| 746 | m-D3 | H | Cz1 | H | Cz1 |
| 747 | Cz1 | H | m-D3 | H | Cz1 |
| 748 | m-D3 | Cz1 | H | H | H |
| 749 | Cz1 | m-D3 | H | H | H |
| 750 | m-D3 | H | Cz1 | H | H |
| 751 | Cz1 | H | m-D3 | H | H |
| 752 | H | m-D3 | Cz1 | H | H |
| 753 | H | Cz1 | m-D3 | H | H |
| 754 | m-D3 | H | H | Cz1 | H |
| 755 | Cz1 | H | H | m-D3 | H |
| 756 | H | m-D3 | H | Cz1 | H |
| 757 | m-D3 | H | H | H | Cz1 |
| 758 | m-D3 | m-D3 | Cz1 | Cz1 | H |
| 759 | m-D3 | Cz1 | m-D3 | Cz1 | H |
| 760 | m-D3 | Cz1 | Cz1 | m-D3 | H |
| 761 | Cz1 | m-D3 | m-D3 | Cz1 | H |
| 762 | Cz1 | m-D3 | Cz1 | m-D3 | H |
| 763 | Cz1 | Cz1 | m-D3 | m-D3 | H |
| 764 | m-D3 | m-D3 | Cz1 | H | Cz1 |
| 765 | m-D3 | Cz1 | m-D3 | H | Cz1 |
| 766 | m-D3 | Cz1 | Cz1 | H | m-D3 |
| 767 | Cz1 | m-D3 | m-D3 | H | Cz1 |
| 768 | Cz1 | m-D3 | Cz1 | H | m-D3 |
| 769 | Cz1 | Cz1 | m-D3 | H | m-D3 |
| 770 | m-D3 | m-D3 | H | Cz1 | Cz1 |
| 771 | m-D3 | Cz1 | H | m-D3 | Cz1 |
| 772 | m-D3 | Cz1 | H | Cz1 | m-D3 |
| 773 | Cz1 | m-D3 | H | m-D3 | Cz1 |
| 774 | m-D3 | Cz1 | Cz1 | H | H |
| 775 | m-D3 | Cz1 | m-D3 | H | H |

TABLE 1-15

| | | | | | |
|---|---|---|---|---|---|
| 776 | Cz1 | m-D3 | m-D3 | H | H |
| 777 | m-D3 | m-D3 | H | Cz1 | H |
| 778 | m-D3 | Cz1 | H | m-D3 | H |
| 779 | Cz1 | m-D3 | H | m-D3 | H |
| 780 | m-D3 | H | m-D3 | Cz1 | H |
| 781 | m-D3 | H | Cz1 | m-D3 | H |
| 782 | Cz1 | H | m-D3 | m-D3 | H |
| 783 | H | m-D3 | m-D3 | Cz1 | H |
| 784 | H | m-D3 | Cz1 | m-D3 | H |
| 785 | m-D3 | m-D3 | H | H | Cz1 |
| 786 | m-D3 | Cz1 | H | H | m-D3 |
| 787 | Cz1 | m-D3 | H | H | m-D3 |
| 788 | m-D3 | H | m-D3 | H | Cz1 |
| 789 | m-D3 | H | Cz1 | H | m-D3 |
| 790 | m-D3 | m-D3 | m-D3 | Cz1 | Cz1 |
| 791 | m-D3 | m-D3 | Cz1 | m-D3 | Cz1 |
| 792 | m-D3 | m-D3 | Cz1 | Cz1 | m-D3 |
| 793 | m-D3 | Cz1 | m-D3 | m-D3 | Cz1 |
| 794 | m-D3 | Cz1 | m-D3 | Cz1 | m-D3 |
| 795 | m-D3 | m-D3 | m-D3 | Cz1 | H |
| 796 | m-D3 | m-D3 | Cz1 | m-D3 | H |
| 797 | m-D3 | Cz1 | m-D3 | Cz1 | H |
| 798 | Cz1 | m-D3 | m-D3 | m-D3 | H |
| 799 | m-D3 | m-D3 | m-D3 | H | Cz1 |
| 800 | m-D3 | m-D3 | Cz1 | H | m-D3 |
| 801 | m-D3 | Cz1 | m-D3 | H | m-D3 |
| 802 | Cz1 | m-D3 | m-D3 | H | m-D3 |
| 803 | m-D3 | m-D3 | H | m-D3 | Cz1 |
| 804 | m-D3 | m-D3 | H | Cz1 | m-D3 |
| 805 | m-D3 | m-D3 | m-D3 | m-D3 | Cz1 |
| 806 | m-D3 | m-D3 | m-D3 | Cz1 | m-D3 |
| 807 | m-D3 | m-D3 | Cz1 | m-D3 | m-D3 |
| 808 | m-D1 | Cz2 | Cz2 | Cz2 | Cz2 |
| 809 | Cz2 | m-D1 | Cz2 | Cz2 | Cz2 |
| 810 | Cz2 | Cz2 | m-D1 | Cz2 | Cz2 |
| 811 | m-D1 | Cz2 | Cz2 | Cz2 | H |
| 812 | Cz2 | m-D1 | Cz2 | Cz2 | H |
| 813 | Cz2 | Cz2 | m-D1 | Cz2 | H |
| 814 | Cz2 | Cz2 | Cz2 | m-D1 | H |
| 815 | m-D1 | Cz2 | Cz2 | H | Cz2 |
| 816 | Cz2 | m-D1 | Cz2 | H | Cz2 |
| 817 | Cz2 | Cz2 | m-D1 | H | Cz2 |
| 818 | Cz2 | Cz2 | Cz2 | H | m-D1 |
| 819 | m-D1 | Cz2 | H | Cz2 | Cz2 |
| 820 | Cz2 | m-D1 | H | Cz2 | Cz2 |
| 821 | m-D1 | Cz2 | Cz2 | H | H |
| 822 | Cz2 | m-D1 | Cz2 | H | H |
| 823 | Cz2 | Cz2 | m-D1 | H | H |
| 824 | m-D1 | Cz2 | H | Cz2 | H |
| 825 | Cz2 | m-D1 | H | Cz2 | H |
| 826 | Cz2 | Cz2 | H | m-D1 | H |
| 827 | m-D1 | H | Cz2 | Cz2 | H |
| 828 | Cz2 | H | m-D1 | Cz2 | H |
| 829 | Cz2 | H | Cz2 | m-D1 | H |
| 830 | H | m-D1 | Cz2 | Cz2 | H |
| 831 | H | Cz2 | m-D1 | Cz2 | H |
| 832 | m-D1 | Cz2 | H | H | Cz2 |
| 833 | Cz2 | m-D1 | H | H | Cz2 |
| 834 | Cz2 | Cz2 | H | H | m-D1 |

TABLE 1-16

| | | | | | |
|---|---|---|---|---|---|
| 835 | m-D1 | H | Cz2 | H | Cz2 |
| 836 | Cz2 | H | m-D1 | H | Cz2 |
| 837 | m-D1 | Cz2 | H | H | H |
| 838 | Cz2 | m-D1 | H | H | H |
| 839 | m-D1 | H | Cz2 | H | H |
| 840 | Cz2 | H | m-D1 | H | H |
| 841 | H | m-D1 | Cz2 | H | H |
| 842 | H | Cz2 | m-D1 | H | H |
| 843 | m-D1 | H | H | Cz2 | H |
| 844 | Cz2 | H | H | m-D1 | H |
| 845 | H | m-D1 | H | Cz2 | H |
| 846 | m-D1 | H | H | H | Cz2 |
| 847 | m-D1 | m-D1 | Cz2 | Cz2 | H |
| 848 | m-D1 | Cz2 | m-D1 | Cz2 | H |
| 849 | m-D1 | Cz2 | Cz2 | m-D1 | H |
| 850 | Cz2 | m-D1 | m-D1 | Cz2 | H |
| 851 | Cz2 | m-D1 | Cz2 | m-D1 | H |
| 852 | Cz2 | Cz2 | m-D1 | m-D1 | H |
| 853 | m-D1 | m-D1 | Cz2 | H | Cz2 |
| 854 | m-D1 | Cz2 | m-D1 | H | Cz2 |
| 855 | m-D1 | Cz2 | Cz2 | H | m-D1 |
| 856 | Cz2 | m-D1 | m-D1 | H | Cz2 |
| 857 | Cz2 | m-D1 | Cz2 | H | m-D1 |
| 858 | Cz2 | Cz2 | m-D1 | H | m-D1 |
| 859 | m-D1 | m-D1 | H | Cz2 | Cz2 |
| 860 | m-D1 | Cz2 | H | m-D1 | Cz2 |
| 861 | m-D1 | Cz2 | H | Cz2 | m-D1 |
| 862 | Cz2 | m-D1 | H | m-D1 | Cz2 |
| 863 | m-D1 | m-D1 | Cz2 | H | H |
| 864 | m-D1 | Cz2 | m-D1 | H | H |

TABLE 1-16-continued

|  |  |  |  |  |  |
|---|---|---|---|---|---|
| 865 | Cz2 | m-D1 | m-D1 | H | H |
| 866 | m-D1 | m-D1 | H | Cz2 | H |
| 867 | m-D1 | Cz2 | H | m-D1 | H |
| 868 | Cz2 | m-D1 | H | m-D1 | H |
| 869 | m-D1 | H | m-D1 | Cz2 | H |
| 870 | m-D1 | H | Cz2 | m-D1 | H |
| 871 | Cz2 | H | m-D1 | m-D1 | H |
| 872 | H | m-D1 | m-D1 | Cz2 | H |
| 873 | H | m-D1 | Cz2 | m-D1 | H |
| 874 | m-D1 | m-D1 | H | H | Cz2 |
| 875 | m-D1 | Cz2 | H | H | m-D1 |
| 876 | Cz2 | m-D1 | H | H | m-D1 |
| 877 | m-D1 | m-D1 | m-D1 | H | Cz2 |
| 878 | m-D1 | H | Cz2 | H | m-D1 |
| 879 | m-D1 | m-D1 | m-D1 | Cz2 | Cz2 |
| 880 | m-D1 | m-D1 | Cz2 | m-D1 | Cz2 |
| 881 | m-D1 | m-D1 | Cz2 | Cz2 | m-D1 |
| 882 | m-D1 | Cz2 | m-D1 | m-D1 | Cz2 |
| 883 | m-D1 | Cz2 | m-D1 | Cz2 | m-D1 |
| 884 | m-D1 | m-D1 | m-D1 | Cz2 | H |
| 885 | m-D1 | m-D1 | Cz2 | m-D1 | H |
| 886 | m-D1 | Cz2 | m-D1 | Cz2 | H |
| 887 | Cz2 | m-D1 | m-D1 | m-D1 | H |
| 888 | m-D1 | m-D1 | m-D1 | H | Cz2 |
| 889 | m-D1 | m-D1 | Cz2 | H | m-D1 |
| 890 | m-D1 | Cz2 | m-D1 | H | m-D1 |
| 891 | Cz2 | m-D1 | m-D1 | H | m-D1 |
| 892 | m-D1 | m-D1 | H | m-D1 | Cz2 |
| 893 | m-D1 | m-D1 | H | Cz2 | m-D1 |

TABLE 1-17

|  |  |  |  |  |  |
|---|---|---|---|---|---|
| 894 | m-D1 | m-D1 | m-D1 | m-D1 | Cz2 |
| 895 | m-D1 | m-D1 | m-D1 | Cz2 | m-D1 |
| 896 | m-D1 | m-D1 | Cz2 | m-D1 | m-D1 |
| 897 | m-D2 | Cz2 | Cz2 | Cz2 | Cz2 |
| 898 | Cz2 | m-D2 | Cz2 | Cz2 | Cz2 |
| 899 | Cz2 | Cz2 | m-D2 | Cz2 | Cz2 |
| 900 | m-D2 | Cz2 | Cz2 | Cz2 | H |
| 901 | Cz2 | m-D2 | Cz2 | Cz2 | H |
| 902 | Cz2 | Cz2 | m-D2 | Cz2 | H |
| 903 | Cz2 | Cz2 | Cz2 | m-D2 | H |
| 904 | m-D2 | Cz2 | Cz2 | H | Cz2 |
| 905 | Cz2 | m-D2 | Cz2 | H | Cz2 |
| 906 | Cz2 | Cz2 | m-D2 | H | Cz2 |
| 907 | Cz2 | Cz2 | Cz2 | H | m-D2 |
| 908 | m-D2 | Cz2 | H | Cz2 | Cz2 |
| 909 | Cz2 | m-D2 | H | Cz2 | Cz2 |
| 910 | m-D2 | Cz2 | Cz2 | H | H |
| 911 | Cz2 | m-D2 | Cz2 | H | H |
| 912 | Cz2 | Cz2 | m-D2 | H | H |
| 913 | m-D2 | Cz2 | H | Cz2 | H |
| 914 | Cz2 | m-D2 | H | Cz2 | H |
| 915 | Cz2 | Cz2 | H | m-D2 | H |
| 916 | m-D2 | H | Cz2 | Cz2 | H |
| 917 | Cz2 | H | m-D2 | Cz2 | H |
| 918 | Cz2 | H | Cz2 | m-D2 | H |
| 919 | H | m-D2 | Cz2 | Cz2 | H |
| 920 | H | Cz2 | m-D2 | Cz2 | H |
| 921 | m-D2 | Cz2 | H | H | Cz2 |
| 922 | Cz2 | m-D2 | H | H | Cz2 |
| 923 | Cz2 | Cz2 | H | H | m-D2 |
| 924 | m-D2 | H | Cz2 | H | Cz2 |
| 925 | Cz2 | H | m-D2 | H | Cz2 |
| 926 | m-D2 | Cz2 | H | H | H |
| 927 | Cz2 | m-D2 | H | H | H |
| 928 | m-D2 | H | Cz2 | H | H |
| 929 | Cz2 | H | m-D2 | H | H |
| 930 | H | m-D2 | Cz2 | H | H |
| 931 | H | Cz2 | m-D2 | H | H |
| 932 | m-D2 | H | H | Cz2 | H |
| 933 | Cz2 | H | H | m-D2 | H |
| 934 | H | m-D2 | H | Cz2 | H |
| 935 | m-D2 | H | H | H | Cz2 |
| 936 | m-D2 | m-D2 | Cz2 | H | H |
| 937 | m-D2 | Cz2 | m-D2 | H | H |
| 938 | m-D2 | Cz2 | Cz2 | m-D2 | H |

TABLE 1-17-continued

|  |  |  |  |  |  |
|---|---|---|---|---|---|
| 939 | Cz2 | m-D2 | m-D2 | Cz2 | H |
| 940 | Cz2 | m-D2 | Cz2 | m-D2 | H |
| 941 | Cz2 | Cz2 | m-D2 | m-D2 | H |
| 942 | m-D2 | m-D2 | Cz2 | H | Cz2 |
| 943 | m-D2 | Cz2 | m-D2 | H | Cz2 |
| 944 | m-D2 | Cz2 | Cz2 | H | m-D2 |
| 945 | Cz2 | m-D2 | m-D2 | H | Cz2 |
| 946 | Cz2 | m-D2 | Cz2 | H | m-D2 |
| 947 | Cz2 | Cz2 | m-D2 | H | m-D2 |
| 948 | m-D2 | m-D2 | H | Cz2 | Cz2 |
| 949 | m-D2 | Cz2 | H | m-D2 | Cz2 |
| 950 | m-D2 | Cz2 | H | Cz2 | m-D2 |
| 951 | Cz2 | m-D2 | H | m-D2 | Cz2 |
| 952 | m-D2 | m-D2 | Cz2 | H | H |

TABLE 1-18

|  |  |  |  |  |  |
|---|---|---|---|---|---|
| 953 | m-D2 | Cz2 | m-D2 | H | H |
| 954 | Cz2 | m-D2 | m-D2 | H | H |
| 955 | m-D2 | m-D2 | H | Cz2 | H |
| 956 | m-D2 | Cz2 | H | m-D2 | H |
| 957 | Cz2 | m-D2 | H | m-D2 | H |
| 958 | m-D2 | H | m-D2 | Cz2 | H |
| 959 | m-D2 | H | Cz2 | m-D2 | H |
| 960 | Cz2 | H | m-D2 | m-D2 | H |
| 961 | H | m-D2 | m-D2 | Cz2 | H |
| 962 | H | m-D2 | Cz2 | m-D2 | H |
| 963 | m-D2 | m-D2 | H | H | Cz2 |
| 964 | m-D2 | Cz2 | H | H | m-D2 |
| 965 | Cz2 | m-D2 | H | H | m-D2 |
| 966 | m-D2 | H | m-D2 | H | Cz2 |
| 967 | m-D2 | H | Cz2 | H | m-D2 |
| 968 | m-D2 | m-D2 | m-D2 | Cz2 | Cz2 |
| 969 | m-D2 | m-D2 | Cz2 | m-D2 | Cz2 |
| 970 | m-D2 | m-D2 | Cz2 | Cz2 | m-D2 |
| 971 | m-D2 | Cz2 | m-D2 | m-D2 | Cz2 |
| 972 | m-D2 | Cz2 | m-D2 | Cz2 | m-D2 |
| 973 | m-D2 | m-D2 | m-D2 | Cz2 | H |
| 974 | m-D2 | m-D2 | Cz2 | m-D2 | H |
| 975 | m-D2 | Cz2 | m-D2 | Cz2 | H |
| 976 | Cz2 | m-D2 | m-D2 | m-D2 | H |
| 977 | m-D2 | m-D2 | m-D2 | H | Cz2 |
| 978 | m-D2 | m-D2 | Cz2 | H | m-D2 |
| 979 | m-D2 | Cz2 | m-D2 | H | m-D2 |
| 980 | Cz2 | m-D2 | m-D2 | H | m-D2 |
| 981 | m-D2 | m-D2 | H | m-D2 | Cz2 |
| 982 | m-D2 | m-D2 | H | Cz2 | m-D2 |
| 983 | m-D2 | Cz2 | m-D2 | m-D2 | Cz2 |
| 984 | m-D2 | m-D2 | m-D2 | Cz2 | m-D2 |
| 985 | m-D2 | m-D2 | Cz2 | m-D2 | m-D2 |
| 986 | m-D3 | Cz2 | Cz2 | Cz2 | Cz2 |
| 987 | Cz2 | m-D3 | Cz2 | Cz2 | Cz2 |
| 988 | Cz2 | Cz2 | m-D3 | Cz2 | Cz2 |
| 989 | m-D3 | Cz2 | Cz2 | Cz2 | H |
| 990 | Cz2 | m-D3 | Cz2 | Cz2 | H |
| 991 | Cz2 | Cz2 | m-D3 | Cz2 | H |
| 992 | Cz2 | Cz2 | Cz2 | m-D3 | H |
| 993 | m-D3 | Cz2 | Cz2 | H | Cz2 |
| 994 | Cz2 | Cz2 | Cz2 | H | Cz2 |
| 995 | Cz2 | Cz2 | m-D3 | Cz2 | Cz2 |
| 996 | Cz2 | Cz2 | Cz2 | H | m-D3 |
| 997 | m-D3 | Cz2 | H | Cz2 | Cz2 |
| 998 | Cz2 | m-D3 | H | Cz2 | Cz2 |
| 999 | m-D3 | Cz2 | Cz2 | H | H |
| 1000 | Cz2 | m-D3 | Cz2 | H | H |
| 1001 | Cz2 | Cz2 | m-D3 | H | H |
| 1002 | m-D3 | Cz2 | H | Cz2 | H |
| 1003 | Cz2 | Cz2 | H | m-D3 | H |
| 1004 | Cz2 | Cz2 | H | m-D3 | H |
| 1005 | m-D3 | H | Cz2 | Cz2 | H |
| 1006 | Cz2 | H | m-D3 | Cz2 | H |
| 1007 | Cz2 | H | Cz2 | m-D3 | H |
| 1008 | H | m-D3 | Cz2 | Cz2 | H |
| 1009 | H | Cz2 | m-D3 | Cz2 | H |
| 1010 | m-D3 | Cz2 | H | H | Cz2 |
| 1011 | Cz2 | m-D3 | H | H | Cz2 |

TABLE 1-19

| | | | | | |
|---|---|---|---|---|---|
| 1012 | Cz2  | Cz2  | H    | H    | m-D3 |
| 1013 | m-D3 | H    | Cz2  | H    | Cz2  |
| 1014 | Cz2  | H    | m-D3 | H    | Cz2  |
| 1015 | m-D3 | Cz2  | H    | H    | H    |
| 1016 | Cz2  | m-D3 | H    | H    | H    |
| 1017 | m-D3 | H    | Cz2  | H    | H    |
| 1018 | Cz2  | H    | m-D3 | H    | H    |
| 1019 | H    | m-D3 | Cz2  | H    | H    |
| 1020 | H    | Cz2  | m-D3 | H    | H    |
| 1021 | m-D3 | H    | H    | Cz2  | H    |
| 1022 | Cz2  | H    | H    | m-D3 | H    |
| 1023 | H    | m-D3 | H    | Cz2  | H    |
| 1024 | m-D3 | H    | H    | H    | Cz2  |
| 1025 | m-D3 | m-D3 | Cz2  | Cz2  | H    |
| 1026 | m-D3 | Cz2  | m-D3 | Cz2  | H    |
| 1027 | m-D3 | Cz2  | Cz2  | m-D3 | H    |
| 1028 | Cz2  | m-D3 | m-D3 | Cz2  | H    |
| 1029 | Cz2  | m-D3 | Cz2  | m-D3 | H    |
| 1030 | Cz2  | Cz2  | m-D3 | m-D3 | H    |
| 1031 | m-D3 | m-D3 | Cz2  | H    | Cz2  |
| 1032 | m-D3 | Cz2  | m-D3 | H    | Cz2  |
| 1033 | m-D3 | Cz2  | Cz2  | H    | m-D3 |
| 1034 | Cz2  | m-D3 | m-D3 | H    | Cz2  |
| 1035 | Cz2  | m-D3 | Cz2  | H    | m-D3 |
| 1036 | Cz2  | Cz2  | m-D3 | H    | m-D3 |
| 1037 | m-D3 | m-D3 | H    | Cz2  | Cz2  |
| 1038 | m-D3 | Cz2  | H    | m-D3 | Cz2  |
| 1039 | m-D3 | Cz2  | H    | Cz2  | m-D3 |
| 1040 | Cz2  | m-D3 | H    | m-D3 | Cz2  |
| 1041 | m-D3 | m-D3 | Cz2  | H    | H    |
| 1042 | m-D3 | Cz2  | m-D3 | H    | H    |
| 1043 | Cz2  | m-D3 | m-D3 | H    | H    |
| 1044 | m-D3 | m-D3 | H    | Cz2  | H    |
| 1045 | m-D3 | Cz2  | H    | m-D3 | H    |
| 1046 | Cz2  | m-D3 | H    | m-D3 | H    |
| 1047 | m-D3 | H    | m-D3 | Cz2  | H    |
| 1048 | m-D3 | H    | Cz2  | m-D3 | H    |
| 1049 | Cz2  | H    | m-D3 | m-D3 | H    |
| 1050 | H    | m-D3 | m-D3 | Cz2  | H    |
| 1051 | H    | m-D3 | Cz2  | m-D3 | H    |
| 1052 | m-D3 | m-D3 | H    | H    | Cz2  |
| 1053 | m-D3 | Cz2  | H    | H    | m-D3 |
| 1054 | Cz2  | m-D3 | H    | H    | m-D3 |
| 1055 | m-D3 | H    | m-D3 | H    | Cz2  |
| 1056 | m-D3 | H    | Cz2  | H    | m-D3 |
| 1057 | m-D3 | m-D3 | m-D3 | Cz2  | H    |
| 1058 | m-D3 | m-D3 | Cz2  | m-D3 | Cz2  |
| 1059 | m-D3 | m-D3 | Cz2  | Cz2  | m-D3 |
| 1060 | m-D3 | Cz2  | m-D3 | m-D3 | Cz2  |
| 1061 | m-D3 | Cz2  | m-D3 | Cz2  | m-D3 |
| 1062 | m-D3 | m-D3 | m-D3 | Cz2  | H    |
| 1063 | m-D3 | m-D3 | m-D3 | Cz2  | H    |
| 1064 | m-D3 | Cz2  | m-D3 | Cz2  | H    |
| 1065 | Cz2  | m-D3 | m-D3 | m-D3 | H    |
| 1066 | m-D3 | m-D3 | m-D3 | H    | Cz2  |
| 1067 | m-D3 | m-D3 | Cz2  | H    | m-D3 |
| 1068 | m-D3 | Cz2  | m-D3 | H    | m-D3 |
| 1069 | Cz2  | m-D3 | m-D3 | H    | m-D3 |
| 1070 | m-D3 | m-D3 | H    | m-D3 | Cz2  |

TABLE 1-20

| | | | | | |
|---|---|---|---|---|---|
| 1071 | m-D3 | m-D3 | H    | Cz2  | m-D3 |
| 1072 | m-D3 | m-D3 | m-D3 | m-D3 | Cz2  |
| 1073 | m-D3 | m-D3 | m-D3 | Cz2  | m-D3 |
| 1074 | m-D3 | m-D3 | Cz2  | m-D3 | m-D3 |
| 1075 | m-D1 | Cz3  | Cz3  | Cz3  | Cz3  |
| 1076 | Cz3  | m-D1 | Cz3  | Cz3  | Cz3  |
| 1077 | Cz3  | Cz3  | m-D1 | Cz3  | Cz3  |
| 1078 | m-D1 | Cz3  | Cz3  | Cz3  | H    |
| 1079 | Cz3  | m-D1 | Cz3  | Cz3  | H    |
| 1080 | Cz3  | Cz3  | Cz3  | m-D1 | H    |
| 1081 | Cz3  | Cz3  | Cz3  | m-D1 | H    |
| 1082 | m-D1 | Cz3  | Cz3  | H    | Cz3  |
| 1083 | Cz3  | m-D1 | Cz3  | H    | Cz3  |
| 1084 | Cz3  | Cz3  | m-D1 | H    | Cz3  |
| 1085 | Cz3  | Cz3  | Cz3  | H    | m-D1 |

TABLE 1-20-continued

| | | | | | |
|---|---|---|---|---|---|
| 1086 | m-D1 | Cz3  | H    | Cz3  | Cz3  |
| 1087 | Cz3  | m-D1 | H    | Cz3  | Cz3  |
| 1088 | m-D1 | Cz3  | Cz3  | H    | H    |
| 1089 | Cz3  | m-D1 | Cz3  | H    | H    |
| 1090 | Cz3  | Cz3  | m-D1 | H    | H    |
| 1091 | m-D1 | Cz3  | H    | Cz3  | H    |
| 1092 | Cz3  | m-D1 | H    | Cz3  | H    |
| 1093 | Cz3  | Cz3  | H    | m-D1 | H    |
| 1094 | m-D1 | H    | Cz3  | Cz3  | H    |
| 1095 | Cz3  | H    | m-D1 | Cz3  | H    |
| 1096 | Cz3  | H    | Cz3  | m-D1 | H    |
| 1097 | H    | m-D1 | Cz3  | Cz3  | H    |
| 1098 | H    | Cz3  | m-D1 | Cz3  | H    |
| 1099 | m-D1 | Cz3  | H    | H    | Cz3  |
| 1100 | Cz3  | m-D1 | H    | H    | Cz3  |
| 1101 | Cz3  | Cz3  | H    | H    | m-D1 |
| 1102 | m-D1 | H    | Cz3  | H    | Cz3  |
| 1103 | Cz3  | H    | m-D1 | H    | Cz3  |
| 1104 | m-D1 | Cz3  | H    | H    | H    |
| 1105 | Cz3  | m-D1 | H    | H    | H    |
| 1106 | m-D1 | H    | Cz3  | H    | H    |
| 1107 | Cz3  | H    | m-D1 | H    | H    |
| 1108 | H    | m-D1 | Cz3  | H    | H    |
| 1109 | H    | Cz3  | m-D1 | H    | H    |
| 1110 | m-D1 | H    | H    | Cz3  | H    |
| 1111 | Cz3  | H    | H    | m-D1 | H    |
| 1112 | H    | m-D1 | H    | Cz3  | H    |
| 1113 | m-D1 | H    | H    | H    | Cz3  |
| 1114 | m-D1 | m-D1 | Cz3  | Cz3  | H    |
| 1115 | m-D1 | Cz3  | m-D1 | Cz3  | H    |
| 1116 | m-D1 | Cz3  | Cz3  | m-D1 | H    |
| 1117 | Cz3  | m-D1 | m-D1 | Cz3  | H    |
| 1118 | Cz3  | m-D1 | Cz3  | m-D1 | H    |
| 1119 | Cz3  | Cz3  | m-D1 | m-D1 | H    |
| 1120 | m-D1 | m-D1 | Cz3  | H    | Cz3  |
| 1121 | m-D1 | Cz3  | m-D1 | H    | Cz3  |
| 1122 | m-D1 | Cz3  | Cz3  | H    | m-D1 |
| 1123 | Cz3  | m-D1 | m-D1 | H    | Cz3  |
| 1124 | Cz3  | m-D1 | Cz3  | H    | m-D1 |
| 1125 | Cz3  | Cz3  | m-D1 | H    | m-D1 |
| 1126 | m-D1 | m-D1 | H    | Cz3  | Cz3  |
| 1127 | m-D1 | Cz3  | H    | m-D1 | Cz3  |
| 1128 | m-D1 | Cz3  | H    | Cz3  | m-D1 |
| 1129 | Cz3  | m-D1 | H    | m-D1 | Cz3  |

TABLE 1-21

| | | | | | |
|---|---|---|---|---|---|
| 1130 | m-D1 | m-D1 | Cz3  | H    | H    |
| 1131 | m-D1 | Cz3  | m-D1 | H    | H    |
| 1132 | Cz3  | m-D1 | m-D1 | H    | H    |
| 1133 | m-D1 | m-D1 | H    | Cz3  | H    |
| 1134 | m-D1 | Cz3  | H    | m-D1 | H    |
| 1135 | Cz3  | m-D1 | H    | m-D1 | H    |
| 1136 | m-D1 | H    | m-D1 | Cz3  | H    |
| 1137 | m-D1 | H    | Cz3  | m-D1 | H    |
| 1138 | Cz3  | H    | m-D1 | m-D1 | H    |
| 1139 | H    | m-D1 | m-D1 | Cz3  | H    |
| 1140 | H    | m-D1 | Cz3  | m-D1 | H    |
| 1141 | m-D1 | m-D1 | H    | H    | Cz3  |
| 1142 | m-D1 | Cz3  | H    | H    | m-D1 |
| 1143 | Cz3  | m-D1 | H    | H    | m-D1 |
| 1144 | m-D1 | H    | m-D1 | H    | Cz3  |
| 1145 | m-D1 | H    | Cz3  | H    | m-D1 |
| 1146 | m-D1 | m-D1 | m-D1 | Cz3  | Cz3  |
| 1147 | m-D1 | m-D1 | Cz3  | m-D1 | Cz3  |
| 1148 | m-D1 | m-D1 | Cz3  | Cz3  | m-D1 |
| 1149 | m-D1 | Cz3  | m-D1 | m-D1 | Cz3  |
| 1150 | m-D1 | Cz3  | m-D1 | Cz3  | m-D1 |
| 1151 | m-D1 | m-D1 | m-D1 | Cz3  | H    |
| 1152 | m-D1 | m-D1 | Cz3  | m-D1 | H    |
| 1153 | m-D1 | Cz3  | m-D1 | m-D1 | H    |
| 1154 | Cz3  | m-D1 | m-D1 | m-D1 | H    |
| 1155 | m-D1 | m-D1 | m-D1 | H    | Cz3  |
| 1156 | m-D1 | m-D1 | Cz3  | H    | m-D1 |
| 1157 | m-D1 | Cz3  | m-D1 | H    | m-D1 |
| 1158 | Cz3  | m-D1 | m-D1 | H    | m-D1 |
| 1159 | m-D1 | m-D1 | H    | m-D1 | Cz3  |

TABLE 1-21-continued

| 1160 | m-D1 | m-D1 | H    | Cz3  | m-D1 |
| 1161 | m-D1 | m-D1 | m-D1 | m-D1 | Cz3  |
| 1162 | m-D1 | m-D1 | m-D1 | Cz3  | m-D1 |
| 1163 | m-D1 | m-D1 | Cz3  | m-D1 | m-D1 |
| 1164 | m-D2 | Cz3  | Cz3  | Cz3  | Cz3  |
| 1165 | Cz3  | m-D2 | Cz3  | Cz3  | Cz3  |
| 1166 | Cz3  | Cz3  | m-D2 | Cz3  | Cz3  |
| 1167 | m-D2 | Cz3  | Cz3  | Cz3  | H    |
| 1168 | Cz3  | m-D2 | Cz3  | Cz3  | H    |
| 1169 | Cz3  | Cz3  | m-D2 | Cz3  | H    |
| 1170 | Cz3  | Cz3  | Cz3  | m-D2 | H    |
| 1171 | m-D2 | Cz3  | Cz3  | H    | Cz3  |
| 1172 | Cz3  | m-D2 | Cz3  | H    | Cz3  |
| 1173 | Cz3  | Cz3  | m-D2 | H    | Cz3  |
| 1174 | Cz3  | Cz3  | Cz3  | H    | m-D2 |
| 1175 | m-D2 | Cz3  | H    | Cz3  | Cz3  |
| 1176 | Cz3  | m-D2 | H    | Cz3  | Cz3  |
| 1177 | m-D2 | Cz3  | H    | H    | H    |
| 1178 | Cz3  | m-D2 | Cz3  | H    | H    |
| 1179 | Cz3  | Cz3  | m-D2 | H    | H    |
| 1180 | m-D2 | Cz3  | H    | Cz3  | H    |
| 1181 | Cz3  | m-D2 | H    | Cz3  | H    |
| 1182 | Cz3  | Cz3  | H    | m-D2 | H    |
| 1183 | m-D2 | H    | Cz3  | Cz3  | H    |
| 1184 | Cz3  | H    | m-D2 | Cz3  | H    |
| 1185 | Cz3  | H    | Cz3  | m-D2 | H    |
| 1186 | H    | m-D2 | Cz3  | Cz3  | H    |
| 1187 | H    | Cz3  | m-D2 | Cz3  | H    |
| 1188 | m-D2 | Cz3  | H    | H    | Cz3  |

TABLE 1-22

| 1189 | Cz3  | m-D2 | H    | H    | Cz3  |
| 1190 | Cz3  | Cz3  | H    | H    | m-D2 |
| 1191 | m-D2 | Cz3  | H    | Cz3  | H    |
| 1192 | Cz3  | H    | m-D2 | H    | Cz3  |
| 1193 | m-D2 | Cz3  | H    | H    | H    |
| 1194 | Cz3  | m-D2 | H    | H    | H    |
| 1195 | m-D2 | H    | Cz3  | H    | H    |
| 1196 | Cz3  | H    | m-D2 | H    | H    |
| 1197 | H    | m-D2 | Cz3  | H    | H    |
| 1198 | H    | Cz3  | m-D2 | H    | H    |
| 1199 | m-D2 | H    | H    | Cz3  | H    |
| 1200 | Cz3  | H    | H    | m-D2 | H    |
| 1201 | H    | m-D2 | H    | Cz3  | H    |
| 1202 | m-D2 | H    | H    | H    | Cz3  |
| 1203 | m-D2 | m-D2 | Cz3  | Cz3  | H    |
| 1204 | m-D2 | Cz3  | m-D2 | Cz3  | H    |
| 1205 | m-D2 | Cz3  | Cz3  | m-D2 | H    |
| 1206 | m-D2 | m-D2 | Cz3  | H    | Cz3  |
| 1207 | Cz3  | m-D2 | Cz3  | m-D2 | H    |
| 1208 | Cz3  | Cz3  | m-D2 | m-D2 | H    |
| 1209 | m-D2 | m-D2 | Cz3  | H    | Cz3  |
| 1210 | m-D2 | m-D2 | Cz3  | H    | Cz3  |
| 1211 | m-D2 | Cz3  | Cz3  | H    | m-D2 |
| 1212 | Cz3  | m-D2 | m-D2 | H    | Cz3  |
| 1213 | Cz3  | m-D2 | Cz3  | H    | m-D2 |
| 1214 | Cz3  | Cz3  | m-D2 | H    | m-D2 |
| 1215 | m-D2 | m-D2 | H    | Cz3  | Cz3  |
| 1216 | m-D2 | Cz3  | H    | m-D2 | Cz3  |
| 1217 | m-D2 | Cz3  | H    | Cz3  | m-D2 |
| 1218 | Cz3  | m-D2 | H    | m-D2 | Cz3  |
| 1219 | m-D2 | m-D2 | Cz3  | H    | H    |
| 1220 | m-D2 | Cz3  | m-D2 | H    | H    |
| 1221 | Cz3  | m-D2 | m-D2 | H    | H    |
| 1222 | m-D2 | m-D2 | H    | Cz3  | H    |
| 1223 | m-D2 | Cz3  | H    | m-D2 | H    |
| 1224 | Cz3  | m-D2 | H    | m-D2 | H    |
| 1225 | m-D2 | m-D2 | H    | H    | Cz3  |
| 1226 | m-D2 | H    | Cz3  | m-D2 | H    |
| 1227 | Cz3  | H    | m-D2 | m-D2 | H    |
| 1228 | H    | m-D2 | m-D2 | Cz3  | H    |
| 1229 | H    | m-D2 | Cz3  | m-D2 | H    |
| 1230 | m-D2 | m-D2 | H    | H    | Cz3  |
| 1231 | m-D2 | Cz3  | H    | H    | m-D2 |
| 1232 | Cz3  | m-D2 | H    | H    | m-D2 |
| 1233 | m-D2 | H    | m-D2 | H    | Cz3  |

TABLE 1-22-continued

| 1234 | m-D2 | H    | Cz3  | H    | m-D2 |
| 1235 | m-D2 | m-D2 | m-D2 | Cz3  | Cz3  |
| 1236 | m-D2 | m-D2 | Cz3  | m-D2 | Cz3  |
| 1237 | m-D2 | m-D2 | Cz3  | Cz3  | m-D2 |
| 1238 | m-D2 | Cz3  | m-D2 | m-D2 | Cz3  |
| 1239 | m-D2 | Cz3  | m-D2 | Cz3  | m-D2 |
| 1240 | m-D2 | m-D2 | m-D2 | Cz3  | H    |
| 1241 | m-D2 | m-D2 | m-D2 | H    | Cz3  |
| 1242 | m-D2 | Cz3  | m-D2 | Cz3  | H    |
| 1243 | Cz3  | m-D2 | m-D2 | m-D2 | Cz3  |
| 1244 | m-D2 | m-D2 | m-D2 | H    | Cz3  |
| 1245 | m-D2 | m-D2 | Cz3  | H    | m-D2 |
| 1246 | m-D2 | m-D2 | Cz3  | H    | m-D2 |
| 1247 | Cz3  | m-D2 | m-D2 | H    | m-D2 |

TABLE 1-23

| 1248 | m-D2 | m-D2 | H    | m-D2 | Cz3  |
| 1249 | m-D2 | m-D2 | H    | Cz3  | m-D2 |
| 1250 | m-D2 | m-D2 | m-D2 | m-D2 | Cz3  |
| 1251 | m-D2 | m-D2 | m-D2 | Cz3  | m-D2 |
| 1252 | m-D2 | m-D2 | Cz3  | m-D2 | m-D2 |
| 1253 | m-D3 | Cz3  | Cz3  | Cz3  | Cz3  |
| 1254 | Cz3  | m-D3 | Cz3  | Cz3  | Cz3  |
| 1255 | Cz3  | Cz3  | m-D3 | Cz3  | Cz3  |
| 1256 | m-D3 | Cz3  | Cz3  | Cz3  | H    |
| 1257 | Cz3  | m-D3 | Cz3  | Cz3  | H    |
| 1258 | Cz3  | Cz3  | m-D3 | Cz3  | H    |
| 1259 | Cz3  | Cz3  | Cz3  | m-D3 | H    |
| 1260 | m-D3 | Cz3  | Cz3  | H    | Cz3  |
| 1261 | Cz3  | m-D3 | Cz3  | H    | Cz3  |
| 1262 | Cz3  | Cz3  | m-D3 | H    | Cz3  |
| 1263 | Cz3  | Cz3  | Cz3  | H    | m-D3 |
| 1264 | m-D3 | Cz3  | H    | Cz3  | Cz3  |
| 1265 | Cz3  | m-D3 | H    | Cz3  | Cz3  |
| 1266 | m-D3 | Cz3  | Cz3  | H    | H    |
| 1267 | Cz3  | m-D3 | Cz3  | H    | H    |
| 1268 | Cz3  | Cz3  | m-D3 | H    | H    |
| 1269 | m-D3 | Cz3  | H    | Cz3  | H    |
| 1270 | Cz3  | m-D3 | H    | Cz3  | H    |
| 1271 | Cz3  | Cz3  | H    | m-D3 | H    |
| 1272 | m-D3 | H    | Cz3  | Cz3  | H    |
| 1273 | Cz3  | H    | m-D3 | Cz3  | H    |
| 1274 | Cz3  | H    | Cz3  | m-D3 | H    |
| 1275 | H    | m-D3 | Cz3  | Cz3  | H    |
| 1276 | H    | Cz3  | m-D3 | Cz3  | H    |
| 1277 | m-D3 | Cz3  | H    | H    | Cz3  |
| 1278 | Cz3  | m-D3 | H    | H    | Cz3  |
| 1279 | Cz3  | Cz3  | H    | H    | m-D3 |
| 1280 | m-D3 | H    | Cz3  | H    | Cz3  |
| 1281 | Cz3  | H    | m-D3 | H    | Cz3  |
| 1282 | Cz3  | m-D3 | H    | H    | H    |
| 1283 | Cz3  | Cz3  | H    | H    | H    |
| 1284 | m-D3 | H    | Cz3  | H    | H    |
| 1285 | Cz3  | H    | m-D3 | H    | H    |
| 1286 | H    | m-D3 | Cz3  | H    | H    |
| 1287 | H    | Cz3  | m-D3 | H    | H    |
| 1288 | m-D3 | H    | H    | Cz3  | H    |
| 1289 | Cz3  | H    | H    | m-D3 | H    |
| 1290 | H    | m-D3 | H    | Cz3  | H    |
| 1291 | m-D3 | H    | H    | H    | Cz3  |
| 1292 | m-D3 | m-D3 | Cz3  | Cz3  | H    |
| 1293 | m-D3 | Cz3  | m-D3 | Cz3  | H    |
| 1294 | m-D3 | Cz3  | Cz3  | m-D3 | H    |
| 1295 | Cz3  | m-D3 | m-D3 | Cz3  | H    |
| 1296 | Cz3  | m-D3 | Cz3  | m-D3 | H    |
| 1297 | Cz3  | Cz3  | m-D3 | m-D3 | H    |
| 1298 | m-D3 | m-D3 | Cz3  | H    | Cz3  |
| 1299 | m-D3 | Cz3  | m-D3 | H    | Cz3  |
| 1300 | m-D3 | Cz3  | Cz3  | H    | m-D3 |
| 1301 | Cz3  | m-D3 | m-D3 | H    | Cz3  |
| 1302 | Cz3  | m-D3 | Cz3  | H    | m-D3 |
| 1303 | Cz3  | Cz3  | m-D3 | H    | m-D3 |
| 1304 | m-D3 | m-D3 | H    | Cz3  | Cz3  |
| 1305 | m-D3 | Cz3  | H    | m-D3 | Cz3  |
| 1306 | m-D3 | Cz3  | H    | Cz3  | m-D3 |

TABLE 1-24

| No | R¹ | R² | R³ | R⁴ | R⁵ |
|---|---|---|---|---|---|
| 1307 | Cz3 | m-D3 | H | m-D3 | Cz3 |
| 1308 | m-D3 | m-D3 | Cz3 | H | H |
| 1309 | m-D3 | Cz3 | m-D3 | H | H |
| 1310 | Cz3 | m-D3 | m-D3 | H | H |
| 1311 | m-D3 | m-D3 | H | Cz3 | H |
| 1312 | m-D3 | Cz3 | H | m-D3 | H |
| 1313 | Cz3 | m-D3 | H | m-D3 | H |
| 1314 | m-D3 | H | m-D3 | Cz3 | H |
| 1315 | m-D3 | H | Cz3 | m-D3 | H |
| 1316 | Cz3 | H | m-D3 | m-D3 | H |
| 1317 | H | m-D3 | m-D3 | Cz3 | H |
| 1318 | H | m-D3 | Cz3 | m-D3 | H |
| 1319 | m-D3 | m-D3 | H | H | Cz3 |
| 1320 | m-D3 | Cz3 | H | H | m-D3 |
| 1321 | Cz3 | m-D3 | H | H | m-D3 |
| 1322 | m-D3 | H | m-D3 | H | Cz3 |
| 1323 | m-D3 | H | Cz3 | H | m-D3 |
| 1324 | m-D3 | m-D3 | m-D3 | Cz3 | Cz3 |
| 1325 | m-D3 | m-D3 | Cz3 | m-D3 | Cz3 |
| 1326 | m-D3 | m-D3 | Cz3 | Cz3 | m-D3 |
| 1327 | m-D3 | Cz3 | m-D3 | m-D3 | Cz3 |
| 1328 | m-D3 | Cz3 | m-D3 | Cz3 | m-D3 |
| 1329 | m-D3 | m-D3 | m-D3 | Cz3 | H |
| 1330 | m-D3 | m-D3 | Cz3 | m-D3 | H |
| 1331 | m-D3 | Cz3 | m-D3 | m-D3 | H |
| 1332 | Cz3 | m-D3 | m-D3 | m-D3 | H |
| 1333 | m-D3 | m-D3 | m-D3 | H | Cz3 |
| 1334 | m-D3 | m-D3 | Cz3 | H | m-D3 |
| 1335 | m-D3 | Cz3 | m-D3 | H | m-D3 |
| 1336 | Cz3 | m-D3 | m-D3 | H | m-D3 |
| 1337 | m-D3 | m-D3 | H | m-D3 | Cz3 |
| 1338 | m-D3 | m-D3 | H | Cz3 | m-D3 |
| 1339 | m-D3 | m-D3 | m-D3 | m-D3 | Cz3 |
| 1340 | m-D3 | m-D3 | m-D3 | Cz3 | m-D3 |
| 1341 | m-D3 | m-D3 | Cz3 | m-D3 | m-D3 |

TABLE 1-25

| No | R¹ | R² | R³ | R⁴ | R⁵ |
|---|---|---|---|---|---|
| 1342 | Cz4 | Cz4 | m-D1 | Cz4 | Cz4 |
| 1343 | m-D1 | Cz4 | Cz4 | Cz4 | H |
| 1344 | Cz4 | Cz4 | Cz4 | m-D1 | H |
| 1345 | m-D1 | Cz4 | Cz4 | H | Cz4 |
| 1346 | Cz4 | Cz4 | m-D1 | H | Cz4 |
| 1347 | Cz4 | m-D1 | H | Cz4 | Cz4 |
| 1348 | Cz4 | m-D1 | Cz4 | H | H |
| 1349 | Cz4 | Cz4 | m-D1 | H | H |
| 1350 | H | m-D1 | Cz4 | Cz4 | H |
| 1351 | H | Cz4 | m-D1 | Cz4 | H |
| 1352 | m-D1 | H | Cz4 | H | Cz4 |
| 1353 | Cz4 | H | m-D1 | H | Cz4 |
| 1354 | m-D1 | Cz4 | H | H | H |
| 1355 | H | m-D1 | H | Cz4 | H |
| 1356 | m-D1 | m-D1 | Cz4 | H | Cz4 |
| 1357 | m-D1 | Cz4 | m-D1 | H | Cz4 |
| 1358 | Cz4 | m-D1 | m-D1 | H | Cz4 |
| 1359 | m-D1 | m-D1 | H | Cz4 | Cz4 |
| 1360 | Cz4 | m-D1 | H | m-D1 | Cz4 |
| 1361 | m-D1 | Cz4 | m-D1 | H | H |
| 1362 | H | m-D1 | m-D1 | Cz4 | H |
| 1363 | H | m-D1 | Cz4 | m-D1 | H |
| 1364 | m-D1 | H | m-D1 | H | Cz4 |
| 1365 | m-D1 | H | Cz4 | H | m-D1 |
| 1366 | m-D1 | Cz4 | m-D1 | Cz4 | m-D1 |
| 1367 | m-D1 | m-D1 | m-D1 | Cz4 | H |
| 1368 | m-D1 | m-D1 | Cz4 | m-D1 | H |
| 1369 | m-D1 | m-D1 | m-D1 | H | Cz4 |
| 1370 | m-D1 | m-D1 | H | m-D1 | Cz4 |
| 1371 | m-D1 | m-D1 | H | Cz4 | m-D1 |
| 1372 | m-D1 | m-D1 | m-D1 | m-D1 | Cz4 |
| 1373 | Cz4 | Cz4 | m-D2 | Cz4 | Cz4 |
| 1374 | m-D2 | Cz4 | Cz4 | Cz4 | H |
| 1375 | Cz4 | Cz4 | Cz4 | m-D2 | H |
| 1376 | m-D2 | Cz4 | Cz4 | H | Cz4 |
| 1377 | Cz4 | Cz4 | m-D2 | H | Cz4 |
| 1378 | Cz4 | m-D2 | H | Cz4 | Cz4 |
| 1379 | Cz4 | m-D2 | Cz4 | H | H |
| 1380 | Cz4 | Cz4 | m-D2 | H | H |
| 1381 | H | m-D2 | Cz4 | Cz4 | H |
| 1382 | H | Cz4 | m-D2 | Cz4 | H |
| 1383 | m-D2 | H | Cz4 | H | Cz4 |
| 1384 | Cz4 | H | m-D2 | H | Cz4 |
| 1385 | m-D2 | Cz4 | H | H | H |
| 1386 | H | m-D2 | H | Cz4 | H |
| 1387 | m-D2 | m-D2 | Cz4 | H | Cz4 |
| 1388 | m-D2 | Cz4 | m-D2 | H | Cz4 |
| 1389 | Cz4 | m-D2 | m-D2 | H | Cz4 |
| 1390 | m-D2 | m-D2 | H | Cz4 | Cz4 |
| 1391 | Cz4 | m-D2 | H | m-D2 | Cz4 |
| 1392 | m-D2 | Cz4 | m-D2 | H | H |
| 1393 | H | m-D2 | m-D2 | Cz4 | H |
| 1394 | H | m-D2 | Cz4 | m-D2 | H |
| 1395 | m-D2 | H | m-D2 | H | Cz4 |
| 1396 | m-D2 | H | Cz4 | H | m-D2 |
| 1397 | m-D2 | Cz4 | m-D2 | Cz4 | m-D2 |
| 1398 | m-D2 | m-D2 | m-D2 | Cz4 | H |
| 1399 | m-D2 | m-D2 | Cz4 | m-D2 | H |

TABLE 1-26

| No | R¹ | R² | R³ | R⁴ | R⁵ |
|---|---|---|---|---|---|
| 1400 | m-D2 | m-D2 | m-D2 | H | Cz4 |
| 1401 | m-D2 | m-D2 | H | m-D2 | Cz4 |
| 1402 | m-D2 | m-D2 | H | m-D2 | m-D2 |
| 1403 | m-D2 | m-D2 | m-D2 | m-D2 | Cz4 |
| 1404 | Cz4 | Cz4 | m-D3 | Cz4 | Cz4 |
| 1405 | m-D3 | Cz4 | Cz4 | Cz4 | H |
| 1406 | Cz4 | Cz4 | Cz4 | m-D3 | H |
| 1407 | m-D3 | Cz4 | Cz4 | H | Cz4 |
| 1408 | Cz4 | Cz4 | m-D3 | H | Cz4 |
| 1409 | Cz4 | m-D3 | H | Cz4 | Cz4 |
| 1410 | Cz4 | m-D3 | Cz4 | H | H |
| 1411 | Cz4 | Cz4 | m-D3 | H | H |
| 1412 | H | m-D3 | Cz4 | Cz4 | H |
| 1413 | H | Cz4 | m-D3 | Cz4 | H |
| 1414 | m-D3 | H | Cz4 | H | Cz4 |
| 1415 | Cz4 | H | m-D3 | H | Cz4 |
| 1416 | m-D3 | Cz4 | H | H | H |
| 1417 | H | m-D3 | H | Cz4 | H |
| 1418 | m-D3 | m-D3 | Cz4 | H | Cz4 |
| 1419 | m-D3 | Cz4 | m-D3 | H | Cz4 |
| 1420 | Cz4 | m-D3 | m-D3 | H | Cz4 |
| 1421 | m-D3 | m-D3 | H | Cz4 | Cz4 |
| 1422 | Cz4 | m-D3 | H | m-D3 | Cz4 |
| 1423 | m-D3 | Cz4 | m-D3 | H | H |
| 1424 | H | m-D3 | m-D3 | Cz4 | H |
| 1425 | H | m-D3 | Cz4 | m-D3 | H |
| 1426 | m-D3 | H | m-D3 | H | Cz4 |
| 1427 | m-D3 | H | Cz4 | H | m-D3 |
| 1428 | m-D3 | Cz4 | m-D3 | Cz4 | m-D3 |
| 1429 | m-D3 | m-D3 | m-D3 | Cz4 | H |
| 1430 | m-D3 | m-D3 | Cz4 | m-D3 | H |
| 1431 | m-D3 | m-D3 | m-D3 | H | Cz4 |
| 1432 | m-D3 | m-D3 | H | m-D3 | Cz4 |
| 1433 | m-D3 | m-D3 | H | Cz4 | m-D3 |
| 1434 | m-D3 | m-D3 | m-D3 | m-D3 | Cz4 |
| 1435 | Cz5 | Cz5 | m-D1 | Cz5 | Cz5 |
| 1436 | m-D1 | Cz5 | Cz5 | Cz5 | H |
| 1437 | Cz5 | Cz5 | Cz5 | m-D1 | H |
| 1438 | m-D1 | Cz5 | Cz5 | H | Cz5 |
| 1439 | Cz5 | Cz5 | m-D1 | H | Cz5 |
| 1440 | Cz5 | m-D1 | H | Cz5 | Cz5 |
| 1441 | Cz5 | m-D1 | Cz5 | H | H |
| 1442 | Cz5 | Cz5 | m-D1 | H | H |
| 1443 | H | m-D1 | Cz5 | Cz5 | H |
| 1444 | H | Cz5 | m-D1 | Cz5 | H |
| 1445 | m-D1 | H | Cz5 | H | Cz5 |
| 1446 | Cz5 | H | m-D1 | H | Cz5 |
| 1447 | m-D1 | Cz5 | H | H | H |
| 1448 | H | m-D1 | H | Cz5 | H |
| 1449 | m-D1 | m-D1 | Cz5 | H | Cz5 |
| 1450 | m-D1 | Cz5 | m-D1 | H | Cz5 |

TABLE 1-26-continued

| | | | | | |
|---|---|---|---|---|---|
| 1451 | Cz5 | m-D1 | m-D1 | H | Cz5 |
| 1452 | m-D1 | m-D1 | H | Cz5 | Cz5 |
| 1453 | Cz5 | m-D1 | H | m-D1 | Cz5 |
| 1454 | m-D1 | Cz5 | m-D1 | H | H |
| 1455 | H | m-D1 | m-D1 | Cz5 | H |
| 1456 | H | m-D1 | Cz5 | m-D1 | H |
| 1457 | m-D1 | H | m-D1 | H | Cz5 |
| 1458 | m-D1 | H | Cz5 | H | m-D1 |

TABLE 1-27

| | | | | | |
|---|---|---|---|---|---|
| 1459 | m-D1 | Cz5 | m-D1 | Cz5 | m-D1 |
| 1460 | m-D1 | m-D1 | m-D1 | Cz5 | H |
| 1461 | m-D1 | m-D1 | Cz5 | m-D1 | H |
| 1462 | m-D1 | m-D1 | m-D1 | H | Cz5 |
| 1463 | m-D1 | m-D1 | H | m-D1 | Cz5 |
| 1464 | m-D1 | m-D1 | H | Cz5 | m-D1 |
| 1465 | m-D1 | m-D1 | m-D1 | m-D1 | Cz5 |
| 1466 | Cz5 | Cz5 | m-D2 | Cz5 | Cz5 |
| 1467 | m-D2 | Cz5 | Cz5 | Cz5 | H |
| 1468 | Cz5 | Cz5 | Cz5 | m-D2 | H |
| 1469 | m-D2 | Cz5 | Cz5 | H | Cz5 |
| 1470 | Cz5 | Cz5 | m-D2 | H | Cz5 |
| 1471 | Cz5 | m-D2 | H | Cz5 | Cz5 |
| 1472 | Cz5 | m-D2 | Cz5 | H | H |
| 1473 | Cz5 | Cz5 | m-D2 | H | H |
| 1474 | H | m-D2 | Cz5 | Cz5 | H |
| 1475 | H | Cz5 | m-D2 | Cz5 | H |
| 1476 | m-D2 | H | Cz5 | H | Cz5 |
| 1477 | Cz5 | H | m-D2 | H | Cz5 |
| 1478 | m-D2 | Cz5 | H | H | H |
| 1479 | H | m-D2 | H | Cz5 | H |
| 1480 | m-D2 | m-D2 | Cz5 | H | Cz5 |
| 1481 | m-D2 | Cz5 | m-D2 | H | Cz5 |
| 1482 | Cz5 | m-D2 | m-D2 | H | Cz5 |
| 1483 | m-D2 | m-D2 | H | Cz5 | Cz5 |
| 1484 | Cz5 | m-D2 | H | m-D2 | Cz5 |
| 1485 | m-D2 | Cz5 | m-D2 | H | H |
| 1486 | H | m-D2 | m-D2 | Cz5 | H |
| 1487 | H | m-D2 | Cz5 | m-D2 | H |
| 1488 | m-D2 | H | m-D2 | H | Cz5 |
| 1489 | m-D2 | H | Cz5 | H | m-D2 |
| 1490 | m-D2 | Cz5 | m-D2 | Cz5 | m-D2 |
| 1491 | m-D2 | m-D2 | m-D2 | Cz5 | H |
| 1492 | m-D2 | m-D2 | Cz5 | m-D2 | H |
| 1493 | m-D2 | m-D2 | m-D2 | H | Cz5 |
| 1494 | m-D2 | m-D2 | H | m-D2 | Cz5 |
| 1495 | m-D2 | m-D2 | H | Cz5 | m-D2 |
| 1496 | m-D2 | m-D2 | m-D2 | m-D2 | Cz5 |
| 1497 | Cz5 | Cz5 | m-D3 | Cz5 | Cz5 |
| 1498 | m-D3 | Cz5 | Cz5 | Cz5 | H |
| 1499 | Cz5 | Cz5 | Cz5 | m-D3 | H |
| 1500 | m-D3 | Cz5 | Cz5 | H | Cz5 |
| 1501 | Cz5 | Cz5 | m-D3 | H | Cz5 |
| 1502 | Cz5 | m-D3 | H | Cz5 | Cz5 |
| 1503 | Cz5 | m-D3 | Cz5 | H | H |
| 1504 | Cz5 | Cz5 | m-D3 | H | H |
| 1505 | H | m-D3 | Cz5 | Cz5 | H |
| 1506 | H | Cz5 | m-D3 | Cz5 | H |
| 1507 | m-D3 | H | Cz5 | H | Cz5 |
| 1508 | Cz5 | H | m-D3 | H | Cz5 |
| 1509 | m-D3 | Cz5 | H | H | H |
| 1510 | H | m-D3 | H | Cz5 | H |
| 1511 | m-D3 | m-D3 | Cz5 | H | Cz5 |
| 1512 | m-D3 | Cz5 | m-D3 | H | Cz5 |
| 1513 | Cz5 | m-D3 | m-D3 | H | Cz5 |
| 1514 | m-D3 | m-D3 | H | Cz5 | Cz5 |
| 1515 | Cz5 | m-D3 | H | m-D3 | Cz5 |
| 1516 | m-D3 | Cz5 | m-D3 | H | H |
| 1517 | H | m-D3 | m-D3 | Cz5 | H |

TABLE 1-28

| | | | | | |
|---|---|---|---|---|---|
| 1518 | H | m-D3 | Cz5 | m-D3 | H |
| 1519 | m-D3 | H | m-D3 | H | Cz5 |
| 1520 | m-D3 | H | Cz5 | H | m-D3 |
| 1521 | m-D3 | Cz5 | m-D3 | Cz5 | m-D3 |
| 1522 | m-D3 | m-D3 | m-D3 | Cz5 | H |
| 1523 | m-D3 | m-D3 | Cz5 | m-D3 | H |
| 1524 | m-D3 | m-D3 | m-D3 | H | Cz5 |
| 1525 | m-D3 | m-D3 | H | m-D3 | Cz5 |
| 1526 | m-D3 | m-D3 | H | Cz5 | m-D3 |
| 1527 | m-D3 | m-D3 | m-D3 | m-D3 | Cz5 |
| 1528 | Cz6 | Cz6 | m-D1 | Cz6 | Cz6 |
| 1529 | m-D1 | Cz6 | Cz6 | Cz6 | H |
| 1530 | Cz6 | Cz6 | Cz6 | m-D1 | H |
| 1531 | m-D1 | Cz6 | Cz6 | H | Cz6 |
| 1532 | Cz6 | Cz6 | m-D1 | H | Cz6 |
| 1533 | Cz6 | m-D1 | H | Cz6 | Cz6 |
| 1534 | Cz6 | m-D1 | Cz6 | H | H |
| 1535 | Cz6 | Cz6 | m-D1 | H | H |
| 1536 | H | m-D1 | Cz6 | Cz6 | H |
| 1537 | H | Cz6 | m-D1 | Cz6 | H |
| 1538 | m-D1 | H | Cz6 | H | Cz6 |
| 1539 | Cz6 | H | m-D1 | H | Cz6 |
| 1540 | m-D1 | Cz6 | H | H | H |
| 1541 | H | m-D1 | H | Cz6 | H |
| 1542 | m-D1 | m-D1 | Cz6 | H | Cz6 |
| 1543 | m-D1 | Cz6 | m-D1 | H | Cz6 |
| 1544 | Cz6 | m-D1 | m-D1 | H | Cz6 |
| 1545 | m-D1 | m-D1 | H | Cz6 | Cz6 |
| 1546 | Cz6 | m-D1 | H | m-D1 | Cz6 |
| 1547 | m-D1 | Cz6 | m-D1 | H | H |
| 1548 | H | m-D1 | m-D1 | Cz6 | H |
| 1549 | H | m-D1 | Cz6 | m-D1 | H |
| 1550 | m-D1 | H | m-D1 | H | Cz6 |
| 1551 | m-D1 | H | Cz6 | H | m-D1 |
| 1552 | m-D1 | Cz6 | m-D1 | Cz6 | m-D1 |
| 1553 | m-D1 | m-D1 | m-D1 | Cz6 | H |
| 1554 | m-D1 | m-D1 | Cz6 | m-D1 | H |
| 1555 | m-D1 | m-D1 | m-D1 | H | Cz6 |
| 1556 | m-D1 | m-D1 | H | m-D1 | Cz6 |
| 1557 | m-D1 | m-D1 | H | Cz6 | m-D1 |
| 1558 | m-D1 | m-D1 | m-D1 | m-D1 | Cz6 |
| 1559 | Cz6 | Cz6 | m-D2 | Cz6 | Cz6 |
| 1560 | m-D2 | Cz6 | Cz6 | Cz6 | H |
| 1561 | Cz6 | Cz6 | Cz6 | m-D2 | H |
| 1562 | m-D2 | Cz6 | Cz6 | H | Cz6 |
| 1563 | Cz6 | Cz6 | m-D2 | H | Cz6 |
| 1564 | Cz6 | m-D2 | H | Cz6 | Cz6 |
| 1565 | Cz6 | m-D2 | Cz6 | H | H |
| 1566 | Cz6 | Cz6 | m-D2 | H | H |
| 1567 | H | m-D2 | Cz6 | Cz6 | H |
| 1568 | H | Cz6 | m-D2 | Cz6 | H |
| 1569 | m-D2 | H | Cz6 | H | Cz6 |
| 1570 | Cz6 | H | m-D2 | H | Cz6 |
| 1571 | m-D2 | Cz6 | H | H | H |
| 1572 | H | m-D2 | H | Cz6 | H |
| 1573 | m-D2 | m-D2 | Cz6 | H | Cz6 |
| 1574 | m-D2 | Cz6 | m-D2 | H | Cz6 |
| 1575 | Cz6 | m-D2 | m-D2 | H | Cz6 |
| 1576 | m-D2 | m-D2 | H | Cz6 | Cz6 |

TABLE 1-29

| | | | | | |
|---|---|---|---|---|---|
| 1577 | Cz6 | m-D2 | H | m-D2 | Cz6 |
| 1578 | m-D2 | Cz6 | m-D2 | H | H |
| 1579 | H | m-D2 | m-D2 | Cz6 | H |
| 1580 | H | m-D2 | Cz6 | m-D2 | H |
| 1581 | m-D2 | H | m-D2 | H | Cz6 |
| 1582 | m-D2 | H | Cz6 | H | m-D2 |
| 1583 | m-D2 | Cz6 | m-D2 | Cz6 | m-D2 |
| 1584 | m-D2 | m-D2 | m-D2 | Cz6 | H |
| 1585 | m-D2 | m-D2 | Cz6 | m-D2 | H |
| 1586 | m-D2 | m-D2 | m-D2 | H | Cz6 |
| 1587 | m-D2 | m-D2 | H | m-D2 | Cz6 |
| 1588 | m-D2 | m-D2 | H | Cz6 | m-D2 |
| 1589 | m-D2 | m-D2 | m-D2 | m-D2 | Cz6 |
| 1590 | Cz6 | Cz6 | m-D3 | Cz6 | Cz6 |
| 1591 | m-D3 | Cz6 | Cz6 | Cz6 | H |
| 1592 | Cz6 | Cz6 | Cz6 | m-D3 | H |
| 1593 | m-D3 | Cz6 | Cz6 | H | Cz6 |

TABLE 1-29-continued

| | | | | | |
|---|---|---|---|---|---|
| 1594 | Cz6 | Cz6 | m-D3 | H | Cz6 |
| 1595 | Cz6 | m-D3 | H | Cz6 | Cz6 |
| 1596 | Cz6 | m-D3 | Cz6 | H | H |
| 1597 | Cz6 | Cz6 | m-D3 | H | H |
| 1598 | H | m-D3 | Cz6 | Cz6 | H |
| 1599 | H | Cz6 | m-D3 | Cz6 | H |
| 1600 | m-D3 | H | Cz6 | H | Cz6 |
| 1601 | Cz6 | H | m-D3 | H | Cz6 |
| 1602 | m-D3 | Cz6 | H | H | H |
| 1603 | H | m-D3 | H | Cz6 | H |
| 1604 | m-D3 | m-D3 | Cz6 | H | Cz6 |
| 1605 | m-D3 | Cz6 | m-D3 | H | Cz6 |
| 1606 | Cz6 | m-D3 | m-D3 | H | Cz6 |
| 1607 | m-D3 | m-D3 | H | Cz6 | Cz6 |
| 1608 | Cz6 | m-D3 | H | m-D3 | Cz6 |
| 1609 | m-D3 | Cz6 | m-D3 | H | H |
| 1610 | H | m-D3 | Cz6 | m-D3 | Cz6 |
| 1611 | H | m-D3 | Cz6 | m-D3 | H |
| 1612 | m-D3 | H | m-D3 | H | Cz6 |
| 1613 | m-D3 | H | Cz6 | H | m-D3 |
| 1614 | m-D3 | Cz6 | m-D3 | Cz6 | m-D3 |
| 1615 | m-D3 | m-D3 | m-D3 | Cz6 | H |
| 1616 | m-D3 | m-D3 | Cz6 | m-D3 | H |
| 1617 | m-D3 | m-D3 | m-D3 | H | Cz6 |
| 1618 | m-D3 | m-D3 | H | m-D3 | Cz6 |
| 1619 | m-D3 | m-D3 | H | Cz6 | m-D3 |
| 1620 | m-D3 | m-D3 | m-D3 | m-D3 | Cz6 |
| 1621 | Cz7 | Cz7 | m-D1 | Cz7 | Cz7 |
| 1622 | m-D1 | Cz7 | Cz7 | Cz7 | H |
| 1623 | Cz7 | Cz7 | Cz7 | m-D1 | H |
| 1624 | m-D1 | Cz7 | Cz7 | H | Cz7 |
| 1625 | Cz7 | Cz7 | m-D1 | H | Cz7 |
| 1626 | Cz7 | m-D1 | Cz7 | Cz7 | Cz7 |
| 1627 | Cz7 | Cz7 | Cz7 | H | H |
| 1628 | Cz7 | Cz7 | m-D1 | H | H |
| 1629 | H | m-D1 | Cz7 | Cz7 | H |
| 1630 | H | Cz7 | m-D1 | Cz7 | H |
| 1631 | m-D1 | H | Cz7 | H | Cz7 |
| 1632 | Cz7 | H | m-D1 | H | Cz7 |
| 1633 | m-D1 | Cz7 | H | H | H |
| 1634 | H | m-D1 | H | Cz7 | H |
| 1635 | m-D1 | m-D1 | Cz7 | H | Cz7 |

TABLE 1-30

| | | | | | |
|---|---|---|---|---|---|
| 1636 | m-D1 | Cz7 | m-D1 | H | Cz7 |
| 1637 | Cz7 | m-D1 | m-D1 | H | Cz7 |
| 1638 | m-D1 | m-D1 | m-D1 | H | Cz7 |
| 1639 | Cz7 | m-D1 | H | m-D1 | Cz7 |
| 1640 | m-D1 | Cz7 | m-D1 | H | H |
| 1641 | H | m-D1 | m-D1 | Cz7 | H |
| 1642 | H | m-D1 | Cz7 | m-D1 | H |
| 1643 | m-D1 | H | m-D1 | H | Cz7 |
| 1644 | m-D1 | H | Cz7 | H | m-D1 |
| 1645 | m-D1 | Cz7 | m-D1 | Cz7 | m-D1 |
| 1646 | m-D1 | m-D1 | m-D1 | Cz7 | H |
| 1647 | m-D1 | m-D1 | Cz7 | m-D1 | H |
| 1648 | m-D1 | m-D1 | m-D1 | H | Cz7 |
| 1649 | m-D1 | m-D1 | H | m-D1 | Cz7 |
| 1650 | m-D1 | m-D1 | H | Cz7 | m-D1 |
| 1651 | m-D1 | m-D1 | m-D1 | m-D1 | Cz7 |
| 1652 | Cz7 | Cz7 | m-D2 | Cz7 | Cz7 |
| 1653 | m-D2 | Cz7 | Cz7 | Cz7 | H |
| 1654 | Cz7 | Cz7 | Cz7 | m-D2 | H |
| 1655 | m-D2 | Cz7 | Cz7 | H | Cz7 |
| 1656 | Cz7 | Cz7 | m-D2 | H | Cz7 |
| 1657 | Cz7 | m-D2 | H | Cz7 | Cz7 |
| 1658 | Cz7 | m-D2 | Cz7 | H | H |
| 1659 | Cz7 | Cz7 | m-D2 | H | H |
| 1660 | H | m-D2 | Cz7 | Cz7 | H |
| 1661 | H | Cz7 | m-D2 | Cz7 | H |
| 1662 | m-D2 | H | Cz7 | H | Cz7 |
| 1663 | Cz7 | H | m-D2 | H | Cz7 |
| 1664 | m-D2 | Cz7 | H | H | H |
| 1665 | H | m-D2 | Cz7 | H | H |
| 1666 | m-D2 | m-D2 | Cz7 | H | Cz7 |
| 1667 | m-D2 | Cz7 | m-D2 | H | Cz7 |

TABLE 1-30-continued

| | | | | | |
|---|---|---|---|---|---|
| 1668 | Cz7 | m-D2 | m-D2 | H | Cz7 |
| 1669 | m-D2 | m-D2 | H | Cz7 | Cz7 |
| 1670 | Cz7 | m-D2 | H | m-D2 | Cz7 |
| 1671 | m-D2 | Cz7 | m-D2 | H | H |
| 1672 | H | m-D2 | m-D2 | Cz7 | H |
| 1673 | H | m-D2 | Cz7 | m-D2 | H |
| 1674 | m-D2 | H | m-D2 | H | Cz7 |
| 1675 | m-D2 | H | Cz7 | H | m-D2 |
| 1676 | m-D2 | Cz7 | m-D2 | Cz7 | m-D2 |
| 1677 | m-D2 | m-D2 | m-D2 | Cz7 | H |
| 1678 | m-D2 | m-D2 | Cz7 | m-D2 | H |
| 1679 | m-D2 | m-D2 | m-D2 | H | Cz7 |
| 1680 | m-D2 | m-D2 | H | m-D2 | Cz7 |
| 1681 | m-D2 | m-D2 | H | Cz7 | m-D2 |
| 1682 | m-D2 | m-D2 | m-D2 | m-D2 | Cz7 |
| 1683 | Cz7 | Cz7 | m-D3 | Cz7 | Cz7 |
| 1684 | Cz7 | Cz7 | Cz7 | Cz7 | H |
| 1685 | Cz7 | Cz7 | Cz7 | m-D3 | H |
| 1686 | m-D3 | Cz7 | Cz7 | H | Cz7 |
| 1687 | Cz7 | Cz7 | m-D3 | H | Cz7 |
| 1688 | Cz7 | m-D3 | H | Cz7 | Cz7 |
| 1689 | Cz7 | m-D3 | Cz7 | H | H |
| 1690 | Cz7 | Cz7 | m-D3 | H | H |
| 1691 | H | m-D3 | Cz7 | Cz7 | H |
| 1692 | H | Cz7 | m-D3 | Cz7 | H |
| 1693 | m-D3 | H | Cz7 | H | Cz7 |
| 1694 | Cz7 | H | m-D3 | H | Cz7 |

TABLE 1-31

| | | | | | |
|---|---|---|---|---|---|
| 1695 | m-D3 | Cz7 | H | H | H |
| 1696 | H | m-D3 | H | Cz7 | H |
| 1697 | m-D3 | m-D3 | Cz7 | H | Cz7 |
| 1698 | m-D3 | Cz7 | Cz7 | H | Cz7 |
| 1699 | Cz7 | m-D3 | m-D3 | H | Cz7 |
| 1700 | m-D3 | m-D3 | H | Cz7 | Cz7 |
| 1701 | Cz7 | m-D3 | H | m-D3 | Cz7 |
| 1702 | m-D3 | Cz7 | m-D3 | H | H |
| 1703 | H | m-D3 | m-D3 | Cz7 | H |
| 1704 | H | m-D3 | Cz7 | m-D3 | H |
| 1705 | m-D3 | H | m-D3 | H | Cz7 |
| 1706 | m-D3 | H | Cz7 | H | m-D3 |
| 1707 | m-D3 | Cz7 | m-D3 | Cz7 | m-D3 |
| 1708 | m-D3 | m-D3 | m-D3 | Cz7 | H |
| 1709 | m-D3 | m-D3 | Cz7 | m-D3 | H |
| 1710 | m-D3 | m-D3 | m-D3 | H | Cz7 |
| 1711 | m-D3 | m-D3 | H | m-D3 | Cz7 |
| 1712 | m-D3 | m-D3 | H | Cz7 | m-D3 |
| 1713 | m-D3 | m-D3 | m-D3 | m-D3 | Cz7 |
| 1714 | Cz8 | Cz8 | m-D1 | Cz8 | Cz8 |
| 1715 | m-D1 | Cz8 | Cz8 | Cz8 | H |
| 1716 | Cz8 | Cz8 | Cz8 | m-D1 | H |
| 1717 | m-D1 | Cz8 | Cz8 | H | Cz8 |
| 1718 | Cz8 | Cz8 | m-D1 | H | Cz8 |
| 1719 | Cz8 | m-D1 | H | Cz8 | Cz8 |
| 1720 | Cz8 | m-D1 | Cz8 | H | H |
| 1721 | Cz8 | Cz8 | m-D1 | H | H |
| 1722 | H | m-D1 | Cz8 | Cz8 | H |
| 1723 | H | Cz8 | m-D1 | Cz8 | H |
| 1724 | m-D1 | H | Cz8 | H | Cz8 |
| 1725 | Cz8 | H | m-D1 | H | Cz8 |
| 1726 | m-D1 | Cz8 | H | H | H |
| 1727 | H | m-D1 | H | Cz8 | H |
| 1728 | m-D1 | m-D1 | Cz8 | H | Cz8 |
| 1729 | m-D1 | Cz8 | m-D1 | H | Cz8 |
| 1730 | Cz8 | m-D1 | m-D1 | H | Cz8 |
| 1731 | m-D1 | m-D1 | H | Cz8 | Cz8 |
| 1732 | Cz8 | m-D1 | H | m-D1 | Cz8 |
| 1733 | m-D1 | Cz8 | m-D1 | H | H |
| 1734 | H | m-D1 | m-D1 | Cz8 | H |
| 1735 | H | m-D1 | Cz8 | m-D1 | H |
| 1736 | m-D1 | H | m-D1 | H | Cz8 |
| 1737 | m-D1 | H | Cz8 | H | m-D1 |
| 1738 | m-D1 | Cz8 | m-D1 | Cz8 | m-D1 |
| 1739 | m-D1 | m-D1 | m-D1 | Cz8 | H |
| 1740 | m-D1 | m-D1 | Cz8 | m-D1 | H |
| 1741 | m-D1 | m-D1 | m-D1 | H | Cz8 |

TABLE 1-31-continued

| | | | | | |
|---|---|---|---|---|---|
| 1742 | m-D1 | m-D1 | H | m-D1 | Cz8 |
| 1743 | m-D1 | m-D1 | H | Cz8 | m-D1 |
| 1744 | m-D1 | m-D1 | m-D1 | m-D1 | Cz8 |
| 1745 | Cz8 | Cz8 | m-D2 | Cz8 | Cz8 |
| 1746 | m-D2 | Cz8 | Cz8 | Cz8 | H |
| 1747 | Cz8 | Cz8 | Cz8 | m-D2 | H |
| 1748 | m-D2 | Cz8 | Cz8 | H | Cz8 |
| 1749 | Cz8 | Cz8 | m-D2 | H | Cz8 |
| 1750 | Cz8 | m-D2 | H | Cz8 | Cz8 |
| 1751 | Cz8 | m-D2 | Cz8 | H | H |
| 1752 | Cz8 | Cz8 | m-D2 | H | H |
| 1753 | H | m-D2 | Cz8 | Cz8 | H |

TABLE 1-32

| | | | | | |
|---|---|---|---|---|---|
| 1754 | H | Cz8 | m-D2 | Cz8 | H |
| 1755 | m-D2 | H | Cz8 | H | Cz8 |
| 1756 | Cz8 | H | m-D2 | H | Cz8 |
| 1757 | m-D2 | Cz8 | H | H | H |
| 1758 | H | m-D2 | H | Cz8 | H |
| 1759 | m-D2 | m-D2 | Cz8 | H | H |
| 1760 | m-D2 | Cz8 | m-D2 | H | Cz8 |
| 1761 | Cz8 | m-D2 | m-D2 | H | Cz8 |
| 1762 | m-D2 | m-D2 | H | Cz8 | Cz8 |
| 1763 | Cz8 | m-D2 | H | m-D2 | Cz8 |
| 1764 | m-D2 | Cz8 | m-D2 | H | H |
| 1765 | H | m-D2 | m-D2 | Cz8 | H |
| 1766 | H | m-D2 | Cz8 | m-D2 | H |
| 1767 | m-D2 | H | m-D2 | H | Cz8 |
| 1768 | Cz8 | H | Cz8 | H | m-D2 |
| 1769 | m-D2 | Cz8 | m-D2 | Cz8 | m-D2 |
| 1770 | m-D2 | m-D2 | m-D2 | Cz8 | H |
| 1771 | m-D2 | m-D2 | Cz8 | m-D2 | H |
| 1772 | m-D2 | m-D2 | m-D2 | H | Cz8 |
| 1773 | m-D2 | m-D2 | H | m-D2 | Cz8 |
| 1774 | m-D2 | m-D2 | H | Cz8 | m-D2 |
| 1775 | m-D2 | m-D2 | m-D2 | m-D2 | Cz8 |
| 1776 | Cz8 | Cz8 | m-D3 | Cz8 | Cz8 |
| 1777 | m-D3 | Cz8 | Cz8 | Cz8 | H |
| 1778 | Cz8 | Cz8 | Cz8 | m-D3 | H |
| 1779 | m-D3 | Cz8 | Cz8 | H | Cz8 |
| 1780 | Cz8 | Cz8 | m-D3 | H | Cz8 |
| 1781 | Cz8 | m-D3 | H | Cz8 | Cz8 |
| 1782 | Cz8 | m-D3 | Cz8 | H | H |
| 1783 | Cz8 | Cz8 | m-D3 | H | H |
| 1784 | H | m-D3 | Cz8 | Cz8 | H |
| 1785 | H | Cz8 | m-D3 | Cz8 | H |
| 1786 | m-D3 | H | Cz8 | H | Cz8 |
| 1787 | Cz8 | H | m-D3 | H | Cz8 |
| 1788 | m-D3 | Cz8 | H | H | H |
| 1789 | H | m-D3 | H | Cz8 | H |
| 1790 | m-D3 | m-D3 | Cz8 | H | H |
| 1791 | m-D3 | Cz8 | m-D3 | H | Cz8 |
| 1792 | Cz8 | m-D3 | m-D3 | H | Cz8 |
| 1793 | m-D3 | m-D3 | H | Cz8 | Cz8 |
| 1794 | Cz8 | m-D3 | H | m-D3 | Cz8 |
| 1795 | m-D3 | Cz8 | m-D3 | H | H |
| 1796 | H | m-D3 | m-D3 | Cz8 | H |
| 1797 | H | m-D3 | Cz8 | m-D3 | H |
| 1798 | m-D3 | H | m-D3 | H | Cz8 |
| 1799 | m-D3 | H | Cz8 | H | m-D3 |
| 1800 | m-D3 | Cz8 | m-D3 | Cz8 | m-D3 |
| 1801 | m-D3 | m-D3 | m-D3 | Cz8 | H |
| 1802 | m-D3 | m-D3 | Cz8 | m-D3 | H |
| 1803 | m-D3 | m-D3 | m-D3 | H | Cz8 |
| 1804 | m-D3 | m-D3 | H | m-D3 | Cz8 |
| 1805 | m-D3 | m-D3 | H | Cz8 | m-D3 |
| 1806 | m-D3 | m-D3 | m-D3 | m-D3 | Cz8 |

TABLE 1-33

| No | R¹ | R² | R³ | R⁴ | R⁵ |
|---|---|---|---|---|---|
| 1807 | m-D1 | Cz | Cz | Cz | methyl |
| 1808 | Cz | Cz | Cz | m-D1 | methyl |

TABLE 1-33-continued

| No | R¹ | R² | R³ | R⁴ | R⁵ |
|---|---|---|---|---|---|
| 1809 | m-D1 | Cz | Cz | methyl | Cz |
| 1810 | Cz | Cz | m-D1 | Cz | methyl |
| 1811 | Cz | m-D1 | methyl | Cz | Cz |
| 1812 | Cz | m-D1 | Cz | methyl | methyl |
| 1813 | Cz | Cz | m-D1 | methyl | methyl |
| 1814 | methyl | m-D1 | Cz | Cz | methyl |
| 1815 | methyl | Cz | m-D1 | Cz | methyl |
| 1816 | m-D1 | methyl | Cz | methyl | Cz |
| 1817 | Cz | methyl | m-D1 | methyl | Cz |
| 1818 | m-D1 | Cz | methyl | methyl | methyl |
| 1819 | m-D1 | m-D1 | methyl | Cz | methyl |
| 1820 | m-D1 | m-D1 | Cz | methyl | Cz |
| 1821 | m-D1 | Cz | m-D1 | methyl | Cz |
| 1822 | Cz | m-D1 | m-D1 | methyl | Cz |
| 1823 | Cz | m-D1 | Cz | methyl | methyl |
| 1824 | Cz | m-D1 | methyl | m-D1 | Cz |
| 1825 | m-D1 | Cz | m-D1 | methyl | methyl |
| 1826 | methyl | m-D1 | m-D1 | Cz | methyl |
| 1827 | methyl | m-D1 | Cz | m-D1 | methyl |
| 1828 | m-D1 | methyl | m-D1 | methyl | Cz |
| 1829 | m-D1 | methyl | Cz | methyl | m-D1 |
| 1830 | methyl | m-D1 | m-D1 | methyl | methyl |
| 1831 | m-D1 | m-D1 | m-D1 | Cz | methyl |
| 1832 | m-D1 | m-D1 | Cz | m-D1 | methyl |
| 1833 | m-D1 | m-D1 | m-D1 | methyl | Cz |
| 1834 | m-D1 | m-D1 | methyl | m-D1 | Cz |
| 1835 | m-D1 | m-D1 | methyl | Cz | m-D1 |
| 1836 | m-D1 | m-D1 | methyl | m-D1 | methyl |
| 1837 | methyl | m-D1 | m-D1 | m-D1 | methyl |
| 1838 | m-D1 | m-D1 | m-D1 | m-D1 | methyl |
| 1839 | m-D1 | m-D1 | methyl | m-D1 | m-D1 |
| 1840 | m-D2 | Cz | Cz | Cz | methyl |
| 1841 | Cz | Cz | Cz | m-D2 | methyl |
| 1842 | m-D2 | Cz | Cz | methyl | Cz |
| 1843 | Cz | Cz | m-D2 | methyl | Cz |
| 1844 | Cz | m-D2 | methyl | Cz | Cz |
| 1845 | Cz | m-D2 | Cz | methyl | methyl |
| 1846 | Cz | Cz | m-D2 | methyl | methyl |
| 1847 | methyl | m-D2 | Cz | Cz | methyl |
| 1848 | methyl | Cz | m-D2 | Cz | methyl |
| 1849 | m-D2 | methyl | Cz | methyl | Cz |
| 1850 | Cz | methyl | m-D2 | methyl | Cz |
| 1851 | m-D2 | Cz | methyl | methyl | methyl |
| 1852 | methyl | m-D2 | methyl | Cz | methyl |
| 1853 | m-D2 | m-D2 | Cz | methyl | Cz |
| 1854 | m-D2 | Cz | m-D2 | methyl | Cz |
| 1855 | Cz | m-D2 | m-D2 | methyl | Cz |
| 1856 | m-D2 | m-D2 | methyl | Cz | Cz |
| 1857 | Cz | m-D2 | methyl | m-D2 | Cz |
| 1858 | m-D2 | Cz | m-D2 | methyl | methyl |
| 1859 | methyl | m-D2 | m-D2 | Cz | methyl |
| 1860 | methyl | m-D2 | Cz | m-D2 | methyl |
| 1861 | m-D2 | methyl | m-D2 | methyl | Cz |
| 1862 | m-D2 | methyl | Cz | methyl | m-D2 |
| 1863 | methyl | m-D2 | m-D2 | methyl | methyl |
| 1864 | m-D2 | m-D2 | m-D2 | methyl | methyl |

TABLE 1-34

| | | | | | |
|---|---|---|---|---|---|
| 1865 | m-D2 | m-D2 | Cz | m-D2 | methyl |
| 1866 | m-D2 | m-D2 | m-D2 | methyl | Cz |
| 1867 | m-D2 | m-D2 | methyl | m-D2 | Cz |
| 1868 | m-D2 | m-D2 | methyl | Cz | m-D2 |
| 1869 | m-D2 | m-D2 | methyl | m-D2 | methyl |
| 1870 | methyl | m-D2 | m-D2 | m-D2 | methyl |
| 1871 | m-D2 | m-D2 | m-D2 | m-D2 | methyl |
| 1872 | m-D2 | m-D2 | methyl | m-D2 | m-D2 |
| 1873 | m-D3 | Cz | Cz | Cz | methyl |
| 1874 | Cz | Cz | Cz | m-D3 | methyl |
| 1875 | m-D3 | Cz | Cz | methyl | Cz |
| 1876 | Cz | Cz | m-D3 | methyl | Cz |
| 1877 | Cz | m-D3 | methyl | Cz | Cz |
| 1878 | Cz | m-D3 | Cz | methyl | methyl |
| 1879 | Cz | Cz | m-D3 | methyl | methyl |
| 1880 | methyl | m-D3 | Cz | Cz | methyl |

TABLE 1-34-continued

| | | | | | |
|---|---|---|---|---|---|
| 1881 | methyl | Cz | m-D3 | Cz | methyl |
| 1882 | m-D3 | methyl | Cz | methyl | Cz |
| 1883 | Cz | methyl | m-D3 | methyl | Cz |
| 1884 | m-D3 | Cz | methyl | methyl | methyl |
| 1885 | methyl | m-D3 | methyl | Cz | methyl |
| 1886 | m-D3 | m-D3 | Cz | methyl | Cz |
| 1887 | m-D3 | Cz | m-D3 | methyl | Cz |
| 1888 | Cz | m-D3 | m-D3 | methyl | Cz |
| 1889 | m-D3 | m-D3 | methyl | Cz | Cz |
| 1890 | Cz | m-D3 | methyl | m-D3 | Cz |
| 1891 | m-D3 | Cz | m-D3 | methyl | methyl |
| 1892 | methyl | m-D3 | m-D3 | Cz | methyl |
| 1893 | methyl | m-D3 | Cz | m-D3 | methyl |
| 1894 | m-D3 | methyl | m-D3 | methyl | Cz |
| 1895 | m-D3 | methyl | Cz | methyl | m-D3 |
| 1896 | methyl | m-D3 | m-D3 | methyl | methyl |
| 1897 | m-D3 | m-D3 | m-D3 | Cz | methyl |
| 1898 | m-D3 | m-D3 | Cz | m-D3 | methyl |
| 1899 | m-D3 | m-D3 | m-D3 | methyl | Cz |
| 1900 | m-D3 | m-D3 | methyl | m-D3 | Cz |
| 1901 | m-D3 | m-D3 | methyl | Cz | m-D3 |
| 1902 | m-D3 | m-D3 | methyl | m-D3 | methyl |
| 1903 | methyl | m-D3 | m-D3 | methyl | methyl |
| 1904 | m-D3 | m-D3 | m-D3 | m-D3 | methyl |
| 1905 | m-D3 | m-D3 | methyl | m-D3 | m-D3 |
| 1906 | m-D1 | Cz | Cz | Cz | phenyl |
| 1907 | Cz | Cz | Cz | m-D1 | phenyl |
| 1908 | m-D1 | Cz | Cz | phenyl | Cz |
| 1909 | Cz | Cz | m-D1 | phenyl | Cz |
| 1910 | Cz | m-D1 | phenyl | Cz | Cz |
| 1911 | Cz | m-D1 | Cz | phenyl | phenyl |
| 1912 | Cz | Cz | m-D1 | phenyl | phenyl |
| 1913 | phenyl | m-D1 | Cz | Cz | phenyl |
| 1914 | phenyl | Cz | m-D1 | Cz | phenyl |
| 1915 | m-D1 | phenyl | Cz | Cz | Cz |
| 1916 | Cz | phenyl | m-D1 | Cz | Cz |
| 1917 | m-D1 | Cz | phenyl | phenyl | phenyl |
| 1918 | phenyl | m-D1 | phenyl | Cz | phenyl |
| 1919 | m-D1 | m-D1 | Cz | phenyl | Cz |
| 1920 | m-D1 | Cz | m-D1 | phenyl | Cz |
| 1921 | Cz | m-D1 | m-D1 | phenyl | Cz |
| 1922 | m-D1 | m-D1 | phenyl | Cz | Cz |
| 1923 | Cz | m-D1 | phenyl | m-D1 | Cz |

TABLE 1-35

| | | | | | |
|---|---|---|---|---|---|
| 1924 | m-D1 | Cz | m-D1 | phenyl | phenyl |
| 1925 | phenyl | m-D1 | m-D1 | Cz | phenyl |
| 1926 | phenyl | m-D1 | Cz | m-D1 | phenyl |
| 1927 | m-D1 | phenyl | m-D1 | phenyl | Cz |
| 1928 | m-D1 | phenyl | Cz | phenyl | m-D1 |
| 1929 | phenyl | m-D1 | m-D1 | phenyl | phenyl |
| 1930 | m-D1 | m-D1 | m-D1 | Cz | phenyl |
| 1931 | m-D1 | m-D1 | Cz | m-D1 | phenyl |
| 1932 | m-D1 | Cz | m-D1 | m-D1 | phenyl |
| 1933 | m-D1 | m-D1 | phenyl | m-D1 | Cz |
| 1934 | m-D1 | m-D1 | phenyl | Cz | m-D1 |
| 1935 | m-D1 | m-D1 | phenyl | m-D1 | phenyl |
| 1936 | phenyl | m-D1 | m-D1 | m-D1 | phenyl |
| 1937 | m-D1 | m-D1 | m-D1 | m-D1 | Cz |
| 1938 | m-D1 | m-D1 | phenyl | m-D1 | m-D1 |
| 1939 | m-D2 | Cz | Cz | Cz | phenyl |
| 1940 | Cz | Cz | Cz | m-D2 | phenyl |
| 1941 | m-D2 | Cz | Cz | phenyl | Cz |
| 1942 | Cz | Cz | m-D2 | phenyl | Cz |
| 1943 | Ca | m-D2 | phenyl | Cz | Cz |
| 1944 | Cz | m-D2 | Cz | phenyl | phenyl |
| 1945 | Cz | Cz | m-D2 | phenyl | phenyl |
| 1946 | phenyl | m-D2 | Cz | Cz | phenyl |
| 1947 | phenyl | Cz | m-D2 | Cz | phenyl |
| 1948 | m-D2 | phenyl | Cz | phenyl | Cz |
| 1949 | Cz | phenyl | m-D2 | Cz | Cz |
| 1950 | m-D2 | Cz | phenyl | phenyl | phenyl |
| 1951 | phenyl | m-D2 | phenyl | Cz | phenyl |
| 1952 | m-D2 | Cz | Cz | phenyl | Cz |
| 1953 | m-D2 | Cz | m-D2 | phenyl | Cz |
| 1954 | Cz | m-D2 | m-D2 | phenyl | Cz |

TABLE 1-35-continued

| | | | | | |
|---|---|---|---|---|---|
| 1955 | m-D2 | m-D2 | phenyl | Cz | Cz |
| 1956 | Cz | m-D2 | phenyl | m-D2 | Cz |
| 1957 | m-D2 | Cz | m-D2 | phenyl | phenyl |
| 1958 | phenyl | m-D2 | m-D2 | Cz | phenyl |
| 1959 | phenyl | m-D2 | Cz | m-D2 | phenyl |
| 1960 | m-D2 | phenyl | m-D2 | phenyl | Cz |
| 1961 | m-D2 | phenyl | Cz | phenyl | m-D2 |
| 1962 | phenyl | m-D2 | m-D2 | phenyl | phenyl |
| 1963 | m-D2 | m-D2 | m-D2 | Cz | phenyl |
| 1964 | m-D2 | m-D2 | Cz | m-D2 | phenyl |
| 1965 | m-D2 | m-D2 | m-D2 | phenyl | Cz |
| 1966 | m-D2 | m-D2 | phenyl | m-D2 | Cz |
| 1967 | m-D2 | m-D2 | phenyl | Cz | m-D2 |
| 1968 | m-D2 | m-D2 | phenyl | m-D2 | phenyl |
| 1969 | phenyl | m-D2 | m-D2 | m-D2 | phenyl |
| 1970 | m-D2 | m-D2 | m-D2 | m-D2 | phenyl |
| 1971 | m-D2 | m-D2 | phenyl | m-D2 | m-D2 |
| 1972 | m-D3 | Cz | Cz | Cz | phenyl |
| 1973 | Cz | Cz | Cz | m-D3 | phenyl |
| 1974 | m-D3 | Cz | Cz | phenyl | Cz |
| 1975 | Cz | Cz | m-D3 | phenyl | Cz |
| 1976 | Cz | m-D3 | phenyl | Cz | Cz |
| 1977 | Cz | m-D3 | Cz | phenyl | phenyl |
| 1978 | Cz | Cz | m-D3 | phenyl | phenyl |
| 1979 | phenyl | m-D3 | Cz | Cz | phenyl |
| 1980 | phenyl | Cz | m-D3 | Cz | phenyl |
| 1981 | m-D3 | phenyl | Cz | phenyl | Cz |
| 1982 | Cz | phenyl | m-D3 | phenyl | Cz |

TABLE 1-36

| | | | | | |
|---|---|---|---|---|---|
| 1983 | m-D3 | Cz | phenyl | phenyl | phenyl |
| 1984 | phenyl | m-D3 | phenyl | Cz | phenyl |
| 1985 | m-D3 | m-D3 | Cz | phenyl | Cz |
| 1986 | m-D3 | Cz | m-D3 | phenyl | Cz |
| 1987 | Cz | m-D3 | m-D3 | phenyl | Cz |
| 1988 | m-D3 | m-D3 | phenyl | Cz | Cz |
| 1989 | Cz | m-D3 | phenyl | m-D3 | Cz |
| 1990 | m-D3 | Cz | m-D3 | phenyl | phenyl |
| 1991 | phenyl | m-D3 | m-D3 | Cz | phenyl |
| 1992 | phenyl | m-D3 | Cz | m-D3 | phenyl |
| 1993 | m-D3 | phenyl | m-D3 | phenyl | Cz |
| 1994 | m-D3 | phenyl | Cz | phenyl | m-D3 |
| 1995 | phenyl | m-D3 | m-D3 | phenyl | phenyl |
| 1996 | m-D3 | m-D3 | m-D3 | Cz | phenyl |
| 1997 | m-D3 | m-D3 | Cz | m-D3 | phenyl |
| 1998 | m-D3 | m-D3 | m-D3 | phenyl | Cz |
| 1999 | m-D3 | m-D3 | phenyl | m-D3 | Cz |
| 2000 | m-D3 | m-D3 | phenyl | Cz | m-D3 |
| 2001 | m-D3 | m-D3 | phenyl | m-D3 | phenyl |
| 2002 | phenyl | m-D3 | m-D3 | m-D3 | phenyl |
| 2003 | m-D3 | m-D3 | m-D3 | m-D3 | phenyl |
| 2004 | m-D3 | m-D3 | phenyl | m-D3 | m-D3 |
| 2005 | m-D1 | Cz | Cz | Cz | 4-pyridyl |
| 2006 | Cz | Cz | Cz | m-D1 | 4-pyridyl |
| 2007 | m-D1 | Cz | Cz | 4-pyridyl | Cz |
| 2008 | Cz | Cz | m-D1 | 4-pyridyl | Cz |
| 2009 | Cz | m-D1 | 4-pyridyl | Cz | Cz |
| 2010 | Cz | m-D1 | Cz | 4-pyridyl | 4-pyridyl |
| 2011 | Cz | Cz | m-D1 | 4-pyridyl | 4-pyridyl |
| 2012 | 4-pyridyl | m-D1 | Cz | Cz | 4-pyridyl |
| 2013 | 4-pyridyl | Cz | m-D1 | Cz | 4-pyridyl |
| 2014 | m-D1 | 4-pyridyl | Cz | 4-pyridyl | Cz |
| 2015 | Cz | 4-pyridyl | m-D1 | 4-pyridyl | Cz |
| 2016 | m-D1 | Cz | 4-pyridyl | 4-pyridyl | 4-pyridyl |
| 2017 | 4-pyridyl | m-D1 | 4-pyridyl | Cz | 4-pyridyl |
| 2018 | m-D1 | m-D1 | Cz | 4-pyridyl | Cz |
| 2019 | m-D1 | Cz | m-D1 | 4-pyridyl | Cz |
| 2020 | Cz | m-D1 | m-D1 | 4-pyridyl | Cz |
| 2021 | m-D1 | m-D1 | 4-pyridyl | Cz | Cz |
| 2022 | Cz | m-D1 | 4-pyridyl | m-D1 | Cz |
| 2023 | m-D1 | Cz | m-D1 | 4-pyridyl | 4-pyridyl |
| 2024 | 4-pyridyl | m-D1 | m-D1 | Cz | 4-pyridyl |
| 2025 | 4-pyridyl | m-D1 | Cz | m-D1 | 4-pyridyl |
| 2026 | m-D1 | 4-pyridyl | m-D1 | 4-pyridyl | Cz |
| 2027 | m-D1 | 4-pyridyl | Cz | 4-pyridyl | m-D1 |
| 2028 | 4-pyridyl | m-D1 | m-D1 | 4-pyridyl | 4-pyridyl |

TABLE 1-36-continued

| | | | | | |
|---|---|---|---|---|---|
| 2029 | m-D1 | m-D1 | m-D1 | Cz | 4-pyridyl |
| 2030 | m-D1 | m-D1 | Cz | m-D1 | 4-pyridyl |
| 2031 | m-D1 | m-D1 | m-D1 | 4-pyridyl | Cz |
| 2032 | m-D1 | m-D1 | 4-pyridyl | m-D1 | Cz |
| 2033 | m-D1 | m-D1 | 4-pyridyl | Cz | m-D1 |
| 2034 | m-D1 | m-D1 | 4-pyridyl | m-D1 | 4-pyridyl |
| 2035 | 4-pyridyl | m-D1 | m-D1 | m-D1 | 4-pyridyl |
| 2036 | m-D1 | m-D1 | m-D1 | m-D1 | 4-pyridyl |
| 2037 | m-D1 | m-D1 | 4-pyridyl | m-D1 | m-D1 |
| 2038 | m-D2 | Cz | Cz | Cz | 4-pyridyl |
| 2039 | Cz | Cz | Cz | m-D2 | 4-pyridyl |
| 2040 | m-D2 | Cz | Cz | 4-pyridyl | Cz |
| 2041 | Cz | Cz | m-D2 | 4-pyridyl | Cz |

TABLE 1-37

| | | | | | |
|---|---|---|---|---|---|
| 2042 | Cz | m-D2 | 4-pyridyl | Cz | Cz |
| 2043 | Cz | m-D2 | Cz | 4-pyridyl | 4-pyridyl |
| 2044 | Cz | Cz | m-D2 | 4-pyridyl | 4-pyridyl |
| 2045 | 4-pyridyl | m-D2 | Cz | Cz | 4-pyridyl |
| 2046 | 4-pyridyl | Cz | m-D2 | Cz | 4-pyridyl |
| 2047 | m-D2 | 4-pyridyl | Cz | 4-pyridyl | Cz |
| 2048 | Cz | 4-pyridyl | m-D2 | 4-pyridyl | Cz |
| 2049 | m-D2 | Cz | 4-pyridyl | Cz | 4-pyridyl |
| 2050 | 4-pyridyl | m-D2 | 4-pyridyl | Cz | 4-pyridyl |
| 2051 | m-D2 | m-D2 | Cz | 4-pyridyl | Cz |
| 2052 | m-D2 | Cz | m-D2 | 4-pyridyl | Cz |
| 2053 | Cz | m-D2 | m-D2 | 4-pyridyl | Cz |
| 2054 | m-D2 | m-D2 | 4-pyridyl | Cz | Cz |
| 2055 | Cz | m-D2 | 4-pyridyl | m-D2 | Cz |
| 2056 | m-D2 | Cz | m-D2 | 4-pyridyl | 4-pyridyl |
| 2057 | 4-pyridyl | m-D2 | m-D2 | Cz | 4-pyridyl |
| 2058 | 4-pyridyl | m-D2 | Cz | m-D2 | 4-pyridyl |
| 2059 | m-D2 | 4-pyridyl | m-D2 | 4-pyridyl | Cz |
| 2060 | m-D2 | 4-pyridyl | Cz | 4-pyridyl | m-D2 |
| 2061 | 4-pyridyl | m-D2 | m-D2 | 4-pyridyl | m-D2 |
| 2062 | m-D2 | m-D2 | m-D2 | 4-pyridyl | 4-pyridyl |
| 2063 | m-D2 | m-D2 | Cz | m-D2 | 4-pyridyl |
| 2064 | m-D2 | m-D2 | m-D2 | 4-pyridyl | Cz |
| 2065 | m-D2 | m-D2 | 4-pyridyl | m-D2 | Cz |
| 2066 | m-D2 | m-D2 | 4-pyridyl | Cz | m-D2 |
| 2067 | m-D2 | m-D2 | 4-pyridyl | m-D2 | 4-pyridyl |
| 2068 | 4-pyridyl | m-D2 | m-D2 | m-D2 | 4-pyridyl |
| 2069 | m-D2 | m-D2 | m-D2 | m-D2 | 4-pyridyl |
| 2070 | m-D2 | m-D2 | 4-pyridyl | m-D2 | m-D2 |
| 2071 | m-D3 | Cz | Cz | Cz | 4-pyridyl |
| 2072 | Cz | Cz | Cz | m-D3 | 4-pyridyl |
| 2073 | m-D3 | Cz | Cz | 4-pyridyl | Cz |
| 2074 | Cz | Cz | m-D3 | 4-pyridyl | Cz |
| 2075 | Cz | m-D3 | 4-pyridyl | Cz | Cz |
| 2076 | Cz | m-D3 | Cz | 4-pyridyl | 4-pyridyl |
| 2077 | Cz | Cz | m-D3 | 4-pyridyl | 4-pyridyl |
| 2078 | 4-pyridyl | m-D3 | Cz | Cz | 4-pyridyl |
| 2079 | 4-pyridyl | Cz | m-D3 | Cz | 4-pyridyl |
| 2080 | m-D3 | 4-pyridyl | Cz | 4-pyridyl | Cz |
| 2081 | Cz | 4-pyridyl | m-D3 | Cz | Cz |
| 2082 | m-D3 | Cz | 4-pyridyl | Cz | 4-pyridyl |
| 2083 | 4-pyridyl | m-D3 | 4-pyridyl | Cz | 4-pyridyl |
| 2084 | m-D3 | m-D3 | Cz | 4-pyridyl | Cz |
| 2085 | m-D3 | Cz | m-D3 | 4-pyridyl | Cz |
| 2086 | Cz | m-D3 | m-D3 | 4-pyridyl | Cz |
| 2087 | m-D3 | m-D3 | 4-pyridyl | Cz | Cz |
| 2088 | Cz | m-D3 | 4-pyridyl | m-D3 | Cz |
| 2089 | m-D3 | Cz | m-D3 | 4-pyridyl | 4-pyridyl |
| 2090 | 4-pyridyl | m-D3 | m-D3 | Cz | 4-pyridyl |
| 2091 | 4-pyridyl | m-D3 | Cz | m-D3 | 4-pyridyl |
| 2092 | m-D3 | 4-pyridyl | m-D3 | 4-pyridyl | Cz |
| 2093 | m-D3 | 4-pyridyl | Cz | 4-pyridyl | m-D3 |
| 2094 | 4-pyridyl | m-D3 | m-D3 | 4-pyridyl | m-D3 |
| 2095 | m-D3 | m-D3 | m-D3 | Cz | 4-pyridyl |
| 2096 | m-D3 | m-D3 | Cz | m-D3 | 4-pyridyl |
| 2097 | m-D3 | m-D3 | m-D3 | 4-pyridyl | Cz |
| 2098 | m-D3 | m-D3 | 4-pyridyl | m-D3 | Cz |
| 2099 | m-D3 | m-D3 | 4-pyridyl | Cz | m-D3 |
| 2100 | m-D3 | m-D3 | 4-pyridyl | m-D3 | 4-pyridyl |

TABLE 1-38

| | | | | | |
|---|---|---|---|---|---|
| 2101 | 4-pyridyl | m-D3 | m-D3 | m-D3 | 4-pyridyl |
| 2102 | m-D3 | m-D3 | m-D3 | m-D3 | 4-pyridyl |
| 2103 | m-D3 | m-D3 | 4-pyridyl | m-D3 | m-D3 |
| 2104 | m-D1 | Cz | Cz | Cz | methoxy |
| 2105 | Cz | Cz | Cz | m-D1 | methoxy |
| 2106 | m-D1 | Cz | Cz | methoxy | Cz |
| 2107 | Cz | Cz | m-D1 | methoxy | Cz |
| 2108 | Cz | m-D1 | methoxy | Cz | Cz |
| 2109 | Cz | m-D1 | Cz | methoxy | methoxy |
| 2110 | Cz | Cz | m-D1 | methoxy | methoxy |
| 2111 | methoxy | m-D1 | Cz | Cz | methoxy |
| 2112 | methoxy | Cz | m-D1 | Cz | methoxy |
| 2113 | m-D1 | methoxy | Cz | methoxy | Cz |
| 2114 | Cz | methoxy | m-D1 | methoxy | Cz |
| 2115 | m-D1 | Cz | methoxy | methoxy | methoxy |
| 2116 | methoxy | m-D1 | methoxy | Cz | methoxy |
| 2117 | m-D1 | m-D1 | Cz | methoxy | Cz |
| 2118 | m-D1 | Cz | m-D1 | methoxy | Cz |
| 2119 | Cz | m-D1 | m-D1 | methoxy | Cz |
| 2120 | m-D1 | m-D1 | methoxy | Cz | Cz |
| 2121 | Cz | m-D1 | methoxy | m-D1 | Cz |
| 2122 | m-D1 | Cz | m-D1 | methoxy | methoxy |
| 2123 | methoxy | m-D1 | m-D1 | Cz | methoxy |
| 2124 | methoxy | m-D1 | Cz | m-D1 | methoxy |
| 2125 | m-D1 | methoxy | m-D1 | methoxy | Cz |
| 2126 | m-D1 | methoxy | Cz | methoxy | m-D1 |
| 2127 | methoxy | m-D1 | m-D1 | methoxy | methoxy |
| 2128 | m-D1 | m-D1 | m-D1 | Cz | methoxy |
| 2129 | m-D1 | m-D1 | Cz | m-D1 | methoxy |
| 2130 | m-D1 | m-D1 | m-D1 | methoxy | Cz |
| 2131 | m-D1 | m-D1 | methoxy | m-D1 | Cz |
| 2132 | m-D1 | m-D1 | methoxy | Cz | m-D1 |
| 2133 | m-D1 | m-D1 | methoxy | m-D1 | methoxy |
| 2134 | methoxy | m-D1 | m-D1 | m-D1 | methoxy |
| 2135 | m-D1 | m-D1 | m-D1 | m-D1 | methoxy |
| 2136 | m-D1 | m-D1 | methoxy | m-D1 | m-D1 |
| 2137 | m-D2 | Cz | Cz | Cz | methoxy |
| 2138 | Cz | Cz | Cz | m-D2 | methoxy |
| 2139 | m-D2 | Cz | Cz | methoxy | Cz |
| 2140 | Cz | Cz | m-D2 | methoxy | Cz |
| 2141 | Cz | m-D2 | methoxy | Cz | Cz |
| 2142 | Cz | m-D2 | Cz | methoxy | methoxy |
| 2143 | Cz | Cz | m-D2 | methoxy | methoxy |
| 2144 | methoxy | m-D2 | Cz | Cz | methoxy |
| 2145 | methoxy | Cz | m-D2 | Cz | methoxy |
| 2146 | m-D2 | methoxy | Cz | methoxy | Cz |
| 2147 | Cz | methoxy | m-D2 | methoxy | Cz |
| 2148 | m-D2 | Cz | methoxy | methoxy | methoxy |
| 2149 | methoxy | m-D2 | methoxy | Cz | methoxy |
| 2150 | m-D2 | m-D2 | Cz | methoxy | Cz |
| 2151 | m-D2 | Cz | m-D2 | methoxy | Cz |
| 2152 | Cz | m-D2 | m-D2 | methoxy | Cz |
| 2153 | m-D2 | m-D2 | methoxy | Cz | Cz |
| 2154 | Cz | m-D2 | methoxy | m-D2 | Cz |
| 2155 | m-D2 | Cz | m-D2 | methoxy | methoxy |
| 2156 | methoxy | m-D2 | m-D2 | Cz | methoxy |
| 2157 | methoxy | m-D2 | Cz | m-D2 | methoxy |
| 2158 | m-D2 | methoxy | m-D2 | methoxy | Cz |
| 2159 | m-D2 | methoxy | Cz | methoxy | m-D2 |

TABLE 1-39

| | | | | | |
|---|---|---|---|---|---|
| 2160 | methoxy | m-D2 | m-D2 | methoxy | methoxy |
| 2161 | m-D2 | m-D2 | m-D2 | Cz | methoxy |
| 2162 | m-D2 | m-D2 | Cz | m-D2 | methoxy |
| 2163 | m-D2 | m-D2 | m-D2 | methoxy | Cz |
| 2164 | m-D2 | m-D2 | methoxy | m-D2 | Cz |
| 2165 | m-D2 | m-D2 | methoxy | Cz | m-D2 |
| 2166 | m-D2 | m-D2 | methoxy | m-D2 | methoxy |
| 2167 | methoxy | m-D2 | m-D2 | m-D2 | methoxy |
| 2168 | m-D2 | m-D2 | m-D2 | m-D2 | methoxy |
| 2169 | m-D2 | m-D2 | methoxy | m-D2 | m-D2 |
| 2170 | m-D3 | Cz | Cz | Cz | methoxy |
| 2171 | Cz | Cz | Cz | m-D3 | methoxy |
| 2172 | m-D3 | Cz | Cz | methoxy | Cz |
| 2173 | Cz | Cz | m-D3 | methoxy | Cz |
| 2174 | Cz | m-D3 | methoxy | Cz | Cz |

TABLE 1-39-continued

| | | | | | |
|---|---|---|---|---|---|
| 2175 | Cz | m-D3 | Cz | methoxy | methoxy |
| 2176 | Cz | Cz | m-D3 | methoxy | methoxy |
| 2177 | methoxy | m-D3 | Cz | Cz | methoxy |
| 2178 | methoxy | Cz | m-D3 | Cz | methoxy |
| 2179 | m-D3 | methoxy | Cz | methoxy | Cz |
| 2180 | Cz | methoxy | m-D3 | methoxy | Cz |
| 2181 | m-D3 | Cz | methoxy | methoxy | methoxy |
| 2182 | methoxy | m-D3 | methoxy | Cz | methoxy |
| 2183 | m-D3 | m-D3 | Cz | methoxy | Cz |
| 2184 | m-D3 | Cz | m-D3 | methoxy | Cz |
| 2185 | Cz | m-D3 | m-D3 | methoxy | Cz |
| 2186 | m-D3 | m-D3 | methoxy | Cz | Cz |
| 2187 | Cz | m-D3 | methoxy | m-D3 | Cz |
| 2188 | m-D3 | Cz | m-D3 | methoxy | methoxy |
| 2189 | methoxy | m-D3 | m-D3 | Cz | methoxy |
| 2190 | methoxy | m-D3 | Cz | m-D3 | methoxy |
| 2191 | m-D3 | methoxy | m-D3 | methoxy | Cz |
| 2192 | m-D3 | methoxy | Cz | methoxy | m-D3 |
| 2193 | methoxy | m-D3 | m-D3 | methoxy | methoxy |
| 2194 | m-D3 | m-D3 | m-D3 | Cz | methoxy |
| 2195 | m-D3 | m-D3 | Cz | m-D3 | methoxy |
| 2196 | m-D3 | m-D3 | m-D3 | methoxy | Cz |
| 2197 | m-D3 | m-D3 | methoxy | m-D3 | Cz |
| 2198 | m-D3 | m-D3 | methoxy | Cz | m-D3 |
| 2199 | m-D3 | m-D3 | methoxy | m-D3 | methoxy |
| 2200 | methoxy | m-D3 | m-D3 | m-D3 | methoxy |
| 2201 | m-D3 | m-D3 | m-D3 | m-D3 | methoxy |
| 2202 | m-D3 | m-D3 | methoxy | m-D3 | m-D3 |

TABLE 1-40

| No | R¹ | R² | R³ | R⁴ | R⁵ |
|---|---|---|---|---|---|
| 2203 | Cz | m-D1 | Cz | H | m-D2 |
| 2204 | Cz | m-D2 | Cz | H | m-D1 |
| 2205 | m-D1 | Cz | H | m-D2 | Cz |
| 2206 | m-D2 | Cz | H | m-D3 | Cz |
| 2207 | m-D1 | H | m-D2 | H | Cz |
| 2208 | m-D2 | H | m-D3 | H | Cz |
| 2209 | m-D1 | Cz | H | m-D2 | H |
| 2210 | m-D2 | Cz | H | m-D1 | H |
| 2211 | Cz | m-D1 | H | m-D2 | H |
| 2212 | Cz | m-D2 | H | m-D1 | H |
| 2213 | m-D1 | H | m-D2 | Cz | H |
| 2214 | m-D2 | H | m-D3 | H | Cz |
| 2215 | m-D1 | H | m-D2 | H | Cz |
| 2216 | m-D1 | H | m-D3 | H | Cz |
| 2217 | m-D1 | H | Cz | H | m-D2 |
| 2218 | m-D1 | H | Cz | H | m-D3 |
| 2219 | m-D2 | H | Cz | H | m-D3 |
| 2220 | m-D1 | H | H | m-D2 | H |
| 2221 | m-D2 | H | H | m-D3 | H |
| 2222 | H | m-D1 | H | m-D3 | H |
| 2223 | m-D1 | H | H | H | m-D2 |
| 2224 | m-D1 | H | H | H | m-D3 |
| 2225 | m-D2 | H | H | H | m-D3 |
| 2226 | m-D1 | H | m-D2 | H | m-D1 |
| 2227 | m-D2 | H | m-D3 | H | m-D2 |
| 2228 | m-D2 | H | m-D3 | H | m-D2 |
| 2229 | m-D3 | H | m-D2 | H | m-D3 |
| 2230 | m-D1 | m-D2 | m-D3 | H | H |
| 2231 | m-D1 | m-D2 | m-D1 | H | H |
| 2232 | m-D1 | m-D3 | H | m-D3 | H |
| 2233 | m-D1 | m-D2 | H | m-D3 | H |
| 2234 | m-D1 | m-D2 | m-D3 | H | m-D4 |
| 2235 | m-D1 | m-D1 | m-D2 | H | m-D4 |
| 2236 | m-D2 | m-D2 | H | m-D3 | m-D2 |

TABLE 1-41

| No | R¹ | R² | R³ | R⁴ | R⁵ |
|---|---|---|---|---|---|
| 2237 | Cz | Cz | m-D1 | H | phenyl |
| 2238 | H | m-D1 | Cz | Cz | methyl |
| 2239 | m-D1 | H | Cz | metoxy | Cz |

TABLE 1-41-continued

| No | R¹ | R² | R³ | R⁴ | R⁵ |
|---|---|---|---|---|---|
| 2240 | Cz | methyl | m-D1 | phenyl | Cz |
| 2241 | m-D1 | H | Cz | H | methyl |
| 2242 | Cz | methyl | m-D1 | H | H |
| 2243 | methyl | m-D1 | H | Cz | H |
| 2244 | m-D1 | H | m-D1 | Cz | methyl |
| 2245 | m-D1 | methyl | m-D1 | H | Cz |
| 2246 | m-D1 | H | Cz | methoxy | m-D1 |
| 2247 | m-D1 | H | m-D1 | H | methyl |
| 2248 | H | m-D1 | methyl | m-D1 | H |
| 2249 | H | m-D1 | phenyl | m-D1 | H |
| 2250 | m-D1 | H | methyl | H | m-D1 |
| 2251 | m-D1 | H | phenyl | H | m-D1 |
| 2252 | m-D1 | H | methoxy | H | m-D1 |
| 2253 | m-D1 | methyl | phenyl | methoxy | m-D1 |
| 2254 | phenyl | H | m-D1 | H | phneyl |
| 2255 | 4-pyridyl | H | m-D1 | H | 4-pyridyl |
| 2256 | Cz | Cz | m-D2 | H | phenyl |
| 2257 | H | m-D2 | Cz | Cz | methyl |
| 2258 | m-D2 | H | Cz | metoxy | Cz |
| 2259 | Cz | methyl | m-D2 | phenyl | Cz |
| 2260 | m-D2 | H | Cz | H | methyl |
| 2261 | Cz | methyl | m-D2 | H | H |
| 2262 | methyl | m-D2 | H | Cz | H |
| 2263 | m-D2 | H | m-D2 | Cz | methyl |
| 2264 | m-D2 | methyl | m-D2 | H | Cz |
| 2265 | m-D2 | H | Cz | methoxy | m-D2 |
| 2266 | m-D2 | H | m-D2 | H | methyl |
| 2267 | H | m-D2 | methyl | m-D2 | H |
| 2268 | H | m-D2 | phenyl | m-D2 | H |
| 2269 | m-D2 | H | methyl | H | m-D2 |
| 2270 | m-D2 | H | phenyl | H | m-D2 |
| 2271 | m-D2 | H | methoxy | H | m-D2 |
| 2272 | m-D2 | methyl | phenyl | methoxy | m-D2 |
| 2273 | phenyl | H | m-D2 | H | phneyl |
| 2274 | 4-pyridyl | H | m-D2 | H | 4-pyridyl |
| 2275 | Cz | Cz | m-D3 | H | phenyl |
| 2276 | H | m-D3 | Cz | Cz | methyl |
| 2277 | m-D3 | H | Cz | metoxy | Cz |
| 2278 | Cz | methyl | m-D3 | phenyl | Cz |
| 2279 | m-D3 | H | Cz | H | methyl |
| 2280 | Cz | methyl | m-D3 | H | H |
| 2281 | methyl | m-D3 | H | Cz | H |
| 2282 | m-D3 | H | m-D3 | Cz | methyl |
| 2283 | m-D3 | methyl | m-D3 | H | Cz |
| 2284 | m-D3 | H | Cz | methoxy | m-D3 |
| 2285 | m-D3 | H | m-D3 | H | methyl |
| 2286 | H | m-D3 | methyl | m-D3 | H |
| 2287 | H | m-D3 | phenyl | m-D3 | H |
| 2288 | m-D3 | H | methyl | H | m-D3 |
| 2289 | m-D3 | H | phenyl | H | m-D3 |
| 2290 | m-D3 | H | methoxy | H | m-D3 |
| 2291 | m-D3 | methyl | phenyl | methoxy | m-D3 |
| 2292 | phenyl | H | m-D3 | H | phneyl |
| 2293 | 4-pyridyl | H | m-D3 | H | 4-pyridyl |

TABLE 1-42

| No | R¹ | R² | R³ | R⁴ | R⁵ |
|---|---|---|---|---|---|
| 2294 | Cz9 | Cz9 | m-D2 | Cz9 | Cz9 |
| 2295 | m-D2 | Cz9 | Cz9 | Cz9 | H |
| 2296 | Cz9 | Cz9 | Cz9 | m-D2 | H |
| 2297 | m-D2 | Cz9 | Cz9 | H | Cz9 |
| 2298 | Cz9 | Cz9 | Cz9 | m-D2 | Cz9 |
| 2299 | Cz9 | m-D2 | H | Cz9 | Cz9 |
| 2300 | Cz9 | m-D2 | Cz9 | H | H |
| 2301 | Cz9 | Cz9 | m-D2 | H | H |
| 2302 | H | m-D2 | Cz9 | Cz9 | H |
| 2303 | H | Cz9 | m-D2 | Cz9 | H |
| 2304 | m-D2 | H | Cz9 | H | Cz9 |
| 2305 | Cz9 | H | m-D2 | Cz9 | H |
| 2306 | m-D2 | Cz9 | H | H | H |
| 2307 | H | m-D2 | H | Cz9 | H |
| 2308 | m-D2 | m-D2 | Cz9 | H | Cz9 |
| 2309 | m-D2 | Cz9 | m-D2 | H | Cz9 |

TABLE 1-42-continued

| No | R¹ | R² | R³ | R⁴ | R⁵ |
|---|---|---|---|---|---|
| 2310 | Cz9 | m-D2 | m-D2 | H | Cz9 |
| 2311 | m-D2 | m-D2 | H | Cz9 | Cz9 |
| 2312 | Cz9 | m-D2 | H | m-D2 | Cz9 |
| 2313 | m-D2 | Cz9 | m-D2 | H | H |
| 2314 | H | m-D2 | m-D2 | Cz9 | H |
| 2315 | H | m-D2 | Cz9 | m-D2 | H |
| 2316 | m-D2 | H | m-D2 | H | Cz9 |
| 2317 | m-D2 | H | Cz9 | H | m-D2 |
| 2318 | m-D2 | Cz9 | m-D2 | Cz9 | m-D2 |
| 2319 | m-D2 | m-D2 | m-D2 | Cz9 | H |
| 2320 | m-D2 | m-D2 | Cz9 | m-D2 | H |
| 2321 | m-D2 | m-D2 | m-D2 | H | Cz9 |
| 2322 | m-D2 | m-D2 | H | m-D2 | Cz9 |
| 2323 | m-D2 | m-D2 | H | Cz9 | m-D2 |
| 2324 | m-D2 | m-D2 | m-D2 | m-D2 | Cz9 |
| 2325 | Cz9 | Cz9 | m-D3 | Cz9 | Cz9 |
| 2326 | m-D3 | Cz9 | Cz9 | Cz9 | H |
| 2327 | Cz9 | Cz9 | Cz9 | m-D3 | H |
| 2328 | m-D3 | Cz9 | Cz9 | H | Cz9 |
| 2329 | Cz9 | Cz9 | m-D3 | H | Cz9 |
| 2330 | Cz9 | m-D3 | H | Cz9 | Cz9 |
| 2331 | Cz9 | m-D3 | Cz9 | H | H |
| 2332 | Cz9 | Cz9 | m-D3 | H | H |
| 2333 | H | m-D3 | Cz9 | Cz9 | H |
| 2334 | H | Cz9 | m-D3 | Cz9 | H |
| 2335 | m-D3 | H | Cz9 | H | Cz9 |
| 2336 | Cz9 | H | m-D3 | H | Cz9 |
| 2337 | m-D3 | Cz9 | H | H | H |
| 2338 | H | m-D3 | H | Cz9 | H |
| 2339 | m-D3 | m-D3 | Cz9 | H | Cz9 |
| 2340 | m-D3 | Cz9 | Cz9 | H | Cz9 |
| 2341 | Cz9 | m-D3 | m-D3 | H | Cz9 |
| 2342 | m-D3 | m-D3 | H | Cz9 | Cz9 |
| 2343 | Cz9 | m-D3 | H | m-D3 | Cz9 |
| 2344 | m-D3 | Cz9 | m-D3 | H | H |
| 2345 | H | m-D3 | m-D3 | Cz9 | H |
| 2346 | H | m-D3 | Cz9 | m-D3 | H |
| 2347 | m-D3 | H | m-D3 | H | Cz9 |
| 2348 | m-D3 | H | Cz9 | H | m-D3 |
| 2349 | m-D3 | Cz9 | m-D3 | Cz9 | m-D3 |
| 2350 | m-D3 | m-D3 | m-D3 | Cz9 | H |

TABLE 1-43

| No | R¹ | R² | R³ | R⁴ | R⁵ |
|---|---|---|---|---|---|
| 2351 | m-D3 | m-D3 | Cz9 | m-D3 | H |
| 2352 | m-D3 | m-D3 | m-D3 | H | Cz9 |
| 2353 | m-D3 | m-D3 | H | m-D3 | Cz9 |
| 2354 | m-D3 | m-D3 | H | Cz9 | m-D3 |
| 2355 | m-D3 | m-D3 | m-D3 | m-D3 | Cz9 |
| 2356 | Cz10 | m-D2 | Cz10 | m-D2 | Cz10 |
| 2357 | m-D2 | Cz10 | Cz10 | Cz10 | H |
| 2358 | Cz10 | Cz10 | Cz10 | m-D2 | H |
| 2359 | m-D2 | Cz10 | Cz10 | H | Cz10 |
| 2360 | Cz10 | Cz10 | m-D2 | H | Cz10 |
| 2361 | Cz10 | m-D2 | H | Cz10 | Cz10 |
| 2362 | Cz10 | m-D2 | Cz10 | H | H |
| 2363 | Cz10 | Cz10 | m-D2 | H | H |
| 2364 | H | m-D2 | Cz10 | Cz10 | H |
| 2365 | H | Cz10 | m-D2 | Cz10 | H |
| 2366 | m-D2 | H | Cz10 | H | Cz10 |
| 2367 | Cz10 | H | m-D2 | H | Cz10 |
| 2368 | m-D2 | Cz10 | H | H | H |
| 2369 | H | m-D2 | H | Cz10 | H |
| 2370 | m-D2 | m-D2 | Cz10 | H | Cz10 |
| 2371 | m-D2 | Cz10 | m-D2 | H | Cz10 |
| 2372 | Cz10 | m-D2 | m-D2 | H | Cz10 |
| 2373 | m-D2 | m-D2 | H | Cz10 | Cz10 |
| 2374 | Cz10 | m-D2 | H | m-D2 | Cz10 |
| 2375 | m-D2 | Cz10 | m-D2 | H | H |
| 2376 | H | m-D2 | m-D2 | Cz10 | H |
| 2377 | H | m-D2 | Cz10 | m-D2 | H |
| 2378 | m-D2 | H | m-D2 | H | Cz10 |
| 2379 | m-D2 | H | Cz10 | H | m-D2 |
| 2380 | m-D2 | Cz10 | m-D2 | Cz10 | m-D2 |
| 2381 | m-D2 | m-D2 | m-D2 | Cz10 | H |

TABLE 1-43-continued

| No | R¹ | R² | R³ | R⁴ | R⁵ |
|---|---|---|---|---|---|
| 2382 | m-D2 | m-D2 | Cz10 | m-D2 | H |
| 2383 | m-D2 | m-D2 | m-D2 | H | Cz10 |
| 2384 | m-D2 | m-D2 | H | m-D2 | Cz10 |
| 2385 | m-D2 | m-D2 | H | Cz10 | m-D2 |
| 2386 | m-D2 | m-D2 | m-D2 | m-D2 | Cz10 |
| 2387 | Cz10 | Cz10 | m-D3 | Cz10 | Cz10 |
| 2388 | m-D3 | Cz10 | Cz10 | Cz10 | H |
| 2389 | Cz10 | Cz10 | Cz10 | m-D3 | H |
| 2390 | m-D3 | Cz10 | Cz10 | H | Cz10 |
| 2391 | Cz10 | Cz10 | m-D3 | H | Cz10 |
| 2392 | Cz10 | m-D3 | H | Cz10 | Cz10 |
| 2393 | Cz10 | m-D3 | Cz10 | H | H |
| 2394 | Cz10 | Cz10 | m-D3 | H | H |
| 2395 | H | m-D3 | Cz10 | Cz10 | H |
| 2396 | H | Cz10 | m-D3 | Cz10 | H |
| 2397 | m-D3 | H | Cz10 | H | Cz10 |
| 2398 | Cz10 | H | m-D3 | H | Cz10 |
| 2399 | m-D3 | Cz10 | H | H | H |
| 2400 | H | m-D3 | H | Cz10 | H |
| 2401 | m-D3 | m-D3 | Cz10 | H | Cz10 |
| 2402 | m-D3 | Cz10 | m-D3 | H | Cz10 |
| 2403 | Cz10 | m-D3 | m-D3 | H | Cz10 |
| 2404 | m-D3 | m-D3 | H | Cz10 | Cz10 |
| 2405 | Cz10 | m-D3 | H | m-D3 | Cz10 |
| 2406 | m-D3 | Cz10 | m-D3 | H | H |
| 2407 | H | m-D3 | m-D3 | Cz10 | H |
| 2408 | H | m-D3 | Cz10 | m-D3 | H |
| 2409 | m-D3 | H | m-D3 | H | Cz10 |

TABLE 1-44

| No | R¹ | R² | R³ | R⁴ | R⁵ |
|---|---|---|---|---|---|
| 2410 | m-D3 | H | Cz10 | H | m-D3 |
| 2411 | m-D3 | Cz10 | m-D3 | Cz10 | m-D3 |
| 2412 | m-D3 | m-D3 | m-D3 | Cz10 | H |
| 2413 | m-D3 | m-D3 | Cz10 | m-D3 | H |
| 2414 | m-D3 | m-D3 | m-D3 | H | Cz10 |
| 2415 | m-D3 | m-D3 | H | m-D3 | Cz10 |
| 2416 | m-D3 | m-D3 | H | Cz10 | m-D3 |
| 2417 | m-D3 | m-D3 | m-D3 | m-D3 | Cz10 |
| 2418 | Cz11 | Cz11 | m-D2 | Cz11 | Cz11 |
| 2419 | m-D2 | Cz11 | Cz11 | Cz11 | H |
| 2420 | Cz11 | Cz11 | Cz11 | m-D2 | H |
| 2421 | m-D2 | Cz11 | Cz11 | H | Cz11 |
| 2422 | Cz11 | Cz11 | m-D2 | H | Cz11 |
| 2423 | Cz11 | m-D2 | H | Cz11 | Cz11 |
| 2424 | Cz11 | m-D2 | Cz11 | H | H |
| 2425 | Cz11 | Cz11 | m-D2 | H | H |
| 2426 | H | m-D2 | Cz11 | Cz11 | H |
| 2427 | H | Cz11 | m-D2 | Cz11 | H |
| 2428 | m-D2 | H | Cz11 | H | Cz11 |
| 2429 | Cz11 | H | m-D2 | H | Cz11 |
| 2430 | m-D2 | Cz11 | H | H | H |
| 2431 | H | m-D2 | H | Cz11 | H |
| 2432 | m-D2 | m-D2 | Cz11 | H | Cz11 |
| 2433 | m-D2 | Cz11 | m-D2 | H | Cz11 |
| 2434 | Cz11 | m-D2 | m-D2 | H | Cz11 |
| 2435 | m-D2 | m-D2 | H | Cz11 | Cz11 |
| 2436 | Cz11 | m-D2 | H | m-D2 | Cz11 |
| 2437 | m-D2 | Cz11 | m-D2 | H | H |
| 2438 | H | m-D2 | m-D2 | Cz11 | H |
| 2439 | H | m-D2 | Cz11 | m-D2 | H |
| 2440 | m-D2 | H | m-D2 | H | Cz11 |
| 2441 | m-D2 | H | Cz11 | H | m-D2 |
| 2442 | m-D2 | Cz11 | m-D2 | Cz11 | m-D2 |
| 2443 | m-D2 | m-D2 | m-D2 | Cz11 | H |
| 2444 | m-D2 | m-D2 | Cz11 | m-D2 | H |
| 2445 | m-D2 | m-D2 | m-D2 | H | Cz11 |
| 2446 | m-D2 | m-D2 | H | m-D2 | Cz11 |
| 2447 | m-D2 | m-D2 | H | Cz11 | m-D2 |
| 2448 | m-D2 | m-D2 | m-D2 | m-D2 | Cz11 |
| 2449 | Cz11 | Cz11 | m-D3 | Cz11 | Cz11 |
| 2450 | m-D3 | Cz11 | Cz11 | Cz11 | H |
| 2451 | Cz11 | Cz11 | Cz11 | m-D3 | H |
| 2452 | m-D3 | Cz11 | Cz11 | H | Cz11 |
| 2453 | Cz11 | Cz11 | m-D3 | H | Cz11 |
| 2454 | Cz11 | m-D3 | H | Cz11 | Cz11 |
| 2455 | Cz11 | m-D3 | Cz11 | H | H |

TABLE 1-44-continued

| | | | | | |
|---|---|---|---|---|---|
| 2456 | Cz11 | Cz11 | m-D3 | H | H |
| 2457 | H | m-D3 | Cz11 | Cz11 | H |
| 2458 | H | Cz11 | m-D3 | Cz11 | H |
| 2459 | m-D3 | H | Cz11 | H | Cz11 |
| 2460 | Cz11 | H | m-D3 | H | Cz11 |
| 2461 | m-D3 | Cz11 | H | H | H |
| 2462 | H | m-D3 | H | Cz11 | H |
| 2463 | m-D3 | m-D3 | H | Cz11 | Cz11 |
| 2464 | m-D3 | Cz11 | m-D3 | H | Cz11 |
| 2465 | Cz11 | m-D3 | m-D3 | H | Cz11 |
| 2466 | m-D3 | m-D3 | H | Cz11 | Cz11 |
| 2467 | Cz11 | m-D3 | H | m-D3 | Cz11 |
| 2468 | m-D3 | m-D3 | m-D3 | H | H |

TABLE 1-45

| | | | | | |
|---|---|---|---|---|---|
| 2469 | H | m-D3 | m-D3 | Cz11 | H |
| 2470 | H | m-D3 | Cz11 | m-D3 | H |
| 2471 | m-D3 | H | m-D3 | H | Cz11 |
| 2472 | m-D3 | H | Cz11 | H | m-D3 |
| 2473 | m-D3 | Cz11 | m-D3 | Cz11 | m-D3 |
| 2474 | m-D3 | m-D3 | m-D3 | Cz11 | H |
| 2475 | m-D3 | m-D3 | Cz11 | m-D3 | H |
| 2476 | m-D3 | m-D3 | m-D3 | H | Cz11 |
| 2477 | m-D3 | m-D3 | H | m-D3 | Cz11 |
| 2478 | m-D3 | m-D3 | H | Cz11 | m-D3 |
| 2479 | m-D3 | m-D3 | m-D3 | m-D3 | Cz11 |
| 2480 | m-D1 | Cz12 | Cz12 | Cz12 | Cz12 |
| 2481 | Cz12 | m-D1 | Cz12 | Cz12 | Cz12 |
| 2482 | Cz12 | Cz12 | m-D1 | Cz12 | Cz12 |
| 2483 | m-D1 | Cz12 | Cz12 | Cz12 | H |
| 2484 | Cz12 | m-D1 | Cz12 | Cz12 | H |
| 2485 | Cz12 | Cz12 | m-D1 | Cz12 | H |
| 2486 | Cz12 | Cz12 | Cz12 | m-D1 | H |
| 2487 | m-D1 | Cz12 | Cz12 | H | Cz12 |
| 2488 | Cz12 | m-D1 | Cz12 | H | Cz12 |
| 2489 | Cz12 | Cz12 | m-D1 | H | Cz12 |
| 2490 | Cz12 | Cz12 | Cz12 | H | m-D1 |
| 2491 | m-D1 | Cz12 | H | Cz12 | Cz12 |
| 2492 | Cz12 | m-D1 | H | Cz12 | Cz12 |
| 2493 | m-D1 | Cz12 | Cz12 | H | H |
| 2494 | Cz12 | m-D1 | Cz12 | H | H |
| 2495 | Cz12 | Cz12 | m-D1 | H | H |
| 2496 | m-D1 | Cz12 | H | Cz12 | H |
| 2497 | Cz12 | m-D1 | H | Cz12 | H |
| 2498 | Cz12 | Cz12 | H | m-D1 | H |
| 2499 | m-D1 | H | Cz12 | Cz12 | H |
| 2500 | Cz12 | H | m-D1 | Cz12 | H |
| 2501 | Cz12 | H | Cz12 | m-D1 | H |
| 2502 | H | m-D1 | Cz12 | Cz12 | H |
| 2503 | H | Cz12 | m-D1 | Cz12 | H |
| 2504 | m-D1 | Cz12 | H | H | Cz12 |
| 2505 | Cz12 | m-D1 | H | H | Cz12 |
| 2506 | Cz12 | Cz12 | H | H | m-D1 |
| 2507 | m-D1 | H | Cz12 | H | Cz12 |
| 2508 | Cz12 | H | m-D1 | H | Cz12 |
| 2509 | m-D1 | Cz12 | H | H | H |
| 2510 | Cz12 | m-D1 | H | H | H |
| 2511 | m-D1 | H | Cz12 | H | H |
| 2512 | Cz12 | H | m-D1 | H | H |
| 2513 | H | m-D1 | Cz12 | H | H |
| 2514 | H | Cz12 | m-D1 | H | H |
| 2515 | m-D1 | H | H | Cz12 | H |
| 2516 | Cz12 | H | H | m-D1 | H |
| 2517 | H | m-D1 | H | Cz12 | H |
| 2518 | m-D1 | H | H | H | Cz12 |
| 2519 | H | m-D1 | H | Cz12 | H |
| 2520 | m-D1 | Cz12 | m-D1 | Cz12 | H |
| 2521 | m-D1 | Cz12 | m-D1 | H | Cz12 |
| 2522 | Cz12 | m-D1 | Cz12 | m-D1 | H |
| 2523 | Cz12 | m-D1 | Cz12 | H | m-D1 |
| 2524 | Cz12 | m-D1 | m-D1 | Cz12 | H |
| 2525 | m-D1 | m-D1 | Cz12 | H | Cz12 |
| 2526 | m-D1 | m-D1 | Cz12 | Cz12 | H |
| 2527 | m-D1 | Cz12 | Cz12 | H | m-D1 |

TABLE 1-46

| | | | | | |
|---|---|---|---|---|---|
| 2528 | Cz12 | m-D1 | m-D1 | H | Cz12 |
| 2529 | Cz12 | m-D1 | Cz12 | H | m-D1 |
| 2530 | Cz12 | Cz12 | m-D1 | H | m-D1 |
| 2531 | m-D1 | m-D1 | H | Cz12 | Cz12 |
| 2532 | m-D1 | Cz12 | H | Cz12 | m-D1 |
| 2533 | m-D1 | Cz12 | H | m-D1 | Cz12 |
| 2534 | Cz12 | m-D1 | H | m-D1 | Cz12 |
| 2535 | m-D1 | m-D1 | Cz12 | H | H |
| 2536 | m-D1 | Cz12 | m-D1 | H | H |
| 2537 | Cz12 | m-D1 | m-D1 | H | H |
| 2538 | m-D1 | m-D1 | H | Cz12 | H |
| 2539 | m-D1 | Cz12 | H | m-D1 | H |
| 2540 | Cz12 | m-D1 | H | m-D1 | H |
| 2541 | m-D1 | H | m-D1 | Cz12 | H |
| 2542 | m-D1 | H | Cz12 | m-D1 | H |
| 2543 | Cz12 | H | m-D1 | m-D1 | H |
| 2544 | H | m-D1 | Cz12 | m-D1 | H |
| 2545 | H | m-D1 | Cz12 | m-D1 | H |
| 2546 | m-D1 | m-D1 | H | H | Cz12 |
| 2547 | m-D1 | Cz12 | H | H | m-D1 |
| 2548 | Cz12 | m-D1 | H | H | m-D1 |
| 2549 | m-D1 | H | m-D1 | H | Cz12 |
| 2550 | m-D1 | H | Cz12 | H | m-D1 |
| 2551 | m-D1 | m-D1 | m-D1 | Cz12 | Cz12 |
| 2552 | m-D1 | m-D1 | m-D1 | Cz12 | Cz12 |
| 2553 | m-D1 | m-D1 | Cz12 | m-D1 | m-D1 |
| 2554 | m-D1 | Cz12 | m-D1 | Cz12 | m-D1 |
| 2555 | m-D1 | Cz12 | m-D1 | Cz12 | m-D1 |
| 2556 | m-D1 | m-D1 | m-D1 | Cz12 | H |
| 2557 | m-D1 | m-D1 | m-D1 | Cz12 | H |
| 2558 | m-D1 | Cz12 | m-D1 | Cz12 | H |
| 2559 | Cz12 | m-D1 | m-D1 | m-D1 | H |
| 2560 | m-D1 | m-D1 | m-D1 | H | Cz12 |
| 2561 | m-D1 | m-D1 | Cz12 | H | m-D1 |
| 2562 | m-D1 | m-D1 | Cz12 | H | m-D1 |
| 2563 | Cz12 | m-D1 | m-D1 | H | m-D1 |
| 2564 | m-D1 | m-D1 | H | m-D1 | Cz12 |
| 2565 | m-D1 | m-D1 | H | Cz12 | m-D1 |
| 2566 | m-D1 | m-D1 | m-D1 | m-D1 | Cz12 |
| 2567 | m-D1 | m-D1 | m-D1 | Cz12 | m-D1 |
| 2568 | m-D1 | m-D1 | m-D1 | m-D1 | m-D1 |
| 2569 | m-D2 | Cz12 | Cz12 | Cz12 | Cz12 |
| 2570 | Cz12 | m-D2 | Cz12 | Cz12 | Cz12 |
| 2571 | Cz12 | Cz12 | m-D2 | Cz12 | Cz12 |
| 2572 | m-D2 | Cz12 | Cz12 | Cz12 | H |
| 2573 | Cz12 | m-D2 | Cz12 | Cz12 | H |
| 2574 | Cz12 | Cz12 | m-D2 | Cz12 | H |
| 2575 | Cz12 | Cz12 | Cz12 | m-D2 | H |
| 2576 | m-D2 | Cz12 | Cz12 | H | Cz12 |
| 2577 | Cz12 | m-D2 | Cz12 | H | Cz12 |
| 2578 | Cz12 | Cz12 | m-D2 | H | Cz12 |
| 2579 | Cz12 | Cz12 | Cz12 | H | m-D2 |
| 2580 | m-D2 | Cz12 | H | Cz12 | Cz12 |
| 2581 | Cz12 | m-D2 | H | Cz12 | Cz12 |
| 2582 | Cz12 | m-D2 | Cz12 | H | H |
| 2583 | Cz12 | m-D2 | Cz12 | H | H |
| 2584 | Cz12 | Cz12 | m-D2 | H | H |
| 2585 | m-D2 | Cz12 | H | Cz12 | H |
| 2586 | Cz12 | m-D2 | H | Cz12 | H |

TABLE 1-47

| | | | | | |
|---|---|---|---|---|---|
| 2587 | Cz12 | Cz12 | H | m-D2 | H |
| 2588 | m-D2 | H | Cz12 | m-D2 | H |
| 2589 | Cz12 | H | m-D2 | Cz12 | H |
| 2590 | Cz12 | H | Cz12 | m-D2 | H |
| 2591 | H | m-D2 | Cz12 | Cz12 | H |
| 2592 | H | Cz12 | m-D2 | Cz12 | H |
| 2593 | m-D2 | Cz12 | H | H | Cz12 |
| 2594 | m-D2 | Cz12 | H | H | Cz12 |
| 2595 | Cz12 | Cz12 | H | H | m-D2 |
| 2596 | m-D2 | H | Cz12 | H | Cz12 |
| 2597 | Cz12 | H | m-D2 | H | Cz12 |
| 2598 | m-D2 | Cz12 | H | H | H |
| 2599 | Cz12 | m-D2 | H | H | H |
| 2600 | m-D2 | H | Cz12 | H | H |
| 2601 | Cz12 | H | m-D2 | H | H |

TABLE 1-47-continued

| | | | | | |
|---|---|---|---|---|---|
| 2602 | H | m-D2 | Cz12 | H | H |
| 2603 | H | Cz12 | m-D2 | H | H |
| 2604 | m-D2 | H | H | Cz12 | H |
| 2605 | Cz12 | H | H | m-D2 | H |
| 2606 | H | m-D2 | H | Cz12 | H |
| 2607 | m-D2 | H | H | H | Cz12 |
| 2608 | m-D2 | m-D2 | Cz12 | Cz12 | H |
| 2609 | m-D2 | Cz12 | m-D2 | Cz12 | H |
| 2610 | m-D2 | Cz12 | Cz12 | m-D2 | H |
| 2611 | Cz12 | m-D2 | m-D2 | Cz12 | H |
| 2612 | Cz12 | m-D2 | Cz12 | m-D2 | H |
| 2613 | Cz12 | Cz12 | m-D2 | m-D2 | H |
| 2614 | m-D2 | m-D2 | Cz12 | H | Cz12 |
| 2615 | m-D2 | m-D2 | m-D2 | H | Cz12 |
| 2616 | m-D2 | Cz12 | Cz12 | H | m-D2 |
| 2617 | Cz12 | m-D2 | m-D2 | H | Cz12 |
| 2618 | Cz12 | m-D2 | Cz12 | H | m-D2 |
| 2619 | Cz12 | Cz12 | m-D2 | H | m-D2 |
| 2620 | m-D2 | m-D2 | H | Cz12 | Cz12 |
| 2621 | m-D2 | Cz12 | H | m-D2 | Cz12 |
| 2622 | m-D2 | Cz12 | H | Cz12 | m-D2 |
| 2623 | Cz12 | m-D2 | H | m-D2 | Cz12 |
| 2624 | m-D2 | m-D2 | Cz12 | H | H |
| 2625 | m-D2 | Cz12 | m-D2 | H | H |
| 2626 | Cz12 | m-D2 | m-D2 | H | H |
| 2627 | m-D2 | m-D2 | H | Cz12 | H |
| 2628 | m-D2 | Cz12 | H | m-D2 | H |
| 2629 | Cz12 | m-D2 | H | m-D2 | H |
| 2630 | m-D2 | H | m-D2 | Cz12 | H |
| 2631 | m-D2 | H | Cz12 | m-D2 | H |
| 2632 | Cz12 | H | m-D2 | m-D2 | H |
| 2633 | H | m-D2 | m-D2 | Cz12 | H |
| 2634 | H | m-D2 | Cz12 | m-D2 | H |
| 2635 | m-D2 | m-D2 | H | H | Cz12 |
| 2636 | m-D2 | Cz12 | H | H | m-D2 |
| 2637 | Cz12 | m-D2 | H | H | m-D2 |
| 2638 | m-D2 | H | m-D2 | H | Cz12 |
| 2639 | m-D2 | H | Cz12 | H | m-D2 |
| 2640 | m-D2 | m-D2 | m-D2 | Cz12 | Cz12 |
| 2641 | m-D2 | m-D2 | Cz12 | m-D2 | Cz12 |
| 2642 | m-D2 | m-D2 | Cz12 | Cz12 | m-D2 |
| 2643 | m-D2 | Cz12 | m-D2 | m-D2 | Cz12 |
| 2644 | m-D2 | Cz12 | m-D2 | Cz12 | m-D2 |
| 2645 | m-D2 | m-D2 | m-D2 | Cz12 | H |

TABLE 1-48

| | | | | | |
|---|---|---|---|---|---|
| 2646 | m-D2 | m-D2 | Cz12 | m-D2 | H |
| 2647 | m-D2 | Cz12 | m-D2 | m-D2 | H |
| 2648 | Cz12 | m-D2 | m-D2 | m-D2 | H |
| 2649 | m-D2 | m-D2 | m-D2 | H | Cz12 |
| 2650 | m-D2 | m-D2 | Cz12 | H | m-D2 |
| 2651 | m-D2 | Cz12 | m-D2 | H | m-D2 |
| 2652 | Cz12 | m-D2 | m-D2 | H | m-D2 |
| 2653 | m-D2 | m-D2 | H | m-D2 | Cz12 |
| 2654 | m-D2 | m-D2 | H | Cz12 | m-D2 |
| 2655 | m-D2 | Cz12 | m-D2 | m-D2 | Cz12 |
| 2656 | m-D2 | m-D2 | m-D2 | Cz12 | m-D2 |
| 2657 | m-D2 | m-D2 | Cz12 | m-D2 | m-D2 |
| 2658 | m-D3 | Cz12 | Cz12 | Cz12 | Cz12 |
| 2659 | Cz12 | m-D3 | Cz12 | Cz12 | Cz12 |
| 2660 | Cz12 | Cz12 | m-D3 | Cz12 | Cz12 |
| 2661 | m-D3 | Cz12 | Cz12 | Cz12 | H |
| 2662 | m-D3 | Cz12 | Cz12 | Cz12 | H |
| 2663 | Cz12 | Cz12 | m-D3 | Cz12 | H |
| 2664 | Cz12 | Cz12 | Cz12 | m-D3 | H |
| 2665 | m-D3 | Cz12 | Cz12 | H | Cz12 |
| 2666 | m-D3 | Cz12 | Cz12 | H | Cz12 |
| 2667 | Cz12 | Cz12 | m-D3 | H | Cz12 |
| 2668 | Cz12 | Cz12 | Cz12 | H | m-D3 |
| 2669 | m-D3 | Cz12 | H | Cz12 | Cz12 |
| 2670 | m-D3 | Cz12 | H | Cz12 | Cz12 |
| 2671 | m-D3 | Cz12 | Cz12 | H | H |
| 2672 | Cz12 | Cz12 | m-D3 | H | H |
| 2673 | Cz12 | Cz12 | Cz12 | m-D3 | H |
| 2674 | m-D3 | Cz12 | H | Cz12 | H |
| 2675 | Cz12 | m-D3 | H | Cz12 | H |

TABLE 1-48-continued

| | | | | | |
|---|---|---|---|---|---|
| 2676 | Cz12 | Cz12 | H | m-D3 | H |
| 2677 | m-D3 | H | Cz12 | Cz12 | H |
| 2678 | Cz12 | H | m-D3 | Cz12 | H |
| 2679 | Cz12 | H | Cz12 | m-D3 | H |
| 2680 | H | m-D3 | Cz12 | Cz12 | H |
| 2681 | H | Cz12 | m-D3 | Cz12 | H |
| 2682 | m-D3 | Cz12 | H | H | Cz12 |
| 2683 | Cz12 | m-D3 | H | H | Cz12 |
| 2684 | Cz12 | Cz12 | H | H | m-D3 |
| 2685 | m-D3 | H | Cz12 | H | Cz12 |
| 2686 | Cz12 | H | m-D3 | H | Cz12 |
| 2687 | m-D3 | Cz12 | H | H | H |
| 2688 | Cz12 | m-D3 | H | H | H |
| 2689 | m-D3 | H | Cz12 | H | H |
| 2690 | Cz12 | H | m-D3 | H | H |
| 2691 | H | m-D3 | Cz12 | H | H |
| 2692 | H | Cz12 | m-D3 | H | H |
| 2693 | m-D3 | H | H | Cz12 | H |
| 2694 | Cz12 | H | H | m-D3 | H |
| 2695 | H | m-D3 | H | Cz12 | H |
| 2696 | m-D3 | H | H | H | Cz12 |
| 2697 | m-D3 | m-D3 | Cz12 | Cz12 | H |
| 2698 | m-D3 | Cz12 | m-D3 | Cz12 | H |
| 2699 | m-D3 | Cz12 | Cz12 | m-D3 | H |
| 2700 | Cz12 | m-D3 | m-D3 | Cz12 | H |
| 2701 | Cz12 | m-D3 | Cz12 | m-D3 | H |
| 2702 | Cz12 | Cz12 | m-D3 | m-D3 | H |
| 2703 | m-D3 | m-D3 | Cz12 | H | Cz12 |
| 2704 | m-D3 | Cz12 | m-D3 | H | Cz12 |

TABLE 1-49

| | | | | | |
|---|---|---|---|---|---|
| 2705 | m-D3 | Cz12 | Cz12 | H | m-D3 |
| 2706 | Cz12 | m-D3 | m-D3 | H | Cz12 |
| 2707 | Cz12 | m-D3 | Cz12 | H | m-D3 |
| 2708 | Cz12 | Cz12 | m-D3 | H | m-D3 |
| 2709 | m-D3 | m-D3 | H | Cz12 | Cz12 |
| 2710 | m-D3 | Cz12 | H | m-D3 | Cz12 |
| 2711 | m-D3 | Cz12 | H | Cz12 | m-D3 |
| 2712 | Cz12 | m-D3 | H | m-D3 | Cz12 |
| 2713 | m-D3 | m-D3 | Cz12 | H | H |
| 2714 | m-D3 | Cz12 | m-D3 | H | H |
| 2715 | Cz12 | m-D3 | m-D3 | H | H |
| 2716 | m-D3 | m-D3 | H | Cz12 | H |
| 2717 | m-D3 | Cz12 | H | m-D3 | H |
| 2718 | Cz12 | m-D3 | H | m-D3 | H |
| 2719 | m-D3 | H | m-D3 | Cz12 | H |
| 2720 | m-D3 | H | Cz12 | m-D3 | H |
| 2721 | Cz12 | H | m-D3 | m-D3 | H |
| 2722 | H | m-D3 | m-D3 | Cz12 | H |
| 2723 | H | m-D3 | Cz12 | m-D3 | H |
| 2724 | m-D3 | m-D3 | H | H | Cz12 |
| 2725 | m-D3 | Cz12 | H | H | m-D3 |
| 2726 | Cz12 | m-D3 | H | H | m-D3 |
| 2727 | m-D3 | H | m-D3 | H | Cz12 |
| 2728 | m-D3 | H | Cz12 | H | m-D3 |
| 2729 | m-D3 | m-D3 | m-D3 | Cz12 | Cz12 |
| 2730 | m-D3 | m-D3 | Cz12 | m-D3 | Cz12 |
| 2731 | m-D3 | m-D3 | Cz12 | Cz12 | m-D3 |
| 2732 | m-D3 | Cz12 | m-D3 | m-D3 | Cz12 |
| 2733 | m-D3 | Cz12 | m-D3 | Cz12 | m-D3 |
| 2734 | m-D3 | Cz12 | Cz12 | m-D3 | m-D3 |
| 2735 | m-D3 | m-D3 | m-D3 | Cz12 | H |
| 2736 | m-D3 | m-D3 | Cz12 | m-D3 | H |
| 2737 | Cz12 | m-D3 | m-D3 | m-D3 | H |
| 2738 | m-D3 | m-D3 | m-D3 | H | Cz12 |
| 2739 | m-D3 | m-D3 | Cz12 | H | m-D3 |
| 2740 | m-D3 | Cz12 | m-D3 | H | m-D3 |
| 2741 | Cz12 | m-D3 | m-D3 | H | m-D3 |
| 2742 | m-D3 | m-D3 | H | m-D3 | Cz12 |
| 2743 | m-D3 | m-D3 | H | Cz12 | m-D3 |
| 2744 | m-D3 | Cz12 | m-D3 | m-D3 | Cz12 |
| 2745 | m-D3 | m-D3 | Cz12 | m-D3 | m-D3 |
| 2746 | m-D3 | m-D3 | m-D3 | m-D3 | m-D3 |

TABLE 1-50

| No | $R^1$ | $R^2$ | $R^3$ | $R^4$ | $R^5$ |
|---|---|---|---|---|---|
| 2747 | F | Cz | m-D1 | Cz | Cz |
| 2748 | Cz | F | m-D1 | Cz | Cz |
| 2749 | Cz | F | m-D1 | F | Cz |
| 2750 | Cz | F | m-D1 | F | F |
| 2751 | Cz | F | m-D1 | Cz | H |
| 2752 | Cz | F | m-D1 | F | H |
| 2753 | F | Cz | m-D1 | Cz | H |
| 2754 | F | F | m-D1 | Cz | H |
| 2755 | F | Cz | m-D1 | H | Cz |
| 2756 | Cz | F | m-D1 | H | Cz |
| 2757 | F | F | m-D1 | H | Cz |
| 2758 | F | Cz | m-D1 | H | F |
| 2759 | F | H | m-D1 | H | Cz |
| 2760 | F | Cz | m-D2 | Cz | Cz |
| 2761 | Cz | F | m-D2 | Cz | Cz |
| 2762 | Cz | F | m-D2 | F | Cz |
| 2763 | Cz | F | m-D2 | F | F |
| 2764 | Cz | F | m-D2 | Cz | H |
| 2765 | Cz | F | m-D2 | F | H |
| 2766 | F | Cz | m-D2 | Cz | H |
| 2767 | F | F | m-D2 | Cz | H |
| 2768 | F | Cz | m-D2 | H | Cz |
| 2769 | Cz | F | m-D2 | H | Cz |
| 2770 | F | F | m-D2 | H | Cz |
| 2771 | F | Cz | m-D2 | H | F |
| 2772 | F | H | m-D2 | H | Cz |
| 2773 | F | Cz | m-D3 | Cz | Cz |
| 2774 | Cz | F | m-D3 | Cz | Cz |
| 2775 | Cz | F | m-D3 | F | Cz |
| 2776 | Cz | F | m-D3 | F | F |
| 2777 | Cz | F | m-D3 | Cz | H |
| 2778 | Cz | F | m-D3 | F | H |
| 2779 | F | Cz | m-D3 | Cz | H |
| 2780 | F | F | m-D3 | Cz | H |
| 2781 | F | Cz | m-D3 | H | Cz |
| 2782 | Cz | F | m-D3 | H | Cz |
| 2783 | F | F | m-D3 | H | Cz |
| 2784 | F | Cz | m-D3 | H | F |
| 2785 | F | H | m-D3 | H | Cz |

The molecular weight of the compound represented by the general formula (1) is preferably 1,500 or less, more preferably 1,200 or less, further preferably 1,000 or less, and still further preferably 800 or less, for example, in the case where an organic layer containing the compound represented by the general formula (1) is intended to be formed as a film by a vapor deposition method. The lower limit of the molecular weight is the molecular weight of the smallest compound represented by the general formula (1).

The compound represented by the general formula (1) may be formed into a film by a coating method irrespective of the molecular weight thereof. The compound that has a relatively large molecular weight may be formed into a film by a coating method.

As an application of the present invention, it may be considered that a compound that contains plural structures each represented by the general formula (1) in the molecule is used as a light-emitting material.

For example, it may be considered that a polymerizable group is introduced in advance to the structure represented by the general formula (1), and a polymer obtained by polymerizing the polymerizable group is used as a light-emitting material. Specifically, it may be considered that a monomer that has a polymerizable functional group at any of $R^1$ to $R^5$ in the general formula (1) is prepared, and is homopolymerized or copolymerized with another monomer to prepare a polymer containing repeating units, and the polymer is used as a light-emitting material. In alternative, it may be considered that the compounds represented by the general formula (1) are coupled with each other to form a dimer or a trimer, and the dimer or the trimer is used as a light-emitting material.

Examples of the polymer having the repeating unit containing the structure represented by the general formula (1) include a polymer containing a structure represented by the following general formula (11) or (12).

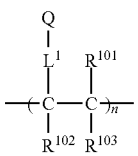

General Formula (11)

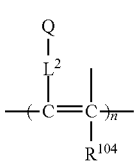

General Formula (12)

In the general formulae (11) and (12), Q represents a group containing the structure represented by the general formula (1), and $L^1$ and $L^2$ each represent a linking group. The linking group preferably has a number of carbon atoms of from 0 to 20, more preferably from 1 to 15, and further preferably from 2 to 10. The linking group preferably has a structure represented by —$X^{11}$-$L^{11}$-, wherein $X^{11}$ represents an oxygen atom or a sulfur atom, and preferably an oxygen atom, and $L^{11}$ represents a linking group, preferably a substituted or unsubstituted alkylene group or a substituted or unsubstituted arylene group, and more preferably a substituted or unsubstituted alkylene group having from 1 to 10 carbon atoms or a substituted or unsubstituted phenylene group.

In the general formulae (11) and (12), $R^{101}$, $R^{102}$, $R^{103}$ and $R^{104}$ each independently represent a substituent, preferably a substituted or unsubstituted alkyl group having from 1 to 6 carbon atoms, a substituted or unsubstituted alkoxy group having from 1 to 6 carbon atoms, or a halogen atom, more preferably an unsubstituted alkyl group having from 1 to 3 carbon atoms, an unsubstituted alkoxy group having from 1 to 3 carbon atoms, a fluorine atom, or a chlorine atom, and further preferably an unsubstituted alkyl group having from 1 to 3 carbon atoms or an unsubstituted alkoxy group having from 1 to 3 carbon atoms.

The linking group represented by $L^1$ and $L^2$ may be bonded to any of $R^1$ to $R^5$ of the structure of the general formula (1) constituting Q. Two or more of the linking groups may be boded to one group represented by Q to form a crosslinked structure or a network structure.

Specific examples of the structure of the repeating unit include structures represented by the following formulae (13) to (16).

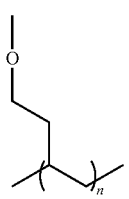

Formula (13)

Formula (14)

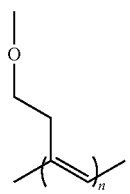

Formula (15)

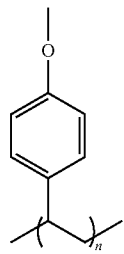

Formula (16)

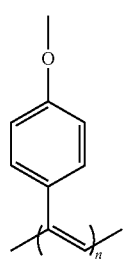

The polymer having the repeating unit containing the structure represented by any of the formulae (13) to (16) may be synthesized in such a manner that a hydroxyl group is introduced to any of $R^1$ to $R^5$ in the structure represented by the general formula (1), and the hydroxyl group as a linker is reacted with the following compound to introduce a polymerizable group thereto, followed by polymerizing the polymerizable group.

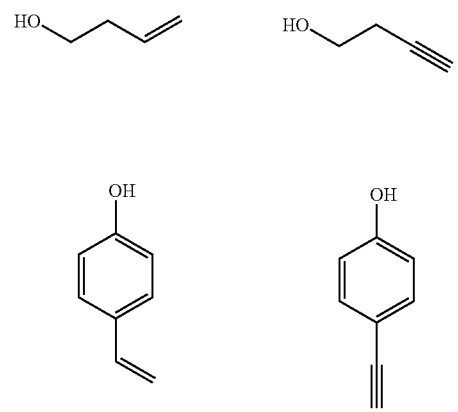

The polymer containing the structure represented by the general formula (1) in the molecule may be a polymer containing only a repeating unit having the structure represented by the general formula (1), or a polymer further containing a repeating unit having another structure. The repeating unit having the structure represented by the general formula (1) contained in the polymer may be only one kind or two or more kinds. Examples of the repeating unit that does not have the structure represented by the general formula (1) include a repeating unit derived from a monomer that is used for ordinary copolymerization. Examples of the repeating unit include a repeating unit derived from a monomer having an ethylenic unsaturated bond, such as ethylene and styrene.

Synthesis Method of Compound Represented by General Formula (1)

The compound represented by the general formula (1) is a novel compound.

The compound represented by the general formula (1) may be synthesized by combining the known reactions. For example, the compound represented by the general formula (1), wherein $R^1$ and $R^5$ each represent an unsubstituted 9-carbazolyl group, an unsubstituted 10-phenoxazyl group or an unsubstituted 10-phenothiazyl group, and $R^3$ represents a 9-carbazolyl group having substitutes at the 1-position, the 3-position, the 6-position and the 8-position, a 10-phenoxazyl group having substitutes at the 1-position, the 3-position, the 7-position and the 9-position or a 10-phenothiazyl group having substitutes at the 1-position, the 3-position, the 7-position and the 9-position, may be synthesized by following reactions (I), (II).

(I)

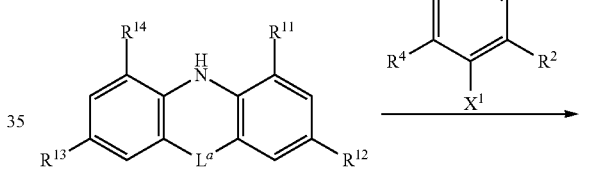

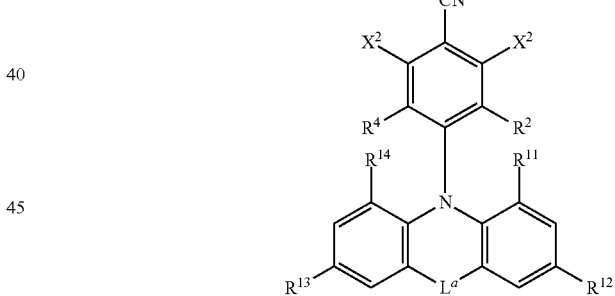

(II)

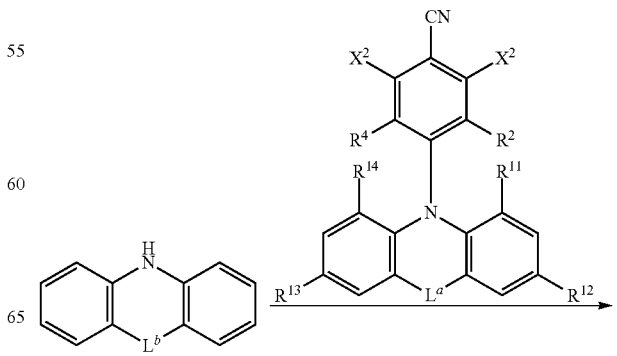

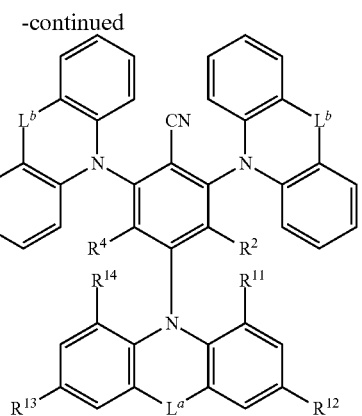

For the descriptions of $R^2$ and $R^4$ in the aforementioned reaction scheme, reference may be made to the corresponding description in the general formula (1). $R^{11}$ to $R^{14}$ each independently represent a substituent. $L^a$ and $L^b$ each represent a single bond, an oxygen atom, or a sulfur atom. $X^1$ and $X^2$ each independently represent a halogen atom, examples of which include a fluorine atom, a chlorine atom, a bromine atom, and an iodine atom, and $X^1$ is preferably a bromine atom, and $X^2$ is preferably a fluorine atom.

The aforementioned reaction is an application of the known coupling reaction, and the known reaction conditions may be appropriately selected and used. For the details of the reaction, reference may be made to Synthesis Examples described later. The compound represented by the general formula (1) may be synthesized by combining the other known synthesis reactions.

Organic Light-emitting Device

The compound represented by the general formula (1) of the invention is useful as a light-emitting material of an organic light-emitting device. Accordingly, the compound represented by the general formula (1) of the invention may be effectively used as a light-emitting material in a light-emitting layer of an organic light-emitting device. The compound represented by the general formula (1) may also be used as a host or assist dopant.

The compound represented by the general formula (1) includes a delayed fluorescent material emitting delayed fluorescent light. Therefore, the invention provides an invention relating to a delayed fluorescent material having a structure represented by the general formula (1), an invention relating to use of the compound represented by the general formula (1) as a delayed fluorescent material, and an invention relating to a method for emitting delayed fluorescent light with the compound represented by the general formula (1). An organic light-emitting device that uses the compound as a light-emitting material has features that the device emits delayed fluorescent light and has a high light emission efficiency. The principle of the features may be described as follows for an organic electroluminescent device as an example.

In an organic electroluminescent device, carriers are injected from both an anode and a cathode to a light-emitting material to form an excited state for the light-emitting material, with which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy use efficiency. However, the excited triplet state has a long lifetime and thus causes saturation of the excited state and deactivation of energy through mutual action with the excitons in the excited triplet state, and therefore the quantum yield of phosphorescence may generally be often not high. On the other hand, a delayed fluorescent material emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. It is considered that a thermal activation type delayed fluorescent material emitting light through absorption of thermal energy is particularly useful for an organic electroluminescent device. In the case where a delayed fluorescent material is used in an organic electroluminescent device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

The use of the compound represented by the general formula (1) of the invention as a light-emitting material of a light-emitting layer may provide an excellent organic light-emitting device, such as an organic photoluminescent device (organic PL device) and an organic electroluminescent device (organic EL device). The organic photoluminescent device has a structure containing a substrate having formed thereon at least a light-emitting layer. The organic electroluminescent device has a structure containing at least an anode, a cathode, and an organic layer formed between the anode and the cathode. The organic layer contains at least a light-emitting layer, and may be formed only of a light-emitting layer, or may have one or more organic layer in addition to the light-emitting layer. Examples of the organic layer include a hole transporting layer, a hole injection layer, an electron barrier layer, a hole barrier layer, an electron injection layer, an electron transporting layer, and an exciton barrier layer. The hole transporting layer may be a hole injection and transporting layer having a hole injection function, and the electron transporting layer may be an electron injection and transporting layer having an electron injection function. A specific structural example of an organic electroluminescent device is shown in FIG. 1. In FIG. 1, the numeral 1 denotes a substrate, 2 denotes an anode, 3 denotes a hole injection layer, 4 denotes a hole transporting layer, 5 denotes a light-emitting layer, 6 denotes an electron transporting layer, and 7 denotes a cathode.

The members and the layers of the organic electroluminescent device will be described below. The descriptions for the substrate and the light-emitting layer may also be applied to the substrate and the light-emitting layer of the organic photoluminescent device.

Substrate

The organic electroluminescent device of the invention is preferably supported by a substrate. The substrate is not particularly limited and may be one that has been commonly used in an organic electroluminescent device, and examples thereof used include those formed of glass, transparent plastics, quartz and silicon.

Anode

The anode of the organic electroluminescent device used is preferably formed of, as an electrode material, a metal, an alloy, or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 µm or more), the pattern may be formed with a mask having a desired shape on vapor deposition or sputtering of the electrode material. In alternative, in the case where a material capable of being coated, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred ohm per square or less. The thickness of the anode may be generally selected from a range of from 10 to 1,000 nm, and preferably from 10 to 200 nm, while depending on the material used.

Cathode

The cathode is preferably formed of as an electrode material a metal (which is referred to as an electron injection metal), an alloy, or an electroconductive compound, having a small work function (4 eV or less), or a mixture thereof. Specific examples of the electrode material include sodium, a sodium-potassium alloy, magnesium, lithium, a magnesium-copper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, is preferred from the standpoint of the electron injection property and the durability against oxidation and the like. The cathode may be produced by forming the electrode material into a thin film by such a method as vapor deposition or sputtering. The cathode preferably has a sheet resistance of several hundred ohm per square or less, and the thickness thereof may be generally selected from a range of from 10 nm to 5 µm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light-emitting Layer

The light-emitting layer is a layer, in which holes and electrons injected from the anode and the cathode respectively are recombined to form excitons, and then the layer emits light. A light-emitting material may be solely used as the light-emitting layer, but the light-emitting layer preferably contains a light-emitting material and a host material. The light-emitting material used may be one kind or two or more kinds selected from the group of compounds represented by the general formula (1) of the invention. In order that the organic electroluminescent device and the organic photoluminescent device of the invention exhibit a high light emission efficiency, it is important that the singlet excitons and the triplet excitons generated in the light-emitting material are confined in the light-emitting material. Accordingly, a host material is preferably used in addition to the light-emitting material in the light-emitting layer. The host material used may be an organic compound that has excited singlet energy and excited triplet energy, at least one of which is higher than those of the light-emitting material of the invention. As a result, the singlet excitons and the triplet excitons generated in the light-emitting material of the invention are capable of being confined in the molecules of the light-emitting material of the invention, thereby eliciting the light emission efficiency thereof sufficiently. Even though the singlet excitons and the triplet excitons are not confined sufficiently, a high light emission efficiency may be obtained in some cases, and thus a host material that is capable of achieving a high light emission efficiency may be used in the invention without any particular limitation. In the organic light-emitting device and the organic electroluminescent device of the invention, the light emission occurs in the light-emitting material of the invention contained in the light-emitting layer. The emitted light contains both fluorescent light and delayed fluorescent light. However, a part of the emitted light may contain emitted light from the host material, or the emitted light may partially contain emitted light from the host material.

In the case where the host material is used, the amount of the compound of the invention as the light-emitting material contained in the light-emitting layer is preferably 0.1% by weight or more, and more preferably 1% by weight or more, and is preferably 50% by weight or less, more preferably 20% by weight or less, and further preferably 10% by weight or less.

The host material in the light-emitting layer is preferably an organic compound that has a hole transporting capability and an electron transporting capability, prevents the emitted light from being increased in wavelength, and has a high glass transition temperature.

Injection Layer

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transporting layer and between the cathode and the light-emitting layer or the electron transporting layer. The injection layer may be provided depending on necessity.

Barrier Layer

The barrier layer is a layer that is capable of inhibiting charges (electrons or holes) and/or excitons present in the light-emitting layer from being diffused outside the light-emitting layer. The electron barrier layer may be disposed between the light-emitting layer and the hole transporting layer, and inhibits electrons from passing through the light-emitting layer toward the hole transporting layer. Similarly, the hole barrier layer may be disposed between the light-emitting layer and the electron transporting layer, and inhibits holes from passing through the light-emitting layer toward the electron transporting layer. The barrier layer may also be used for inhibiting excitons from being diffused outside the light-emitting layer. Accordingly, the electron barrier layer and the hole barrier layer each may also have a function as an exciton barrier layer. The electron barrier layer or the exciton barrier layer referred in the description herein is intended to include a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons and holes in the light-emitting layer. As the material for the hole barrier layer, the materials for the electron transporting layer described later may be used depending on necessity.

Electron Barrier Layer

The electron barrier layer has the function of transporting holes in a broad sense. The electron barrier layer has a function of inhibiting electrons from reaching the hole transporting layer while transporting holes, and thereby enhances the recombination probability of electrons and holes in the light-emitting layer.

Exciton Barrier Layer

The exciton barrier layer is a layer for inhibiting excitons generated through the recombination of holes and electrons in the light-emitting layer from being diffused to the charge transporting layer, and the use of the layer inserted enables effective confinement of excitons in the light-emitting layer, and thereby enhances the light emission efficiency of the device. The exciton barrier layer may be inserted adjacent to the light-emitting layer on any of the side of the anode and the side of the cathode, and on both the sides. Specifically, in the case where the exciton barrier layer is present on the side of the anode, the layer may be inserted between the hole transporting layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton barrier layer that is adjacent to the light-emitting layer on the side of the anode, a hole injection layer, an electron barrier layer, and the like may be provided, and between the cathode and the exciton barrier layer that is adjacent to the light-emitting layer on the side of the cathode, an electron injection layer, an electron transporting layer, a hole barrier layer, and the like may be provided. In the case where the barrier layer is provided, the material used for the barrier layer preferably has excited singlet energy and excited triplet energy, at least one of which is higher than the excited singlet energy and the excited triplet energy of the light-emitting layer, respectively.

Hole Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that can be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer, and an electroconductive polymer oligomer, particularly a thiophene oligomer. Among these, a porphyrin compound, an aromatic tertiary amine compound, and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) suffices to have a function of transporting electrons, which are injected from the cathode, to the light-emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and an anthrone derivative, and an oxadiazole derivative. Further, regarding the aforementioned oxadiazole derivative, the electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescent device, the compound represented by the general formula (1) may be used not only in one layer of an organic layer (for example, an electron transporting layer), but also in plural organic layers. In this case, the compounds represented by the general formula (1) used in the organic layers may be the same as or different from each other. For example, the compound represented by the general formula (1) may be used in the injection layer, the barrier layer, the hole barrier layer, the electron barrier layer, the exciton barrier layer, the hole transporting layer, and the like, in addition to the electron transporting layer and the light-emitting layer. The film forming methods of the layers are not particularly limited, and the layers may be produced by any of a dry process and a wet process.

Specific examples of the preferred materials that may be used in the organic electroluminescent device are shown below, but the materials that may be used in the invention are not construed as being limited to the example compounds below. The compound that is shown as a material having a particular function may also be used as a material having another function. In the following structural formulae of the example compounds, R, R', and $R_1$ to $R_{10}$ each independently represent a hydrogen atom or a substituent, X represents a carbon atom or a hetero atom forming a ring skeleton, n represents an integer of from 3 to 5, Y represents a substituent, and m represents an integer of 0 or more.

Preferred examples of a compound that may also be used as the host material of the light-emitting layer are shown below.

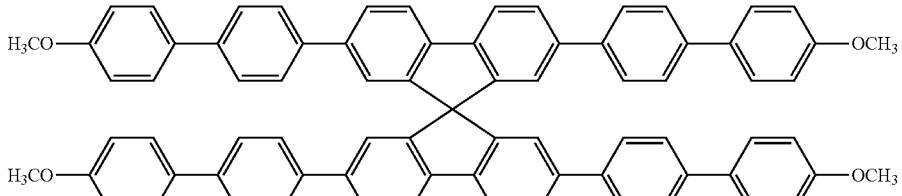

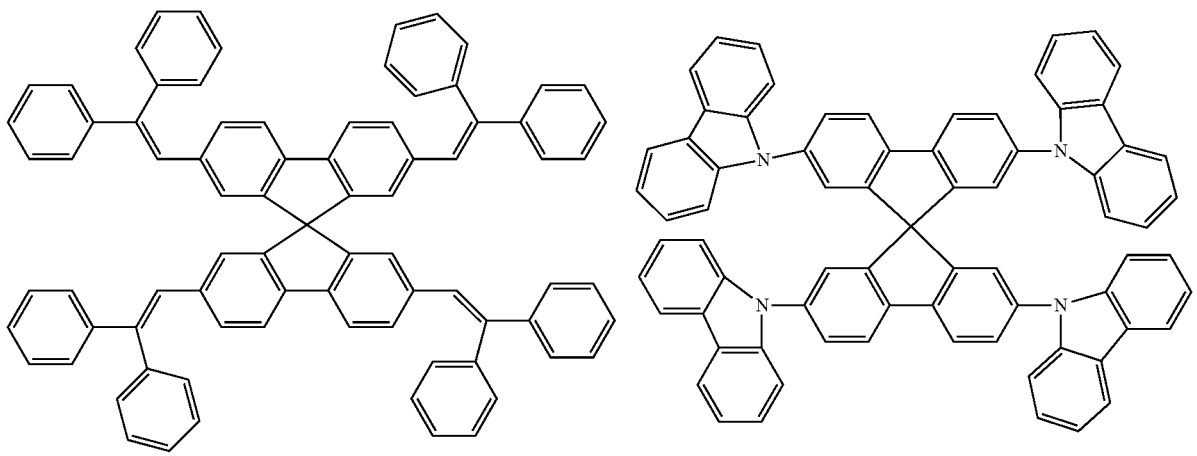

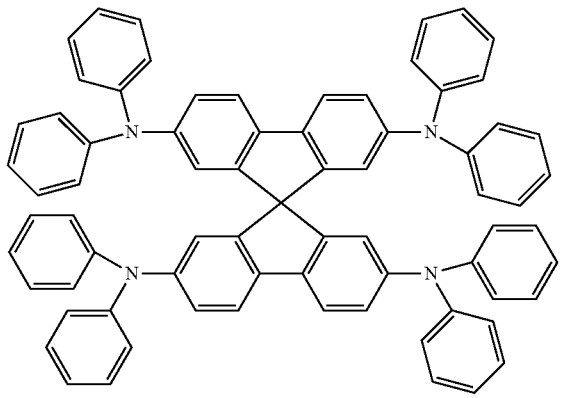

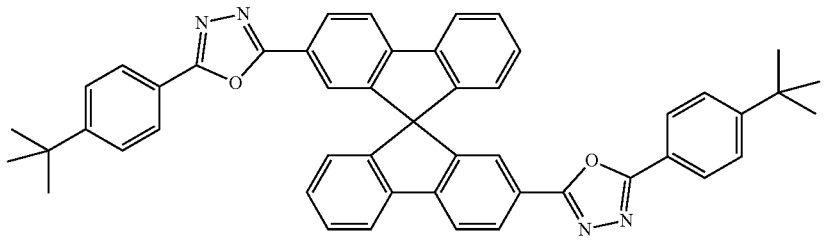

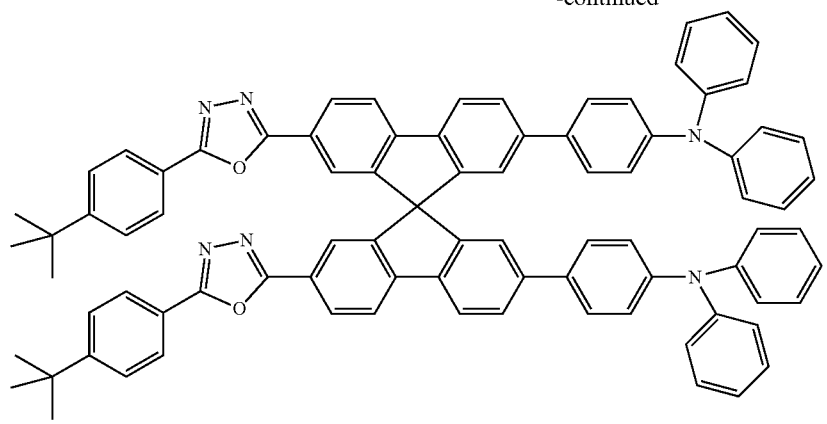
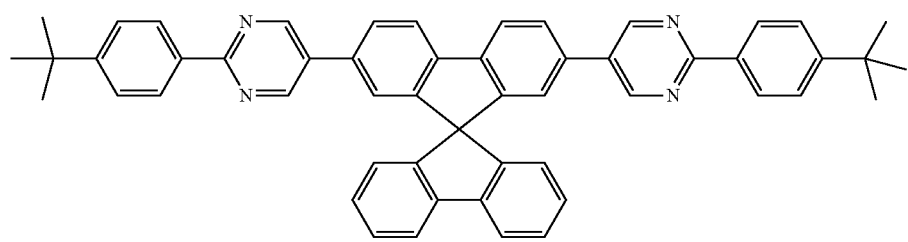
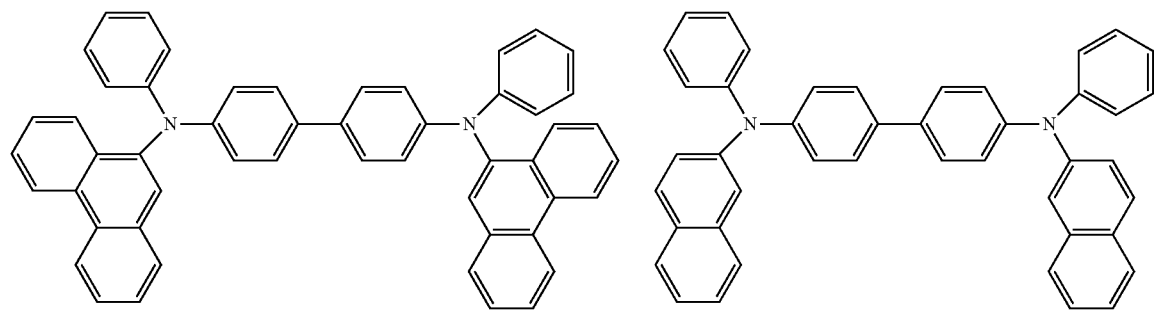
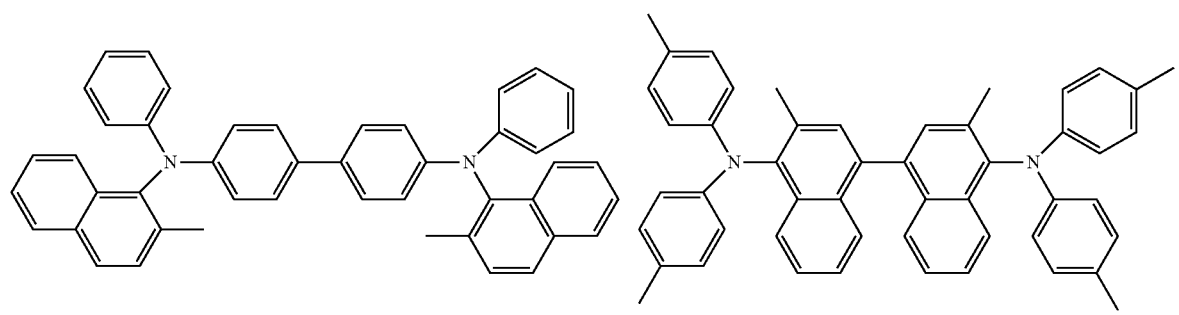

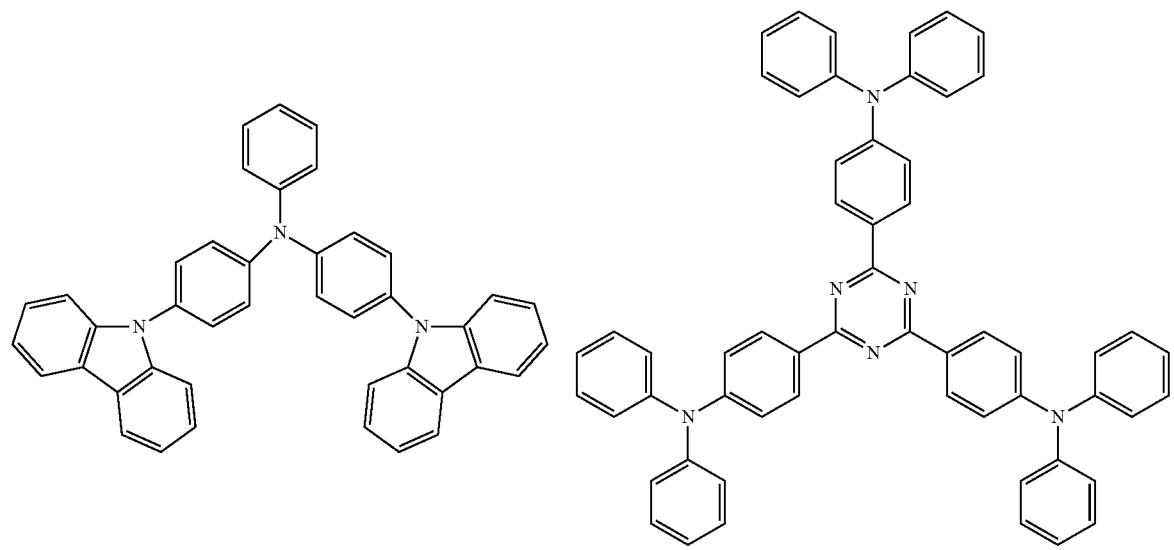
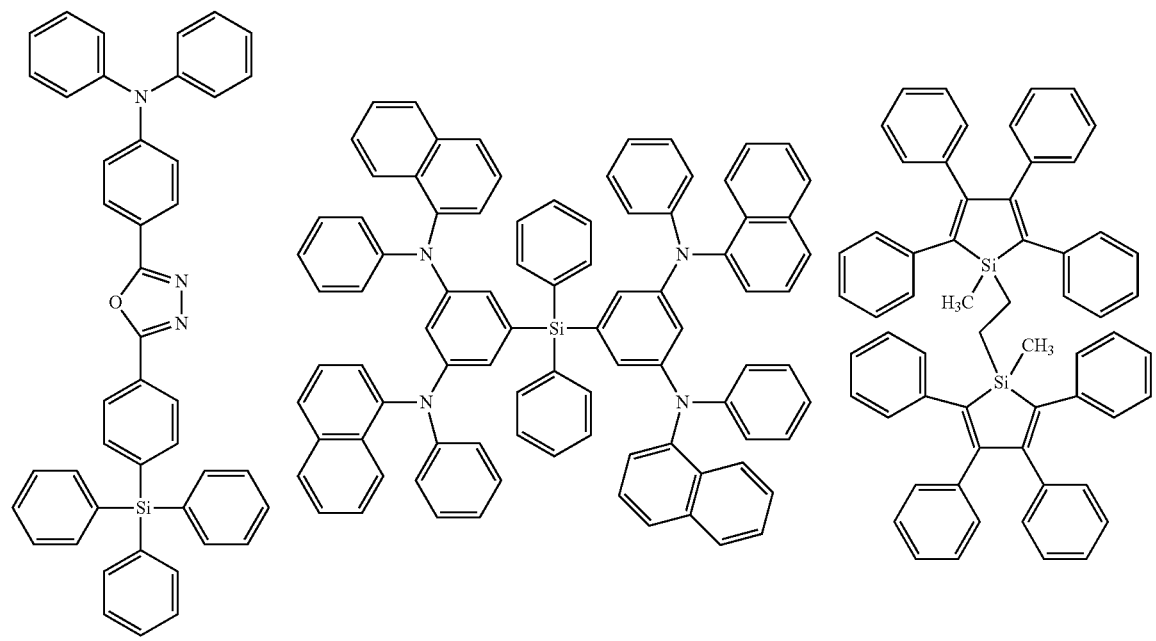
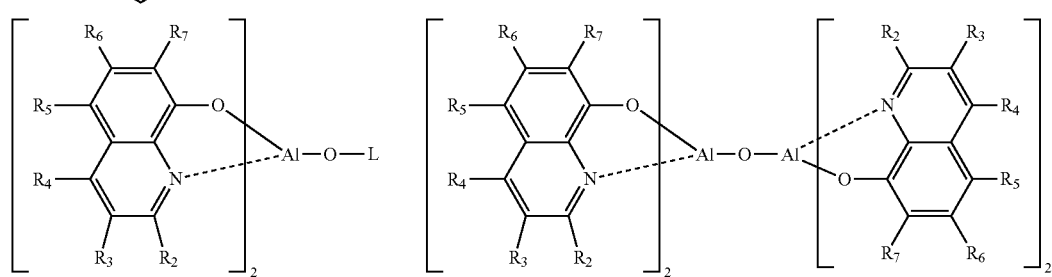
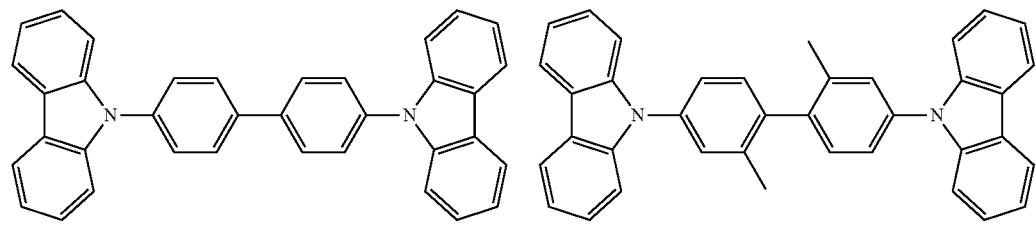

-continued
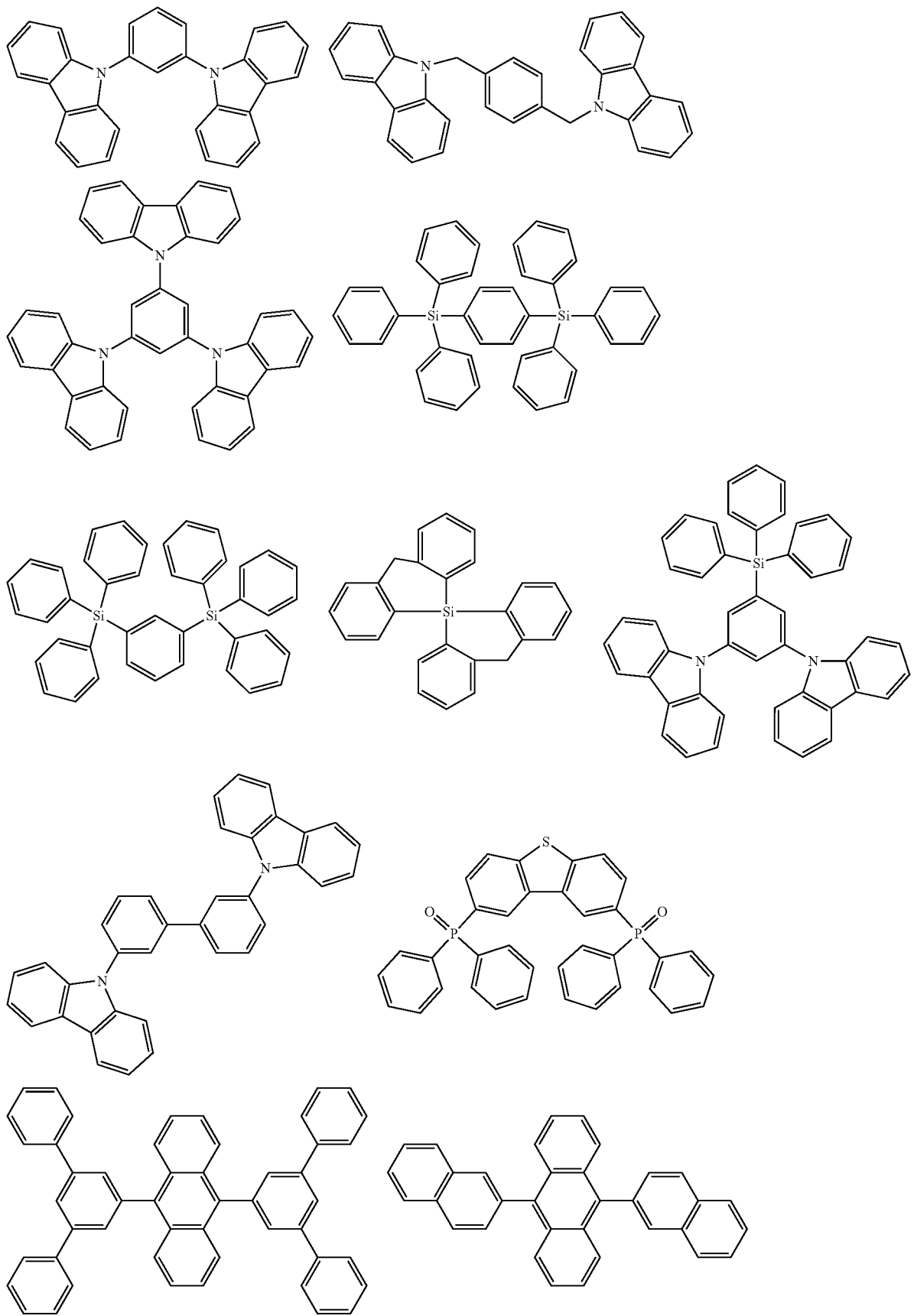

-continued
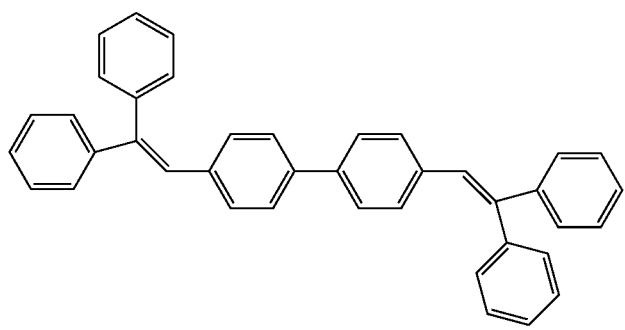
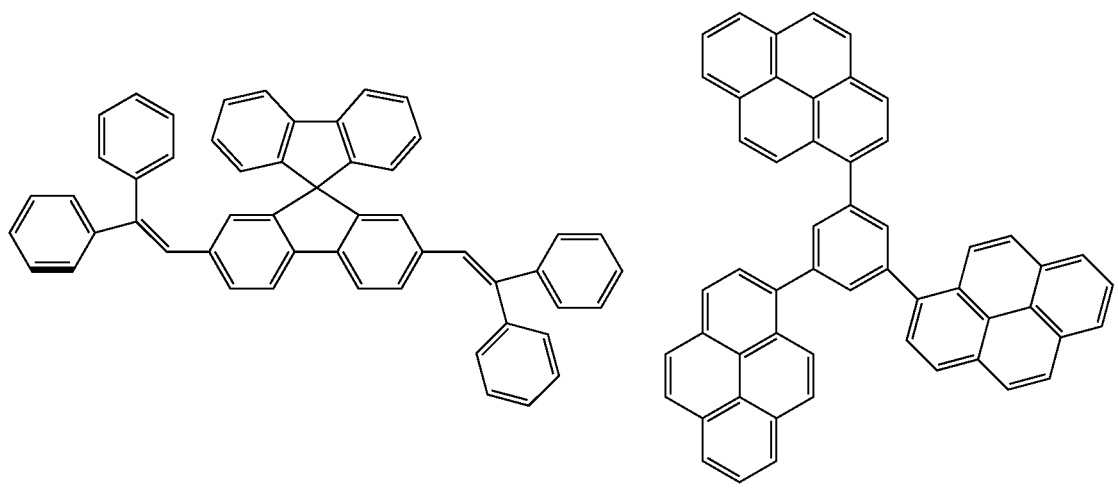
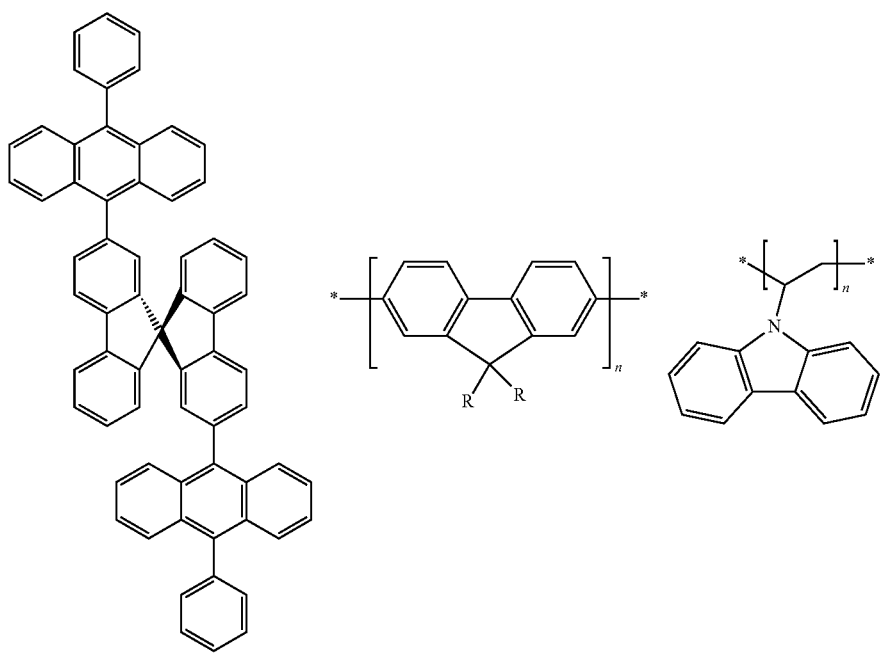

-continued
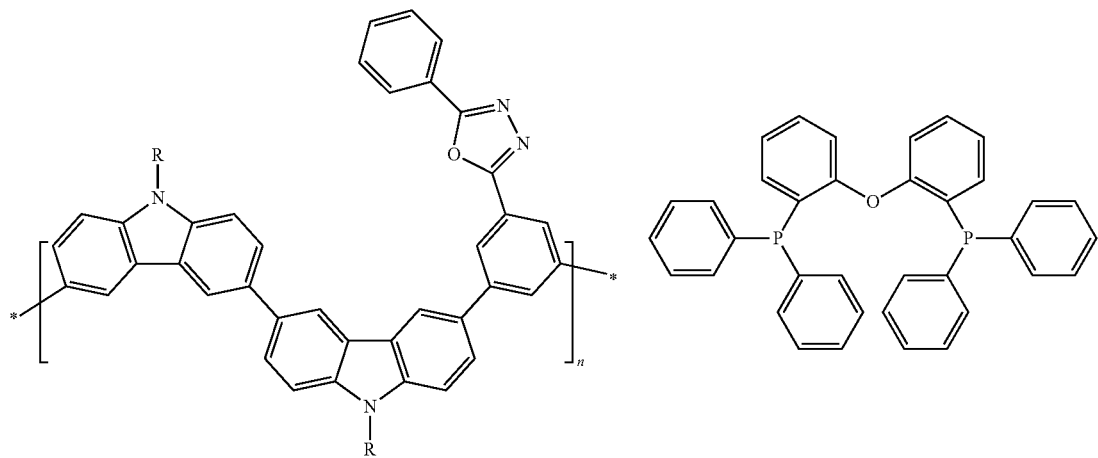
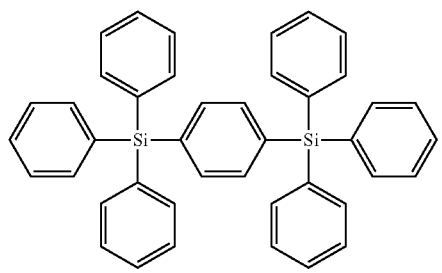
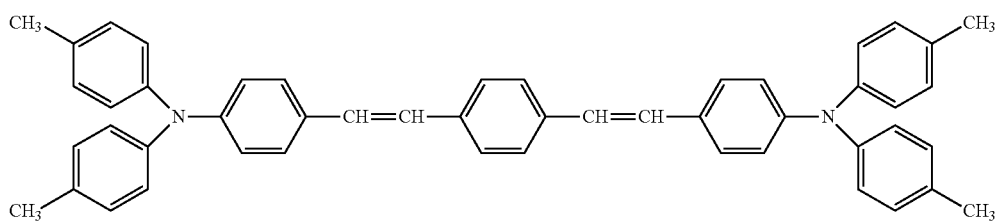
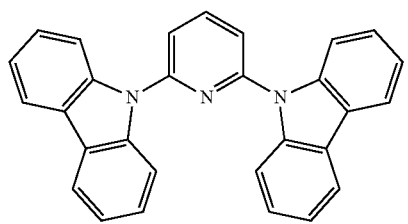

Preferred examples of a compound that may be used as the hole injection material are shown below.
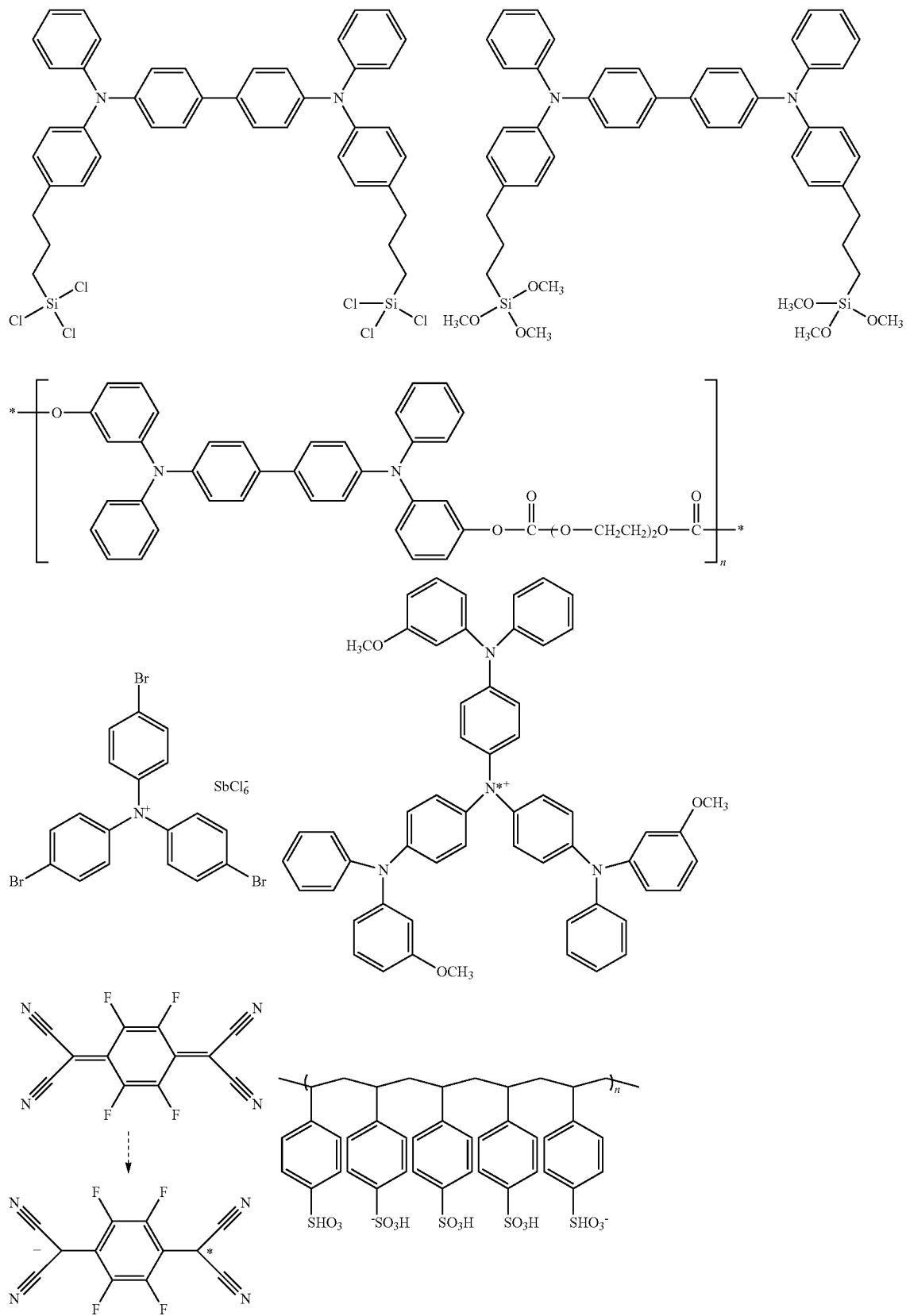

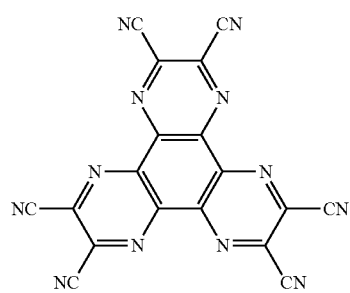 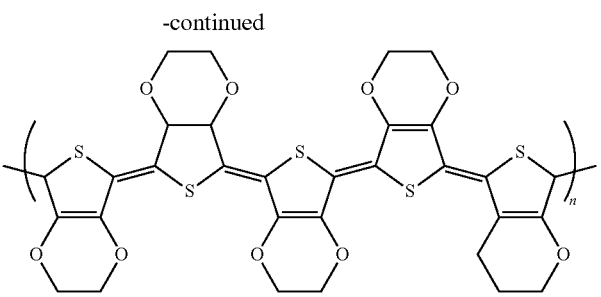
Preferred examples of a compound that may be used as the hole transporting material are shown below.
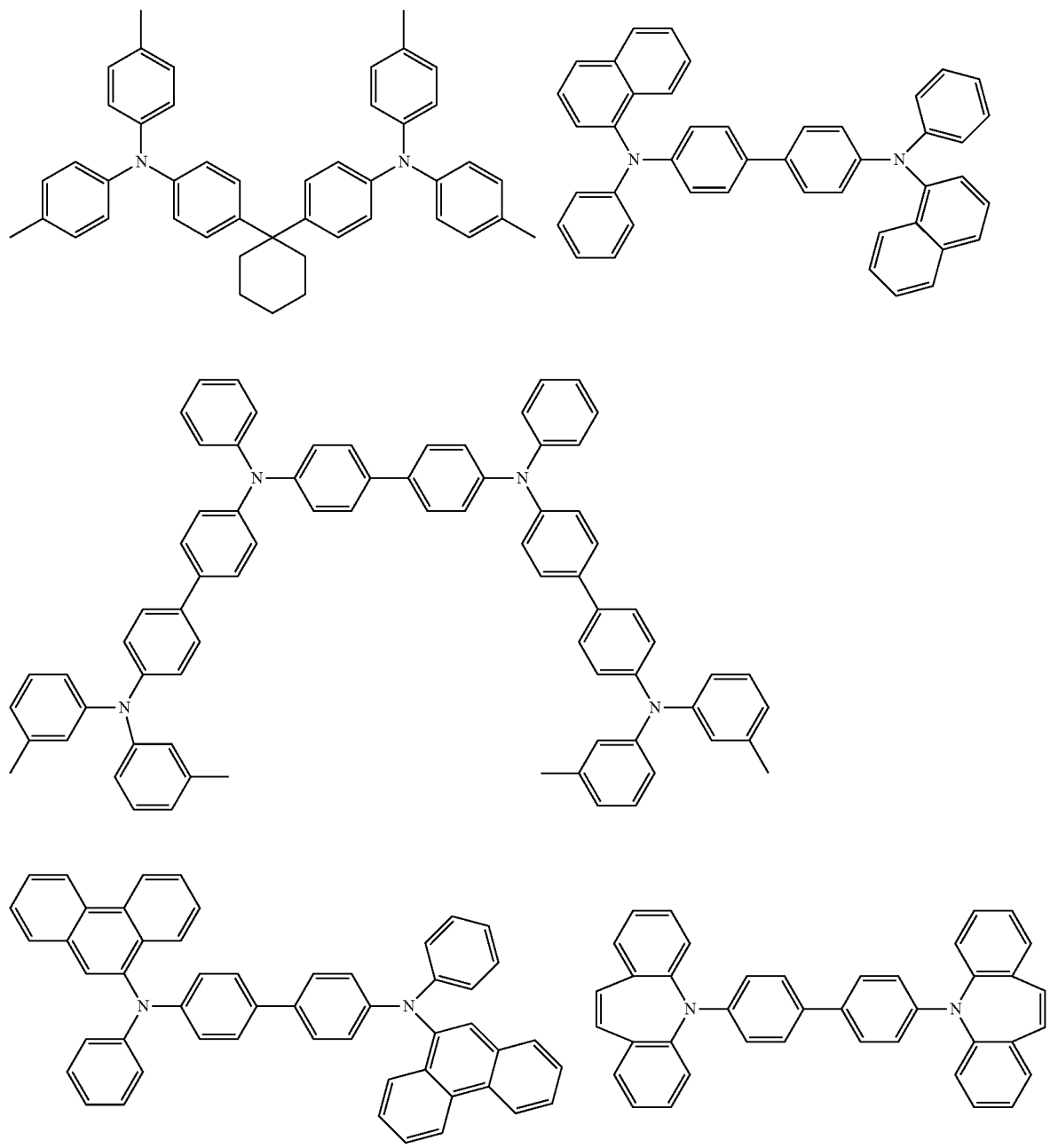

-continued
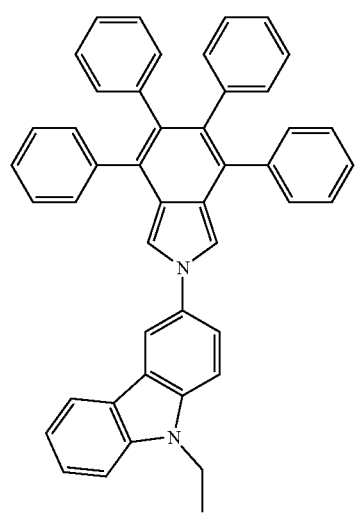
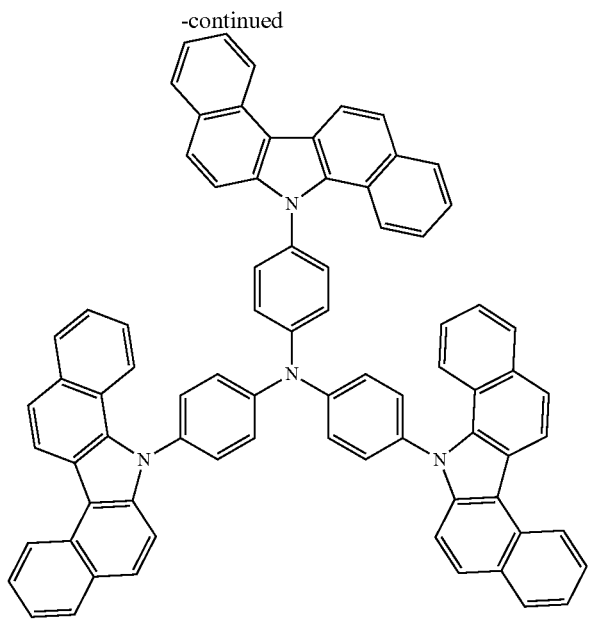
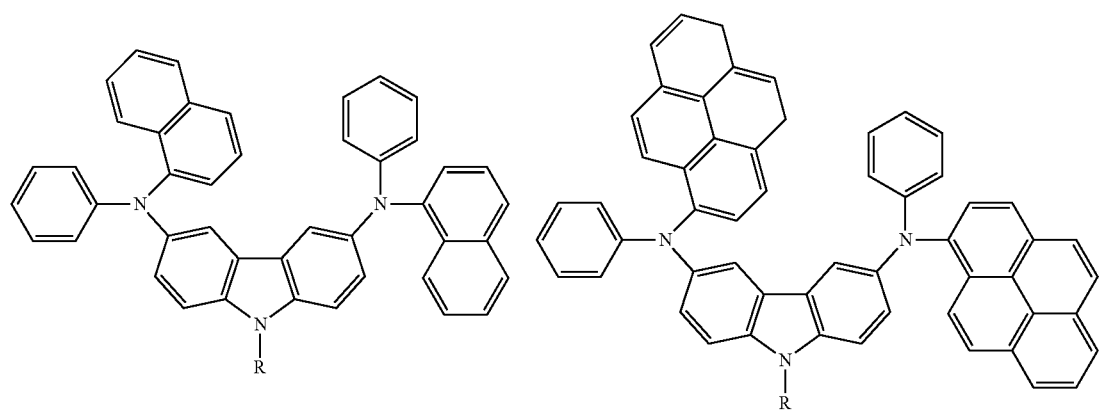
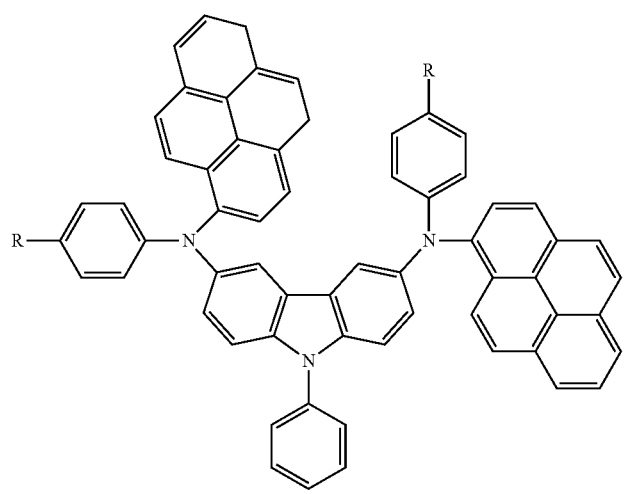

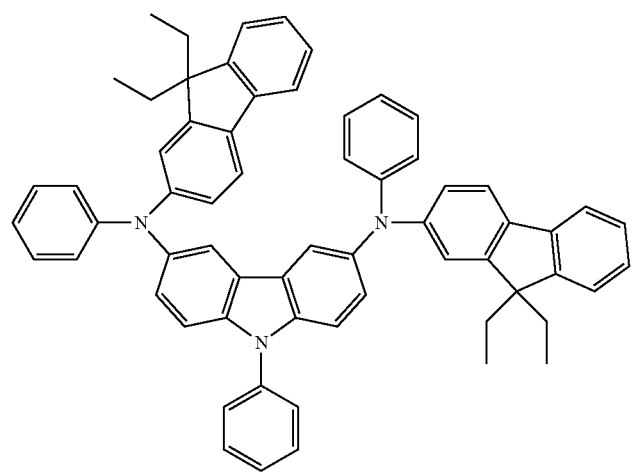
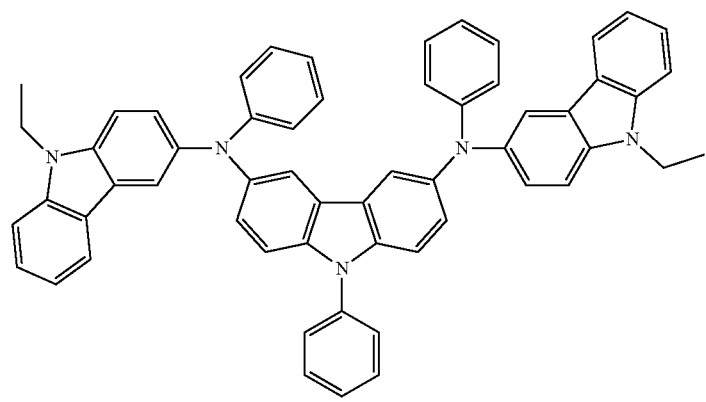
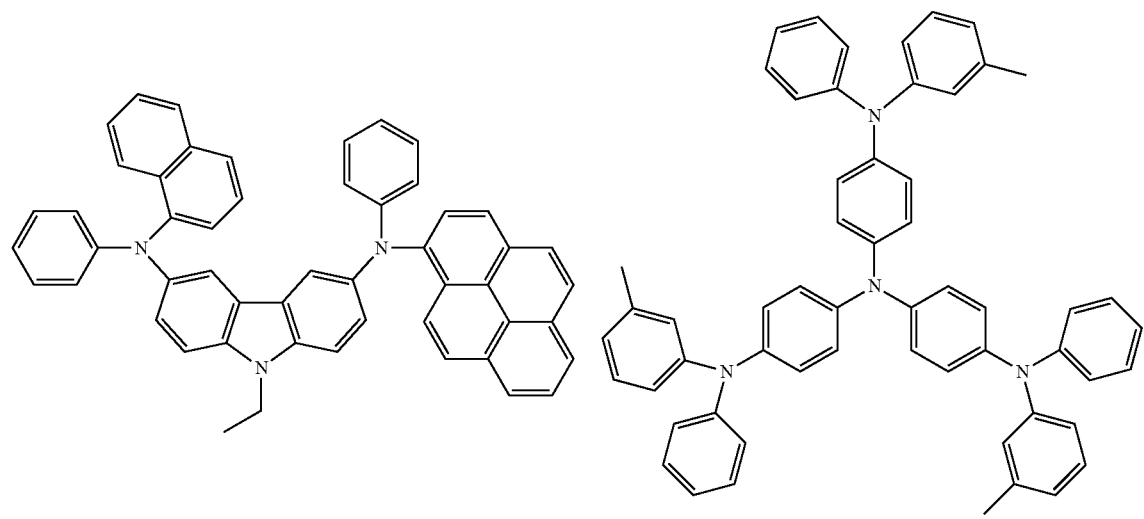

81
82
-continued
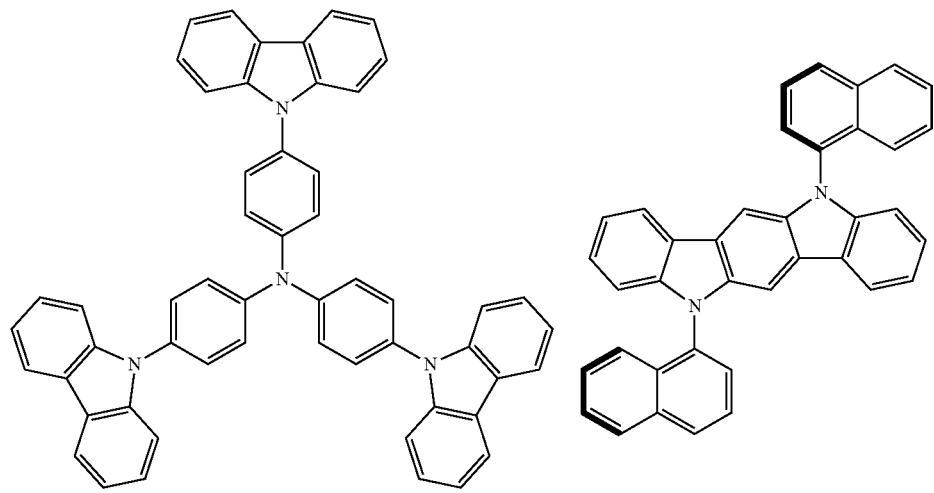
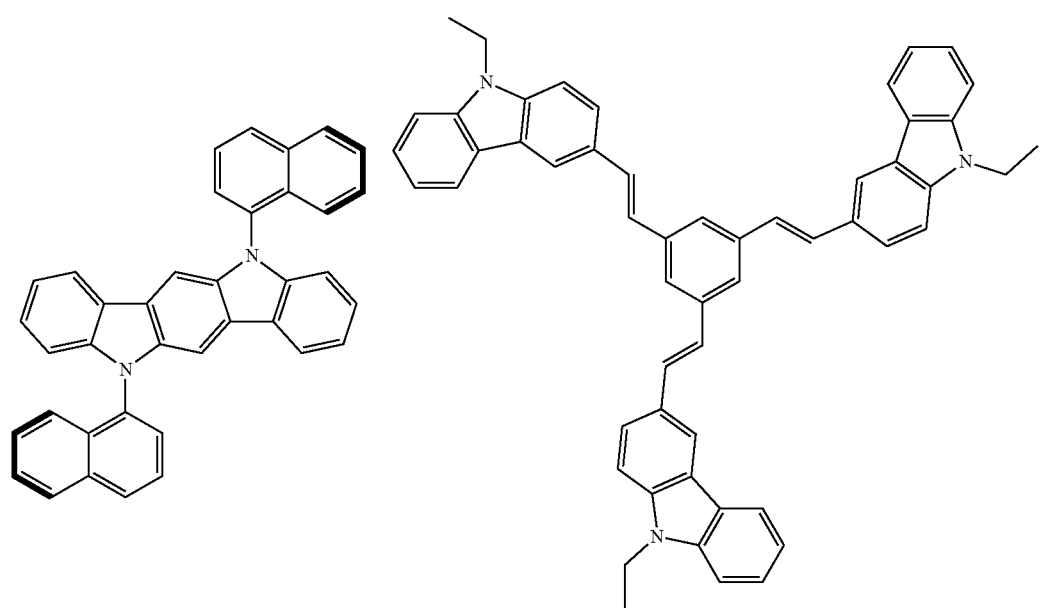

-continued
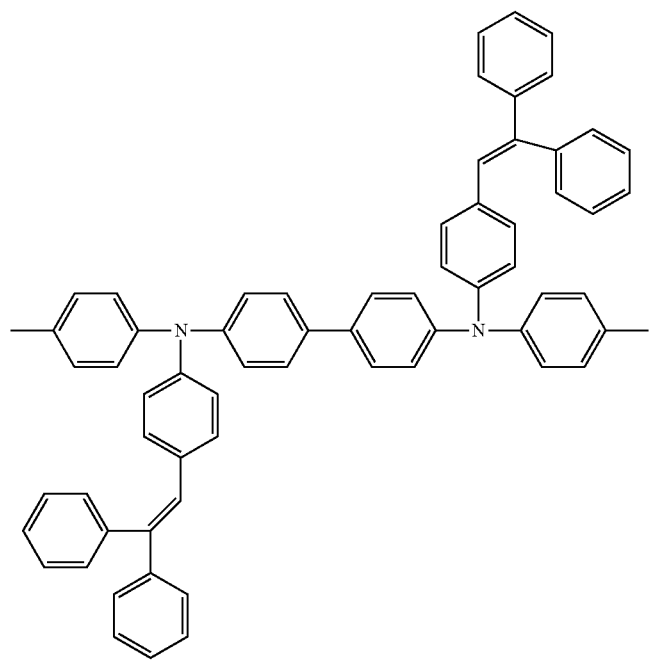
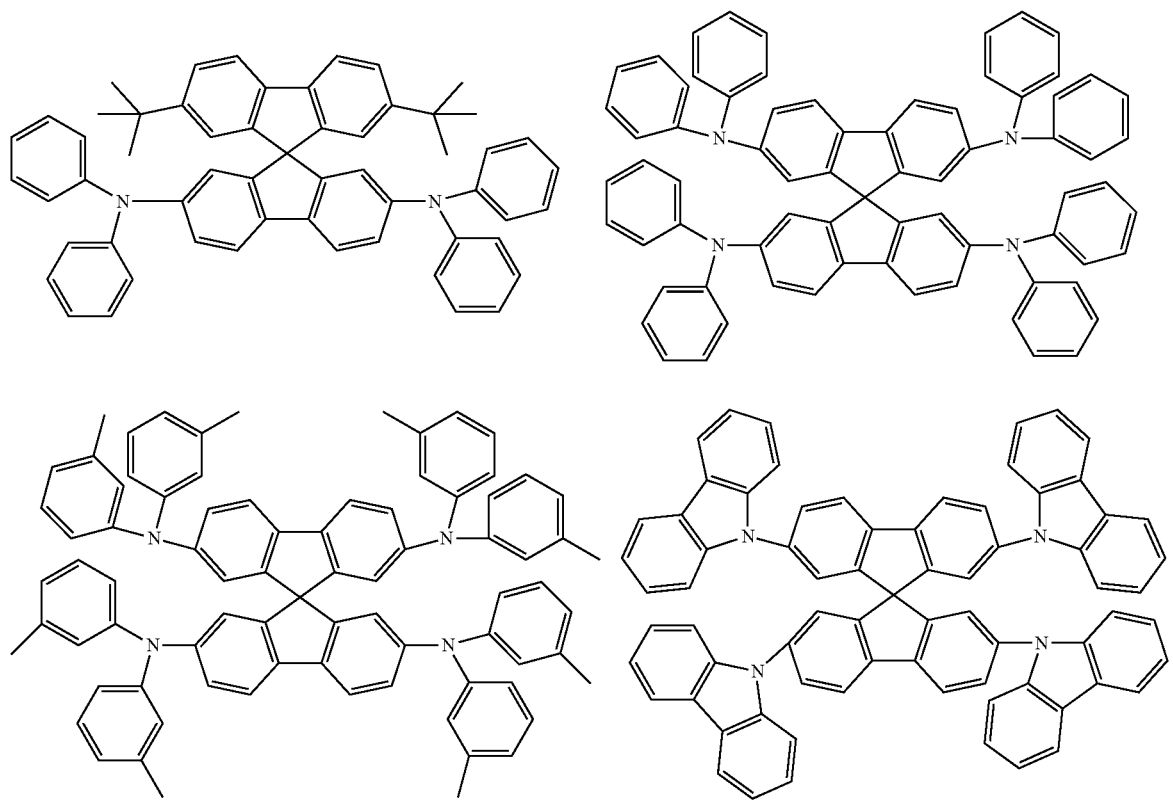
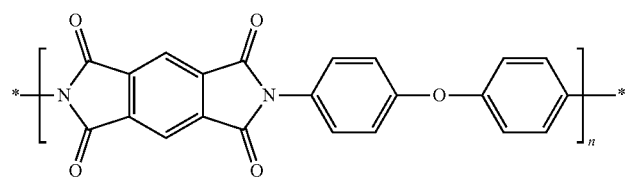

-continued
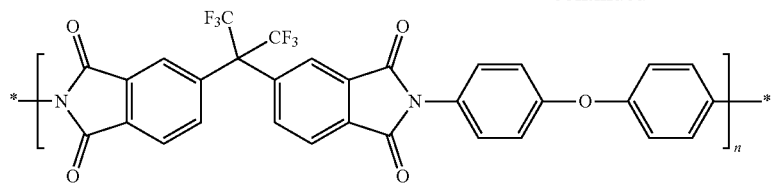
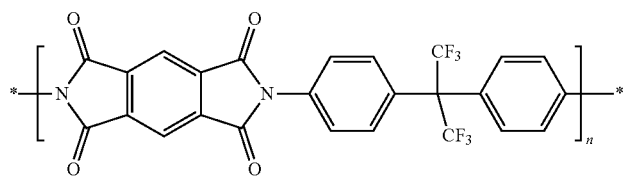
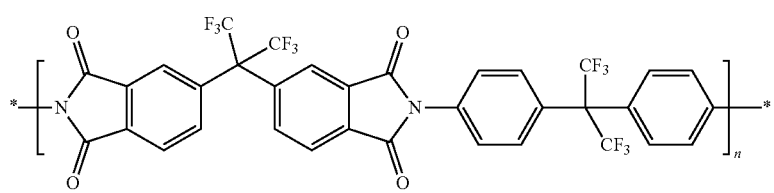
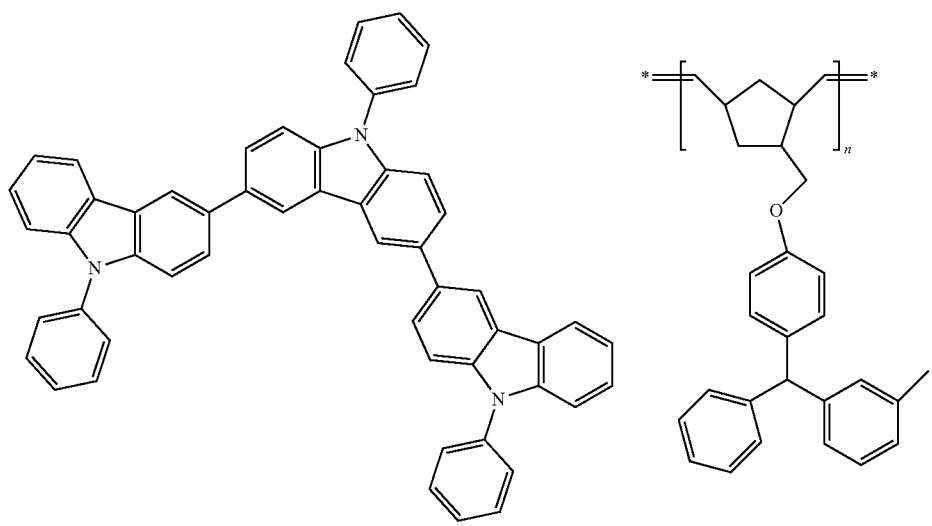
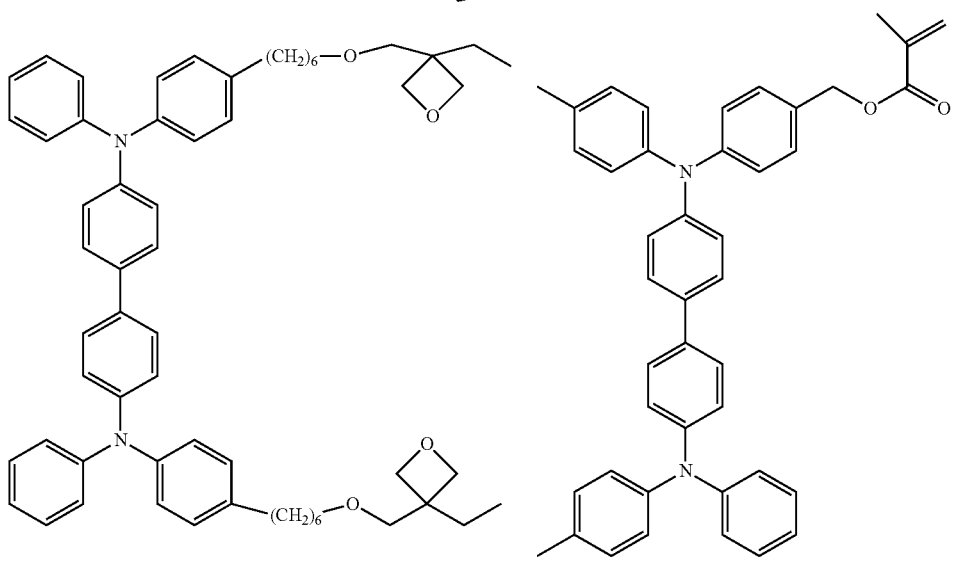

-continued
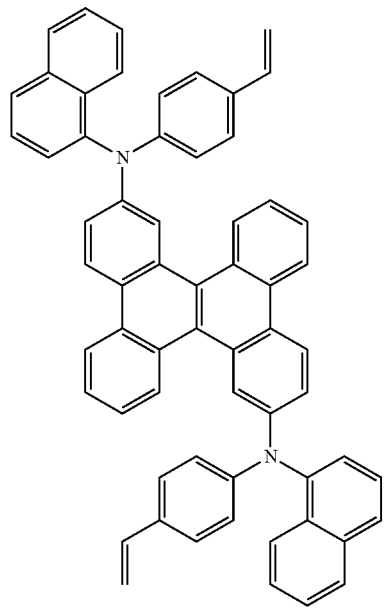
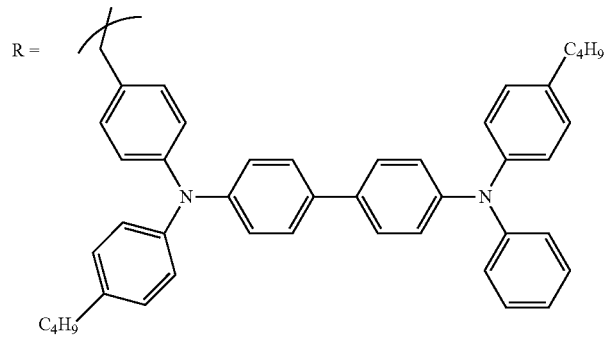
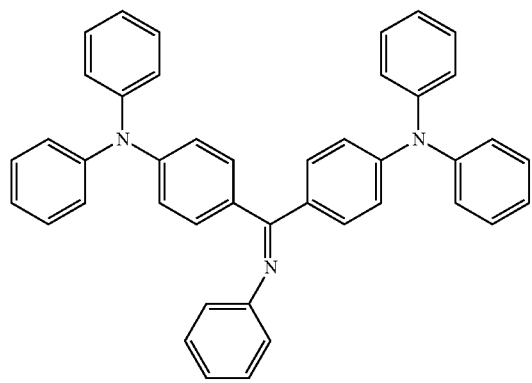
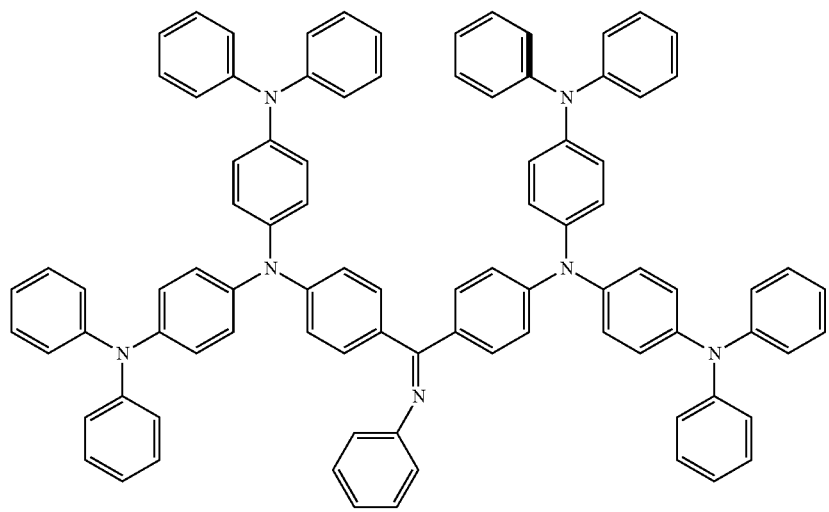

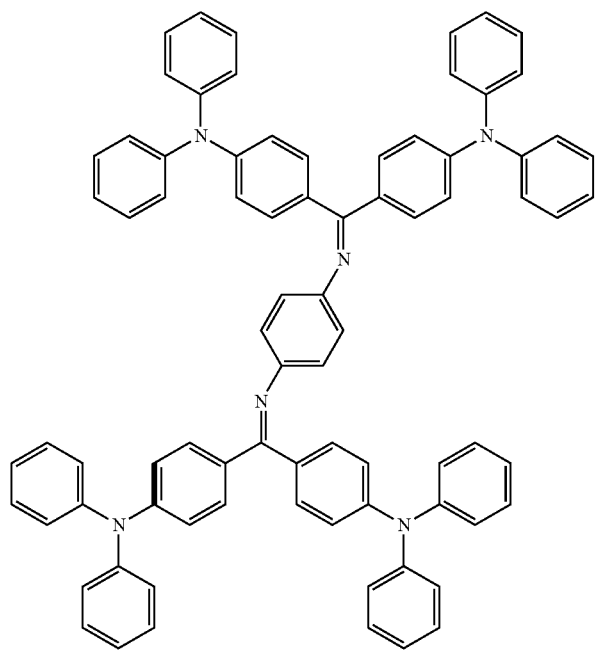
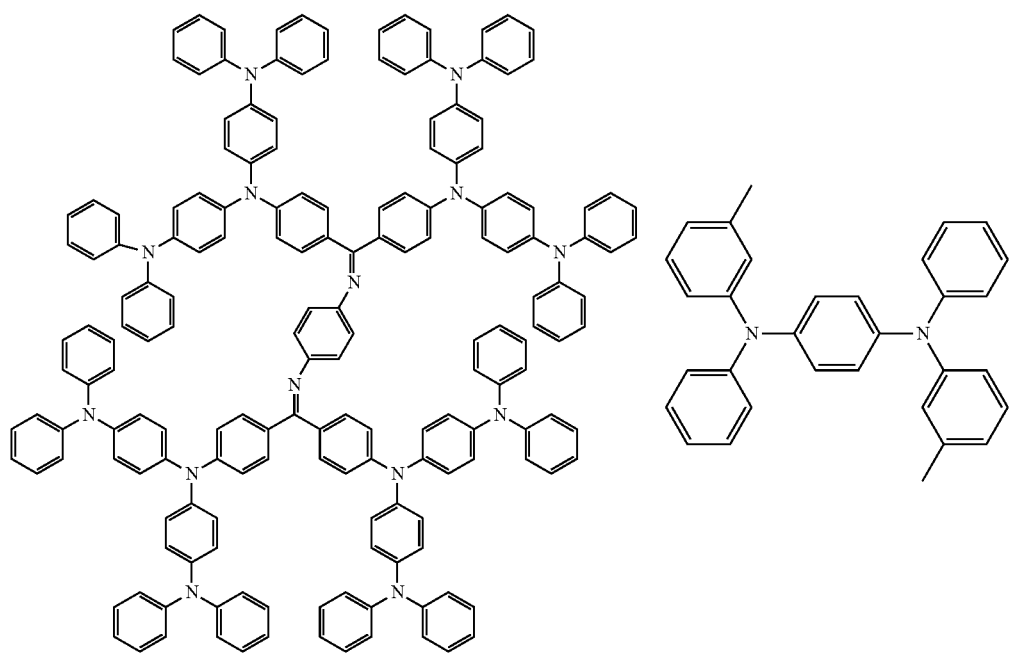

Preferred examples of a compound that may be used as the electron barrier material are shown below.
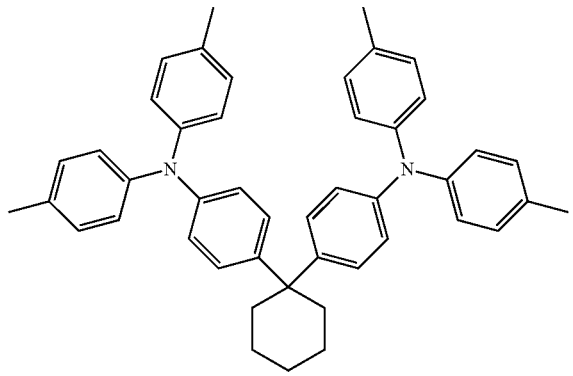
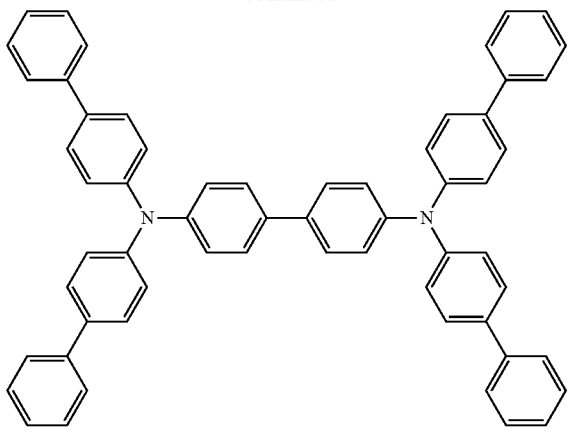
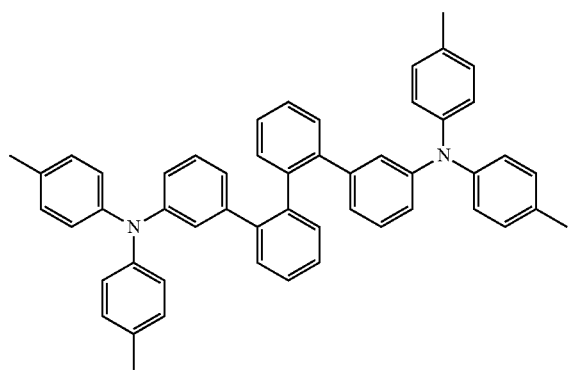
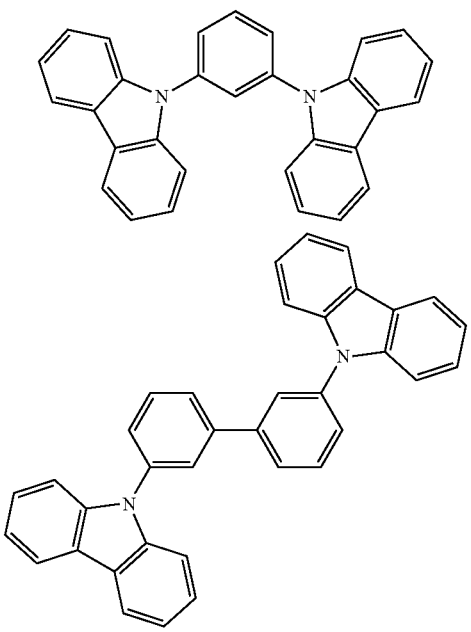
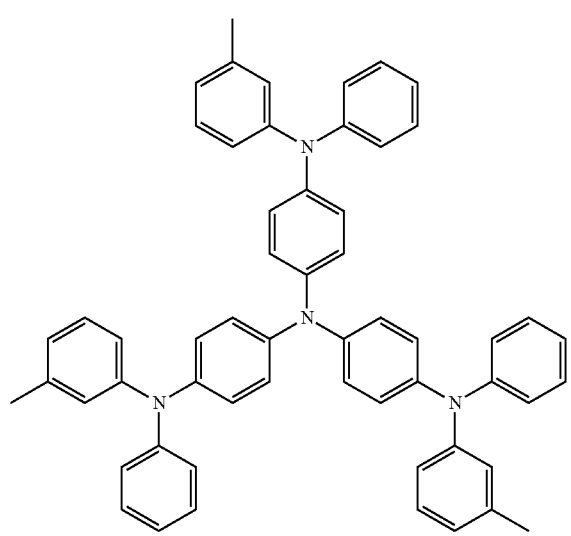
Preferred examples of a compound that may be used as the hole barrier material are shown below.
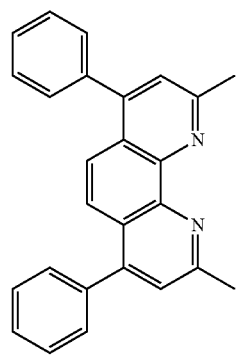

93
-continued
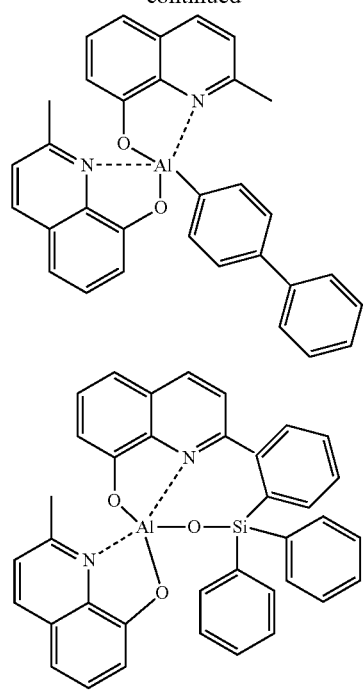
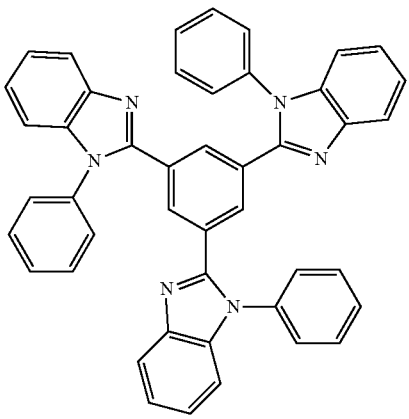
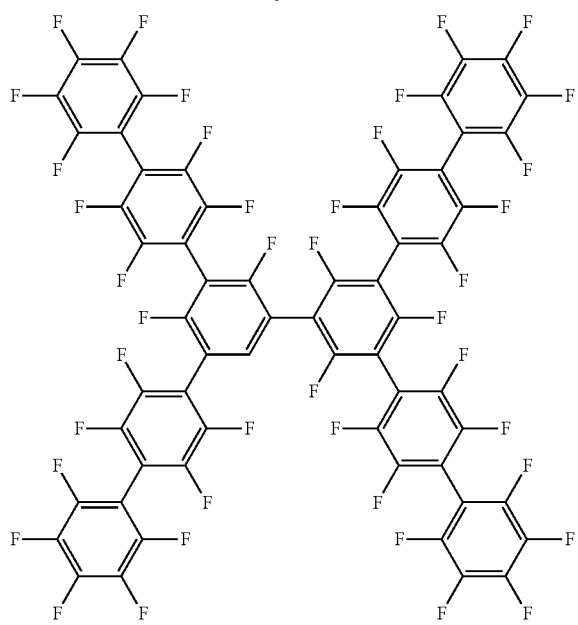
94
-continued
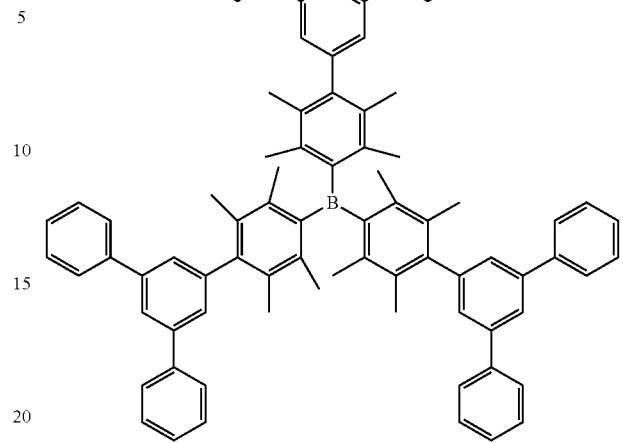
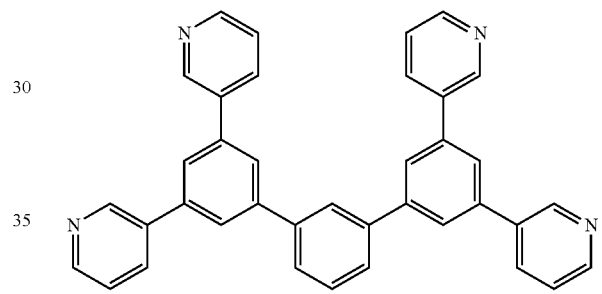
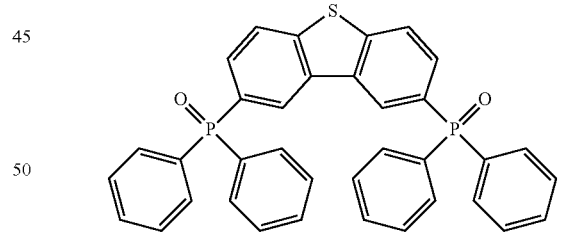
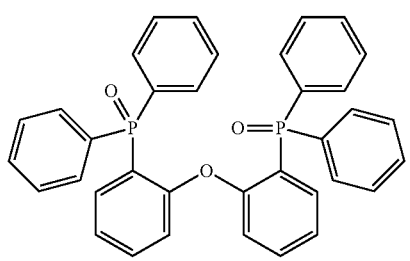

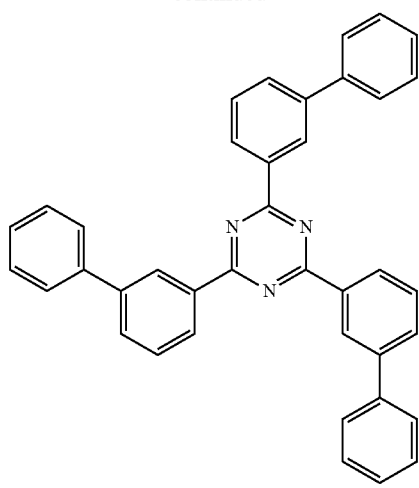
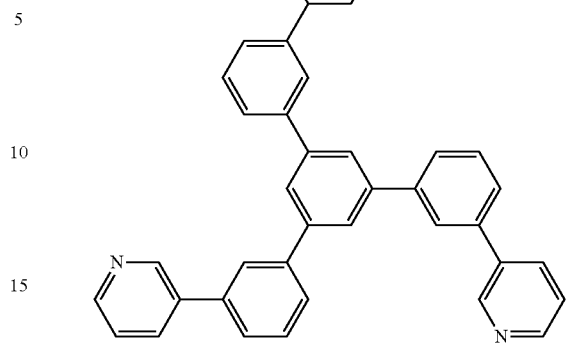
Preferred examples of a compound that may be used as the electron transporting material are shown below.
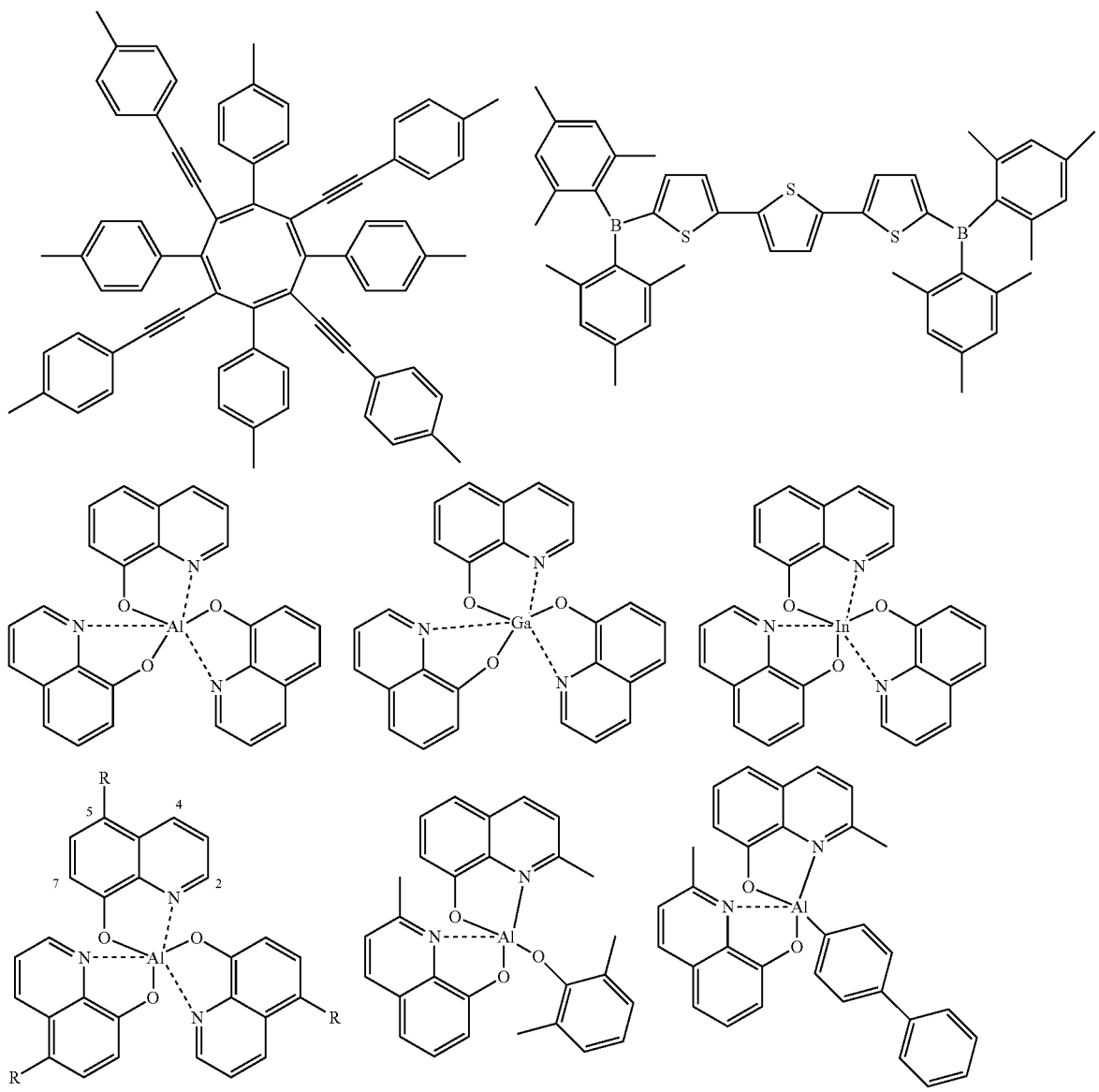

97 98
-continued
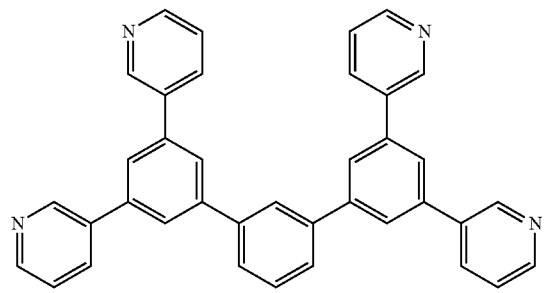 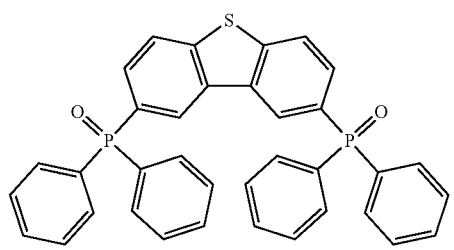
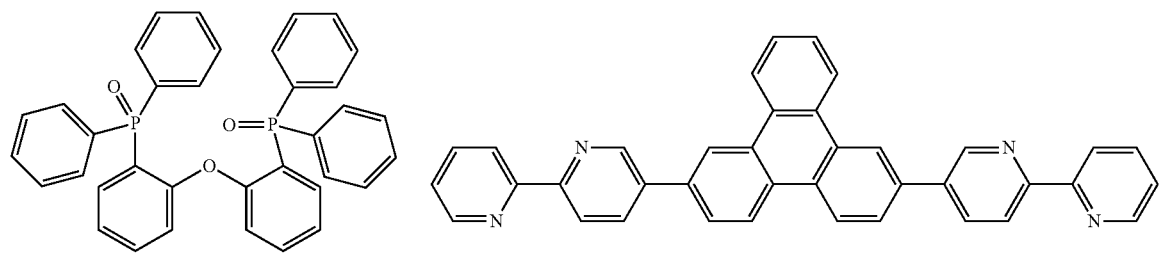
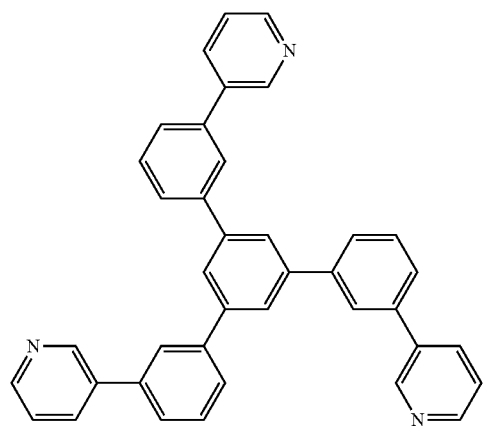 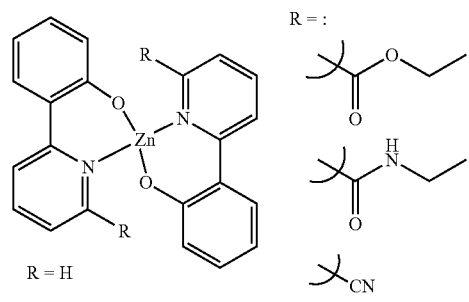
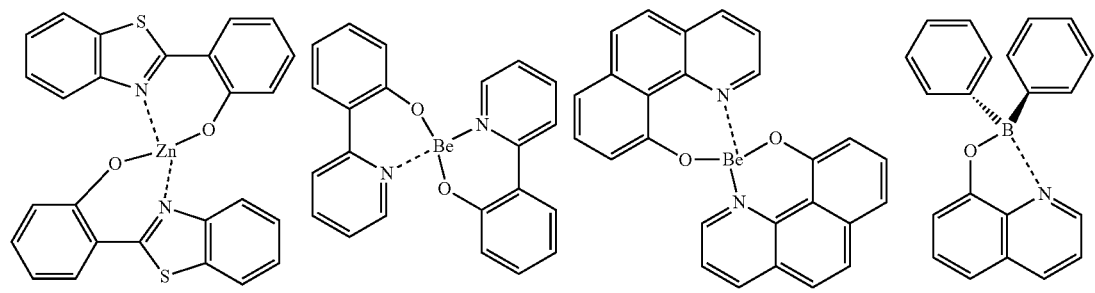

-continued
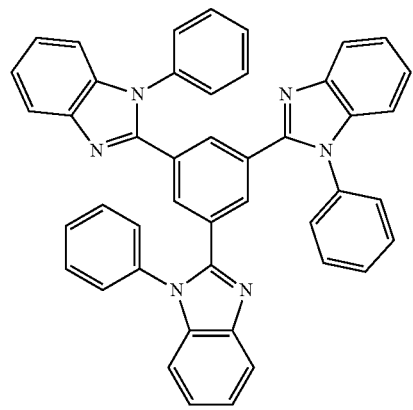
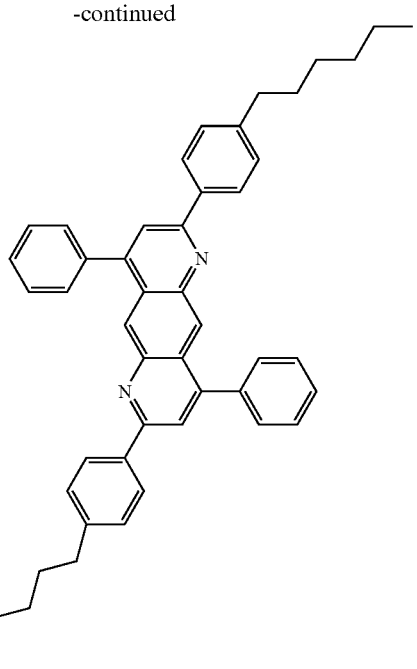
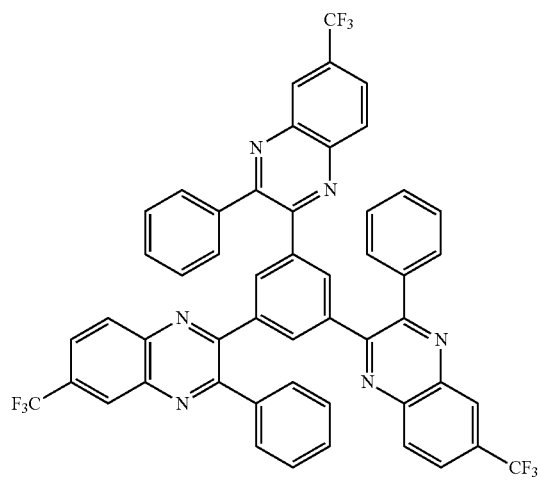
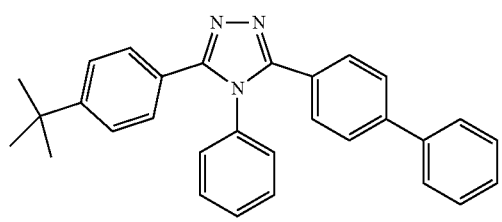
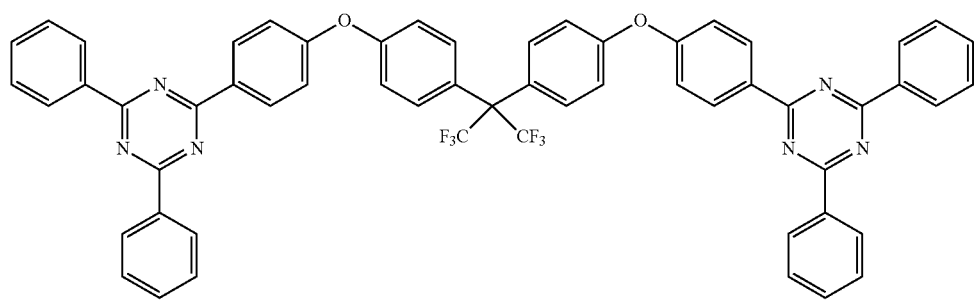

-continued
101
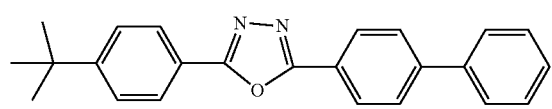
102
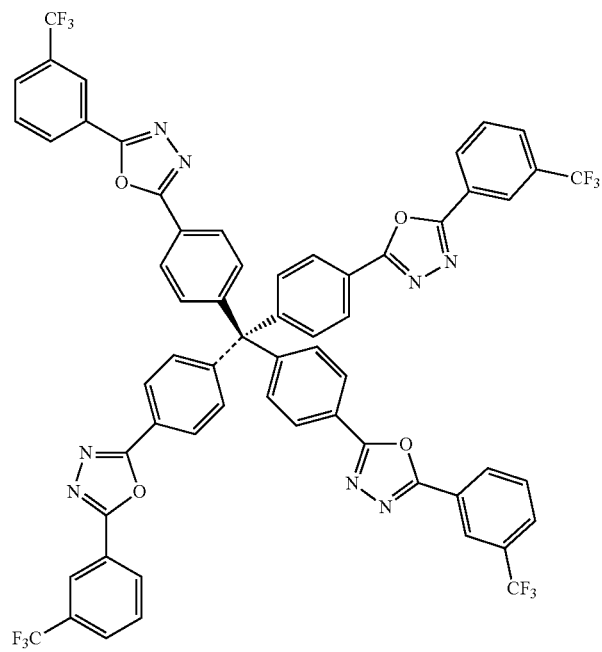
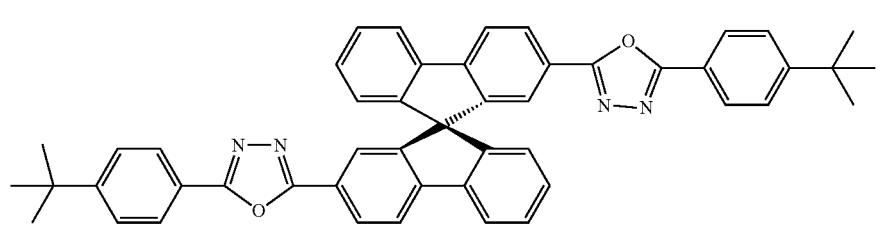
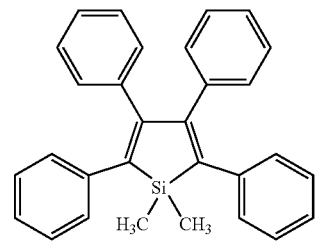
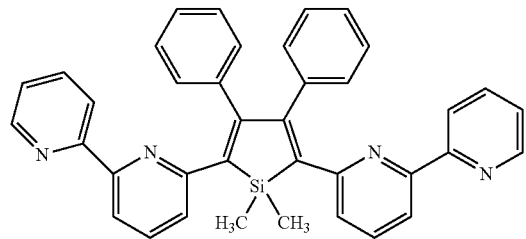
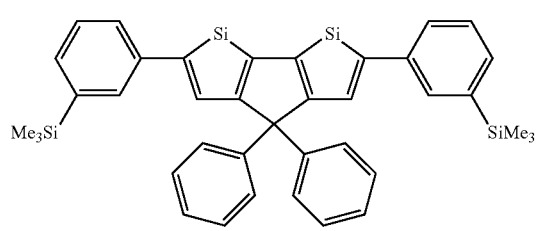
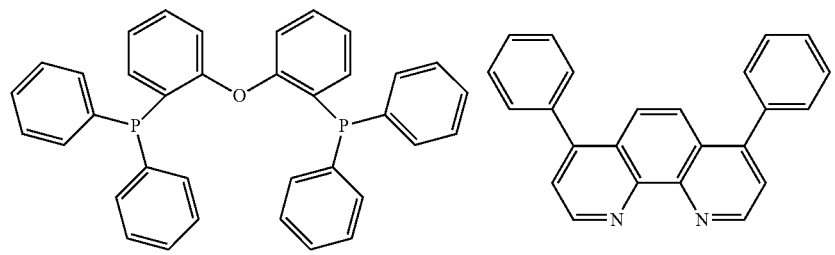

Preferred examples of a compound that may be used as the electron injection material are shown below.

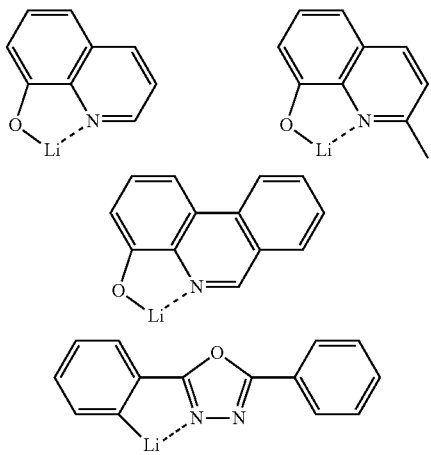

Preferred examples of a compound as a material that may be added are shown below. For example, the compound may be added as a stabilizing material.

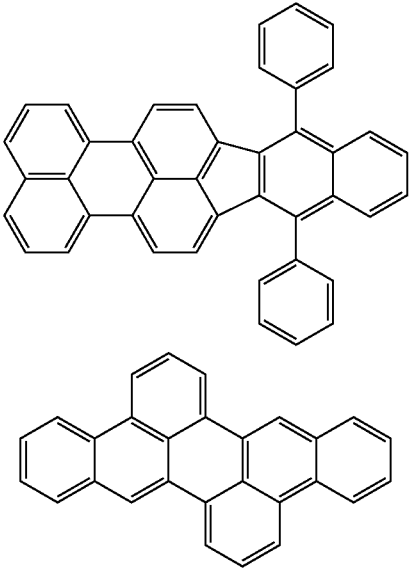

The organic electroluminescent device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetimes may be distinguished between the fluorescent light and the delayed fluorescent light.

The phosphorescent light may substantially not be observed with a normal organic compound, such as the compound of the invention, at room temperature since the excited triplet energy is unstable, and is immediately deactivated due to the large kinetic constant of thermal deactivation and the small kinetic constant of light emission. The excited triplet energy of the normal organic compound may be measured by observing light emission under an extremely low temperature condition.

The organic electroluminescent device of the invention may be applied to any of a single device, a structure with plural devices disposed in an array, and a structure having anodes and cathodes disposed in an X-Y matrix. According to the invention, an organic light-emitting device that is largely improved in light emission efficiency may be obtained by adding the compound represented by the general formula (1) in the light-emitting layer. The organic light-emitting device, such as the organic electroluminescent device, of the invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

EXAMPLES

The features of the invention will be described more specifically with reference to synthesis examples and working examples below. The materials, processes, procedures, and the like shown below may be appropriately modified unless they deviate from the substance of the invention. Accordingly, the scope of the invention is not construed as being limited to the specific examples shown below. The ultraviolet ray absorption spectrum was measured with LAMBDA 950-PKA (produced by Perkin-Elmer Corporation), the light emission spectrum was measured with Fluoromax-4 (produced by Horiba Jobin Yvon SAS), and the transient decay curve was measured with Quantaurus-tau (produced by Hlamamatsu Photonics K.K.). In the working examples, fluorescent light that had a light emission lifetime of 0.05 μs or more was determined as delayed fluorescent light.

Synthesis Example 1

Synthesis of Compound 291

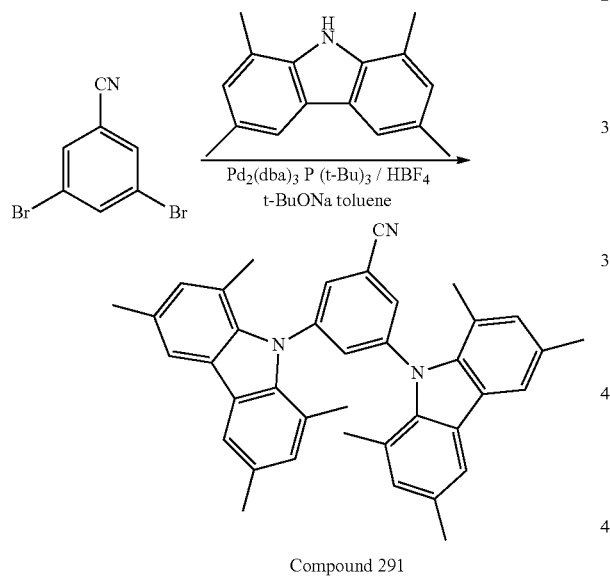

Compound 291

1,3,6,8-tetramethyl-9H-carbazole (1.07 g, 4.80 mmol), 3,5-dibromobenzonitrile (0.522 g, 2.00 mmol), sodium tert-butoxide (0.768 g, 8.00 mmol), tris (dibenzylideneacetone) dipalladium (O) (92.8 mg, 0.101 mmol) and tetrafluoroborate tri-tert-butylphosphine (0.220 g, 0.758 mmol) were added to a 100 mL three-neck flask having been substituted with nitrogen. The mixture was added with 35 mL of dehydrated toluene and stirred under heating at 95° C. for 12 hours. After the mixture was returned to room temperature, the mixture was added with chloroform and stirred. Then, the solution was rinsed with saturated saline. After the rinsing, the solution was added with anhydrous magnesium sulfate and dried. After the drying, the mixture was subjected to suction filtration for concentration, so that filtrate was obtained. The obtained filtrate was purified by silica gel column chromatography with hexane:chloroform (=2:1) as a developing solvent. The white solid matter obtained by concentrating the obtained fraction was stirred under heating by hexane and then filtered. The solid matter recovered by filtration was recrystallized with toluene, so that the white crystals of the target material were obtained in a yield amount of 470 mg and a yield of 45.0%.

$^1$H-NMR (500 MHz, CDCl$_3$, δ): 8.07 (d, J=2.0 Hz, 2H), 7.63 (s, 4H), 7.07 (t, J=2.0 Hz, 1H), 6.88 (s, 4H), 2.42 (s, 12H), 1.98 (s, 12H)

ASAP mass spectrum analysis:

Theoretical value: 545.7

Observed value: 545.7

Synthesis Example 2

Synthesis of Compound 241

First, 2,6-difluoro-4-(1,3,6,8-tetramethyl-9H-carbazole-9-il)benzonitrile, which was an intermediate, was synthesized by the following reaction.

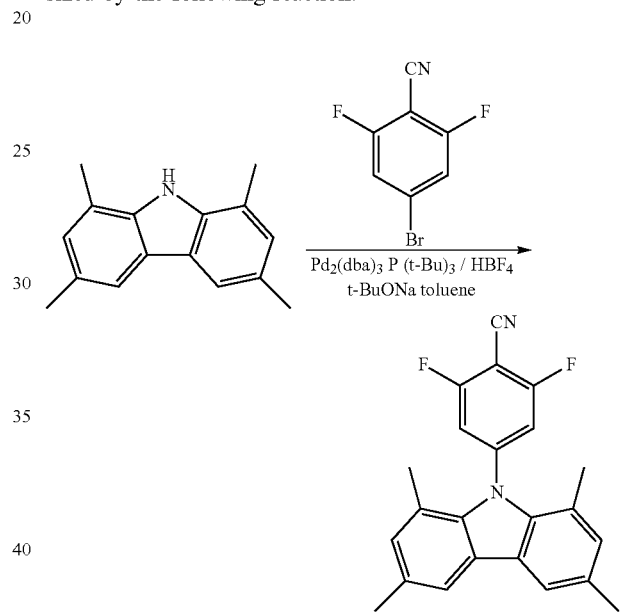

1,3,6,8-tetramethyl-9H-carbazole (1.20 g, 5.40 mmol), 4-bromo-2,6-difluorobenzonitrile (1.00 g, 4.59 mmol), sodium tert-butoxide (0.882 g, 9.18 mmol), tris(dibenzylideneacetone) dipalladium (O) (0.210 g, 0.230 mmol) and tetrafluoroborate tri-tert-butylphosphine (0.267 g, 0.920 mmol) were added to a 100 mL three-neck flask having been substituted with nitrogen. The mixture was added with 50 mL of dehydrated toluene and stirred under heating at 90° C. for 12 hours. After the stirring, the mixture was returned to the room temperature, added with chloroform and stirred. After the stirring, the mixture was rinsed with saturated saline. After the rinsing, the mixture was added with anhydrous magnesium sulfate and dried. Then, the mixture was subjected to suction filtration for concentration, so that filtrate was obtained. The obtained filtrate was purified by silica gel column chromatography with hexane:chloroform (=7:3) as a developing solvent. The obtained fraction was concentrated, so that white solid matter, which was 2,6-difluoro-4-(1,3,6,8-tetramethyl-9H-carbazole-9-il)benzonitrile, was obtained in a yield amount of 940 mg and a yield of 56.8%.

$^1$H-NMR (500 MHz, CDCl$_3$, δ): 7.71 (s, 2H), 7.18 (d, J=8.0 Hz, 2H), 6.94 (2, 2H), 2.47 (s, 6H), 1.96 (s, 6H)

ASAP mass spectrum analysis:

Theoretical value: 360.4

Observed value: 360.4

Subsequently, the compound 241 was synthesized by the following reaction.

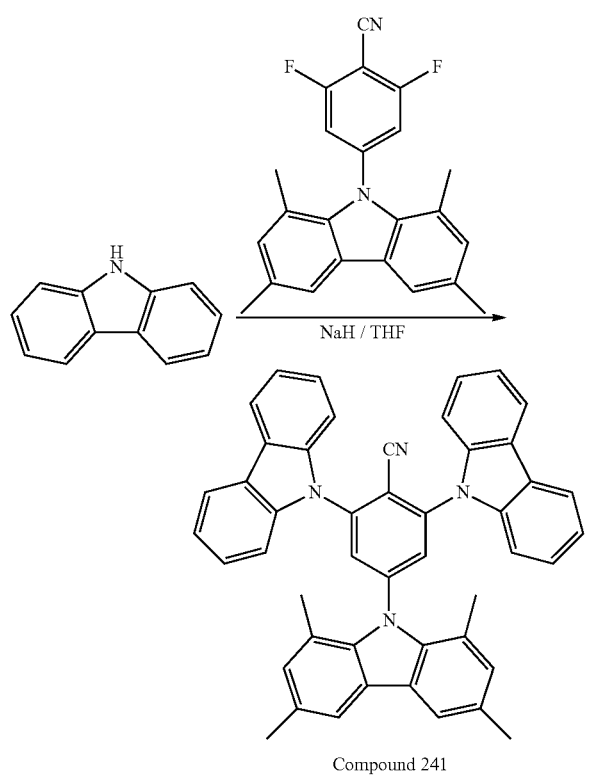

Compound 241

Sodium hydride (0.42 g, 10.4 mmol), 9H-carbazole (1.30 g, 7.81 mmol) and 50 mL of dehydrated tetrahydrofuran were added to a 100 mL three-neck flask having been substituted with nitrogen, and followed by stirring at room temperature for 1 hour. After the stirring, the mixture was added with 2,6-difluoro-4-(1,3,6,8-tetramethyl-9H-carbazole-9-il)benzonitrile (0.930 g, 2.60 mmol) under a nitrogen stream, and was stirred at room temperature for 12 hours. After the stirring, the mixture was added with chloroform and stirred. Then, the solution was rinsed with saturated saline. After the rinsing, the solution was added with anhydrous magnesium sulfate and dried. After the drying, the mixture was subjected to suction filtration, so that filtrate was obtained. The solid matter obtained by concentrating the obtained filtrate was added to methanol, stirred under heating and subjected to suction filtration, so that the solid matter was recovered. The recovered solid matter was recrystallized with ethyl acetate, so that white solid matter of the target material was obtained in a yield amount of 1.20 g and a yield of 70.5%.

$^1$H-NMR (500 MHz, CDCl$_3$, δ): 8.15 (d, J=7.5 Hz, 4H), 7.87 (s, 2H), 7.69 (s, 2H), 7.51 (t, J=8.0 Hz, 4H), 7.37 (t, J=7.0 Hz, 4H), 7.31 (d, j=8.0 Hz, 4H), 6.99 (s, 2H), 2.46 (s, 6H), 2.29 (s, 6H)

ASAP mass spectrum analysis:

Theoretical value: 654.8

Observed value: 654.8

Synthesis Example 3

First, 4-bromo-2,6-di(9H-carbazole-9-il)benzonitrile, which was an intermediate, was synthesized by the following reaction.

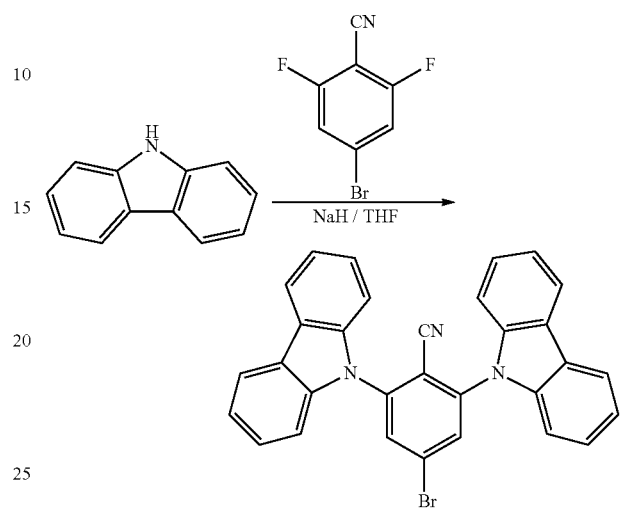

60% sodium hydride (0.275 g, 6.88 mmol), 40 mL of dehydrated tetrahydrofuran and 9H-carbazole (0.960 g, 5.73 mmol) were added to a 100 mL three-neck flask having been substituted with nitrogen, and followed by stirring at room temperature for 1 hour. While the mixture was cooled in an ice bath, the mixture was added with 4-bromo-2,6-difluorobenzonitrile (0.500 g, 2.29 mmol) under a nitrogen stream, and stirred for one night. After the stirring, the mixture was added with chloroform and water, stirred and rinsed with saturated saline. After the rinsing, the mixture was added with anhydrous magnesium sulfate and dried. Then, the mixture was subjected to suction filtration for concentration, so that solid matter was obtained. The obtained solid matter was purified by silica gel column chromatography with hexane:chloroform (=1:1) as a developing solvent. The obtained fraction was concentrated, so that the light yellow solid matter, which was 4-bromo-2,6-di(9H-carbazole-9-il)benzonitrile, was obtained in a yield amount of 310 mg and a yield of 26.5%.

$^1$H-NMR (500 MHz, CDCl$_3$, δ): 8.16 (d, J=7.5 Hz, 4H), 7.94 (s, 2H), 7.52 (td, J=9.4 Hz, J=1.2 Hz, 4H), 7.38 (td, J=8.0 Hz, J=1.0 Hz, 8H)

ASAP mass spectrum analysis:

Theoretical value: 512.4

Observed value: 512.4

Subsequently, a compound 135 was synthesized by the following reaction.

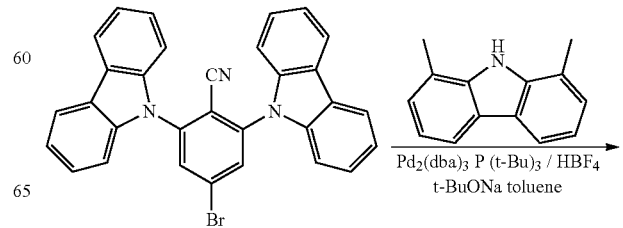

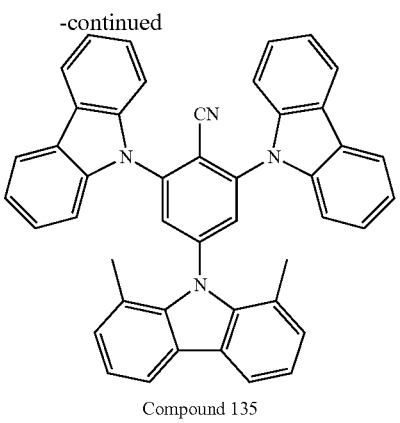

Compound 135

4-bromo-2,6-di(9H-carbazole-9-il)benzonitrile (0.300 g, 0.585 mmol), 1,8-dimethyl-9H-carbazole (0.125 g, 0.643 mmol), sodium tert-butoxide (0.170 g, 1.76 mmol), tris (dibenzylideneacetone) dipalladium (O) (54.0 mg, 0.0585 mmol) and tetrafluoroborate tri-tert-butylphosphine (17.0 g, 0.0585 mmol) were added to a 100 mL three-neck flask having been substituted with nitrogen. The mixture was added with 50 mL of dehydrated toluene and stirred under heating at 120° C. for 12 hours. After the stirring, the mixture was returned to room temperature, added with chloroform and water, and stirred. After the stirring, the mixture was rinsed with saturated saline. After the rinsing, the mixture was added with anhydrous magnesium sulfate and dried. Then, the mixture was subjected to suction filtration for concentration, so that filtrate was obtained. The obtained filtrate was purified by silica gel column chromatography with hexane:chloroform (=6:4) as a developing solvent. The obtained fraction was concentrated, so that the white solid matter of the target material was obtained in a yield amount of 0.170 mg and a yield of 46.3%.

$^1$H NMR (500 MHz, CDCl$_3$, δ): 8.15 (d, J=7.6 Hz, 4H), 7.95 (dd, 2.0 Hz, 2H), 7.93 (s, 2H), 7.52 (td, J=7.7 Hz, J=1.2 Hz, 4H), 7.39-7.33 (m, 8H), 7.22-7.17 (m, 4H), 2.35 (s, 6H)

ASAP mass spectrum analysis:
Theoretical value: 626.8
Observed value: 626.8

Example 1

Preparation and Evaluation of Organic Photoluminescent Device Using Compound 291

A toluene solution of the compound 291 (concentration: $1 \times 10^{-5}$ mol/L) was prepared in a glove box under an Ar atmosphere.

Figure 2:
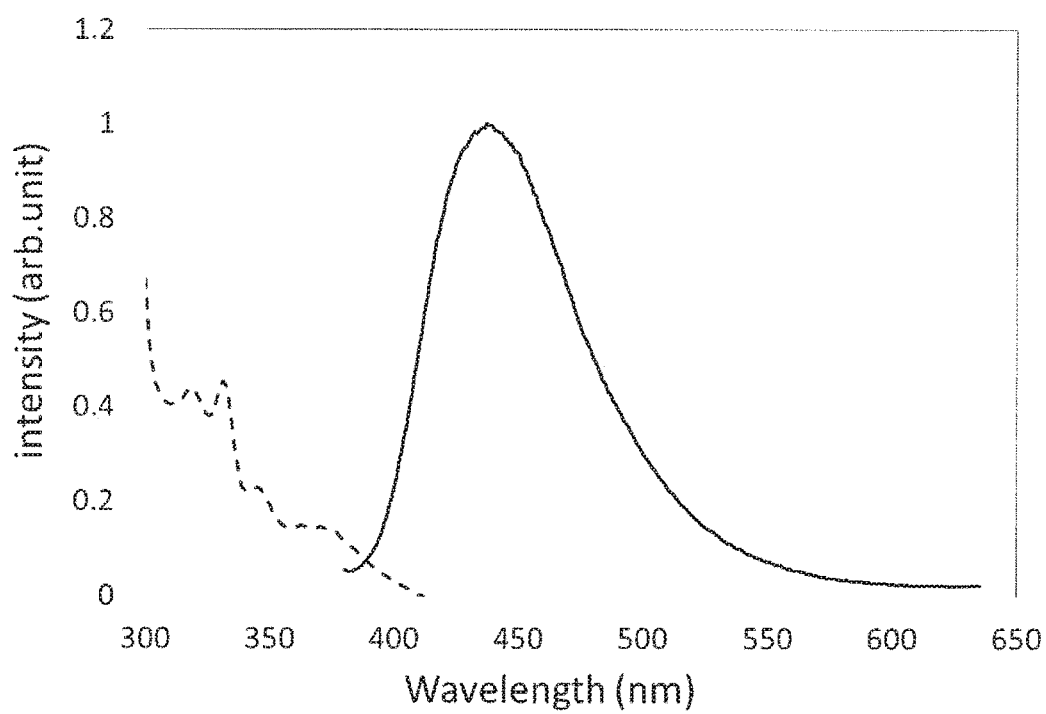
FIG. 2 is the light emission spectrum and the light absorption spectrum of the toluene solution of the compound 291 in Example 1.
Figure 3:
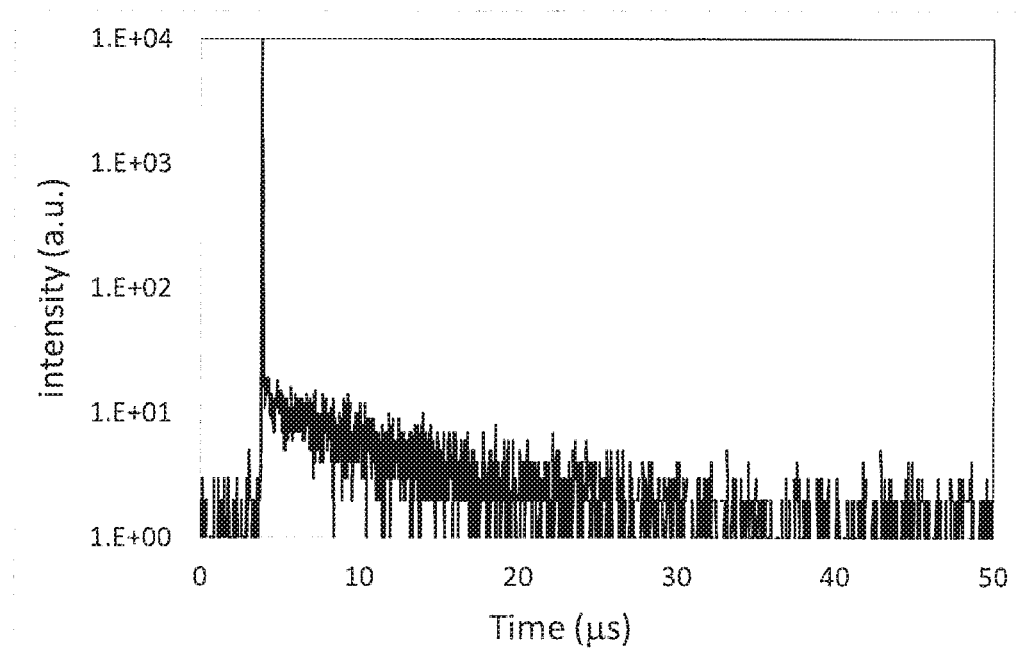
FIG. 3 is the transient decay curve of the toluene solution of the compound 291 in Example 1.

For the toluene solution of the compound 291, the light emission spectrum and the light absorption spectrum measured with excitation light of 337 nm are shown in FIG. 2, and the transient decay curve measured with excitation light of 280 nm after bubbling with argon is shown in FIG. 3. In FIG. 2, the solid line shows the light emission spectrum, and the broken line shows the light absorption spectrum. The photoluminescence quantum efficiency was 4.60% for the toluene solution before bubbling, and 10.4% for the toluene solution after bubbling with argon. A fluorescent light component rapidly attenuated and a delayed fluorescent light component slowly attenuated were confirmed from FIG. 3, in which the light emission lifetime of the fluorescent light component rapidly attenuated was 12.0 ns (nanosecond), and the light emission lifetime of the delayed fluorescent light component was 8.72 μs.

It was confirmed from the results that the compound 291 was a compound capable of emitting delayed fluorescent light and had a high light emission efficiency.

Comparative Example 1

Preparation and Evaluation of Organic Photoluminescent Device Using Comparative Compound 1

A toluene solution (concentration: $1 \times 10^{-5}$ mol/L) was prepared under the same condition as in Example 1 except that the comparative compound 1 shown by the following formula was used instead of the compound 291.

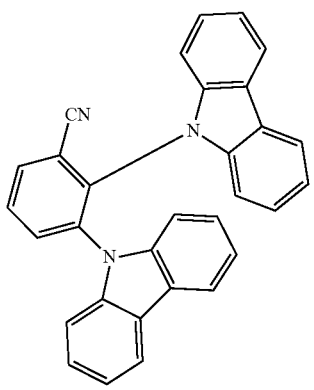

Comparative Compound 1

Figure 4:
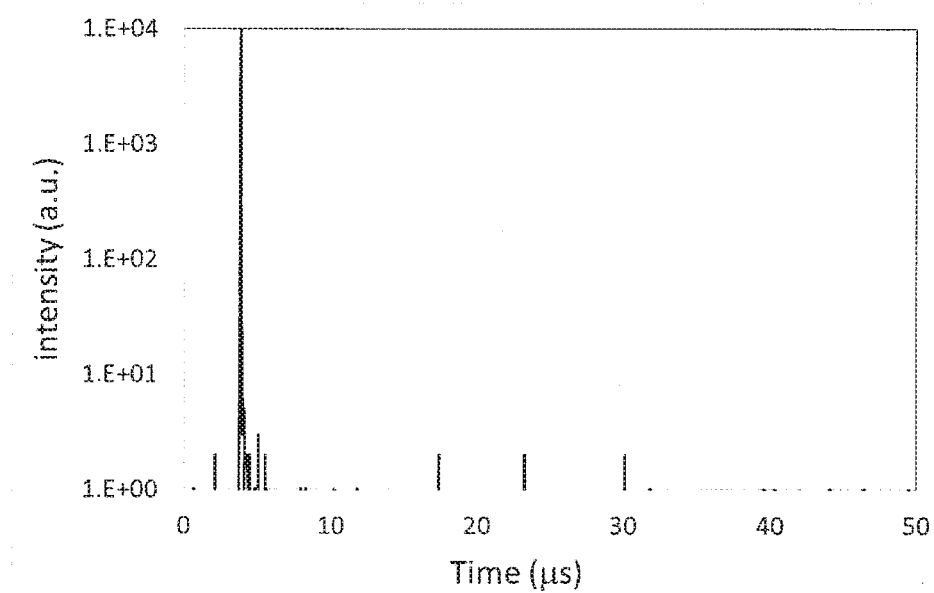
FIG. 4 is the transient decay curve of the toluene solution of the comparative compound 1.

For the toluene solution of the comparative compound 1, the transient decay curve measured with excitation light of 280 nm after bubbling with argon is shown in FIG. 4. The photoluminescence quantum efficiency was 8.60% for the toluene solution before bubbling, and 10.7% for the toluene solution after bubbling with argon. A delayed fluorescent light component was not confirmed from FIG. 4, and only the fluorescent light component rapidly attenuated (light emission lifetime: 4.10 ns) was observed.

Example 2

Preparation and Evaluation of Organic Photoluminescent Device Using Compound 241

The compound 241 was used instead of the compound 291, and a toluene solution (concentration: $1 \times 10^{-5}$ mol/L) was prepared under the similar condition to Example 1.

Figure 5:
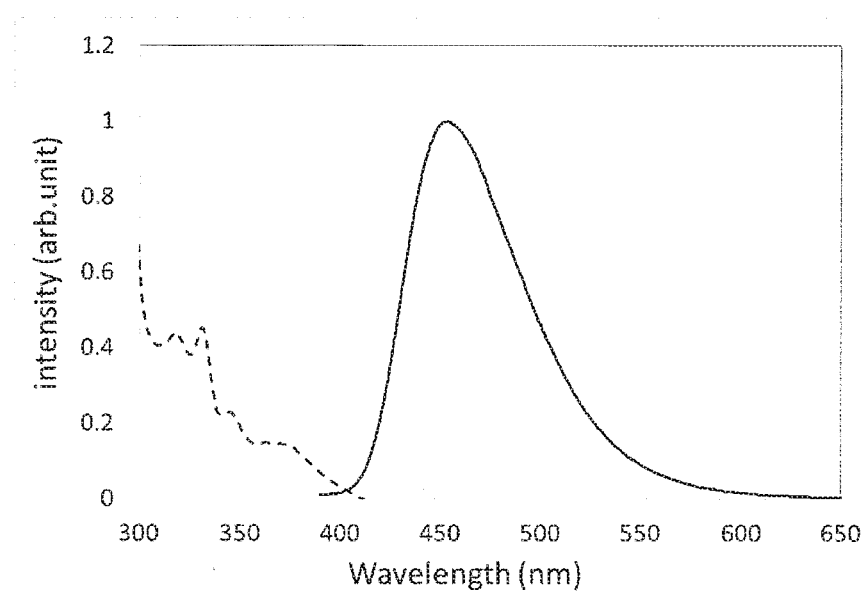
FIG. 5 is the light emission spectrum and the light absorption spectrum of the toluene solution of the compound 241 in Example 2.
Figure 6:
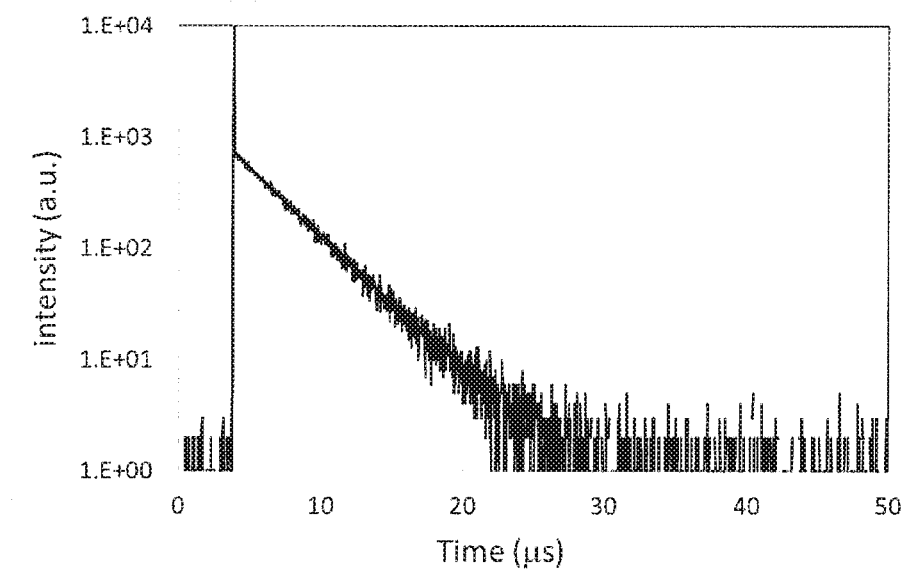
FIG. 6 is the transient decay curve of the toluene solution of the compound 241 in Example 2.

For the toluene solution of the compound 241, the light emission spectrum and the light absorption spectrum measured with excitation light of 337 nm are shown in FIG. 5, and the transient decay curve measured with excitation light of 280 nm after bubbling with argon is shown in FIG. 6. In FIG. 5, the solid line shows the light emission spectrum, and the broken line shows the light absorption spectrum. The photoluminescence quantum efficiency was 10.3% for the toluene solution before bubbling, and 100% for the toluene solution after bubbling with argon. A fluorescent light component rapidly attenuated and a delayed fluorescent light component slowly attenuated were confirmed from FIG. 6, in which the light emission lifetime of the fluorescent light component rapidly attenuated was 15.4 ns, and the light emission lifetime of the delayed fluorescent light component was 3.54 μs.

It was confirmed from the results that the compound 241 was a compound capable of emitting delayed fluorescent light and had a high light emission efficiency.

Example 3

Preparation and Evaluation of Organic Photoluminescent Device Using Compound 135

The compound 135 was used instead of the compound 291, and a toluene solution (concentration: $1 \times 10^{-5}$ mol/L) was prepared under the similar condition to Example 1.

Figure 7:
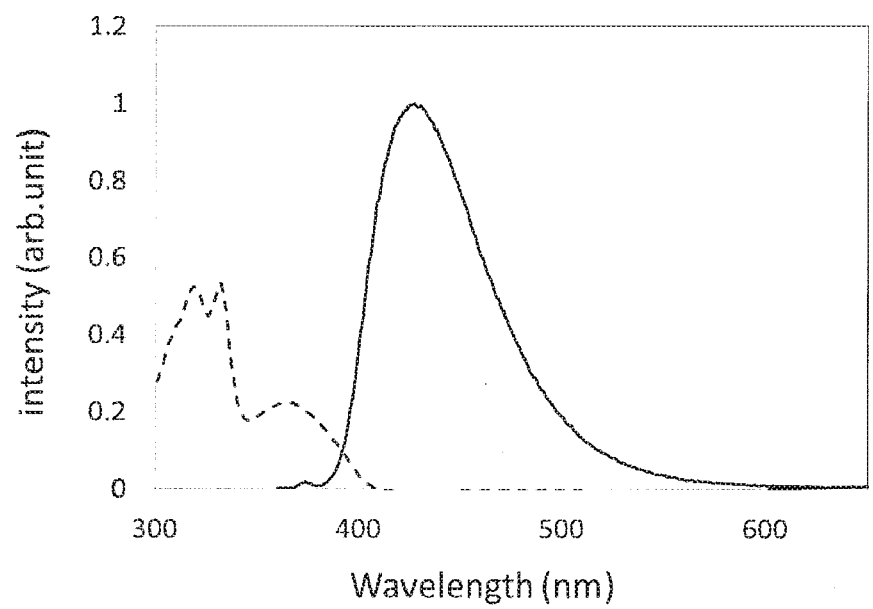
FIG. 7 is the light emission spectrum and the light absorption spectrum of the toluene solution of the compound 135 in Example 3.
Figure 8:
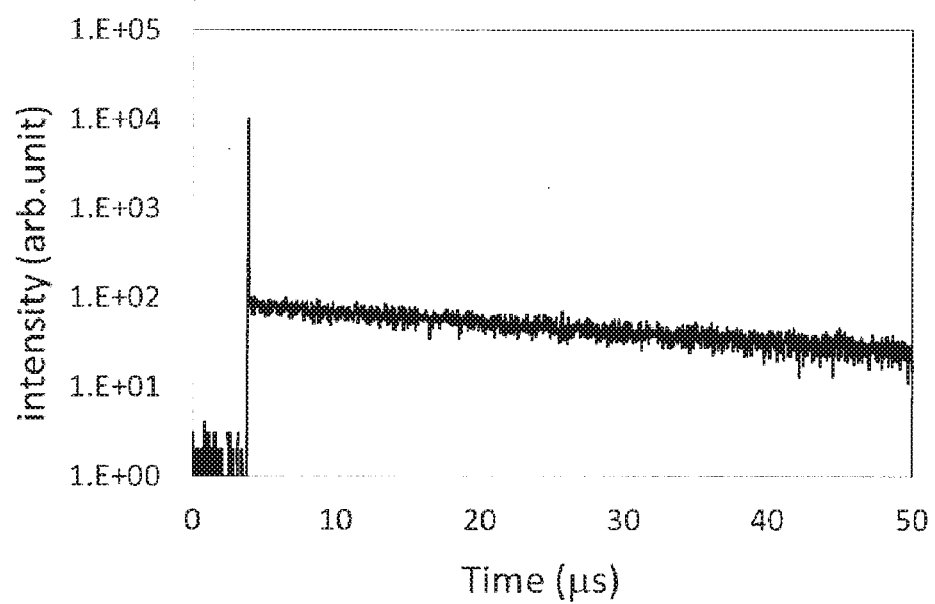
FIG. 8 is the transient decay curve of the toluene solution of the compound 135 in Example 3.

For the toluene solution of the compound 135, the light emission spectrum and the light absorption spectrum measured with excitation light of 337 nm are shown in FIG. 7, and the transient decay curve measured with excitation light of 340 nm after bubbling with argon is shown in FIG. 8. In FIG. 7, the solid line shows the light emission spectrum, and the broken line shows the light absorption spectrum. The photoluminescence quantum efficiency was 7.6% for the toluene solution before bubbling, and 100% for the toluene solution after bubbling with argon. A fluorescent light component rapidly attenuated and a delayed fluorescent light component slowly attenuated were confirmed from FIG. 8, in which the light emission lifetime of the fluorescent light component rapidly attenuated was 6.5 ns, and the light emission lifetime of the delayed fluorescent light component was 37 μs.

It was confirmed from the results that the compound 135 was a compound capable of emitting delayed fluorescent light and had a high light emission efficiency.

Comparative Example 2

Preparation and Evaluation of Organic Photoluminescent Device Using Comparative Compound 2

A toluene solution (concentration: $1 \times 10^{-5}$ mol/L) was prepared under the same condition as in Example 1 except that the comparative compound 2 shown by the following formula was used instead of the compound 291.

Comparative Compound 2

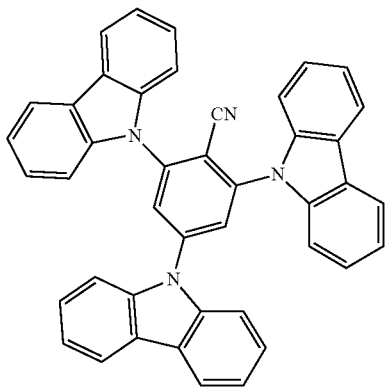

Figure 9:
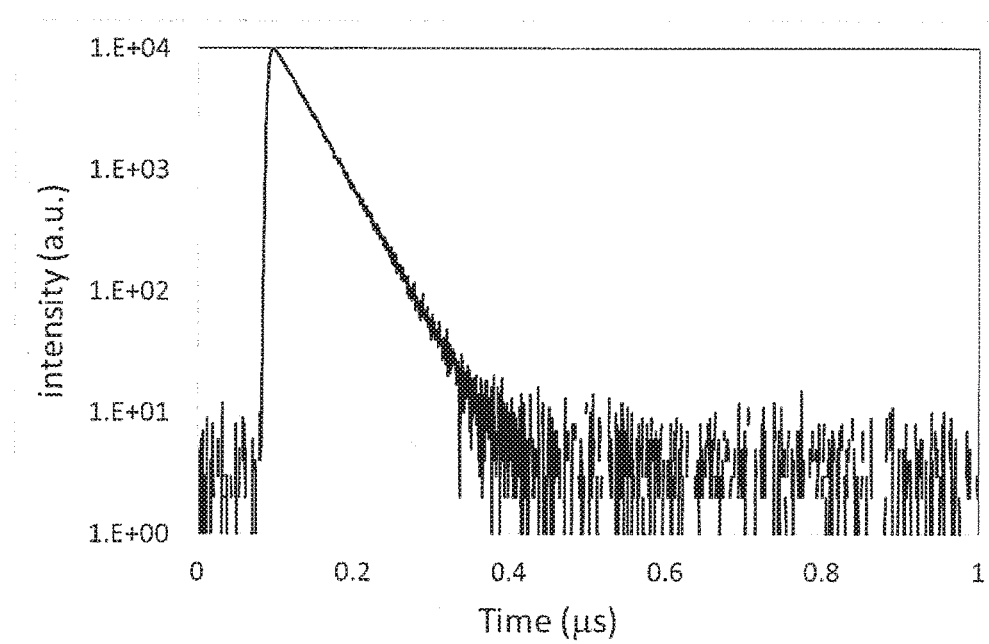
FIG. 9 is the transient decay curve of the toluene solution of the comparative compound 2.

For the toluene solution of the comparative compound 2, the transient decay curve measured with excitation light of 280 nm after bubbling with argon is shown in FIG. 9. The photoluminescence quantum efficiency was 14.4% for the toluene solution before bubbling, and 18.9% for the toluene solution after bubbling with argon. A delayed fluorescent light component was not confirmed from FIG. 9, and only the fluorescent light component rapidly attenuated (light emission lifetime: 3.75 ns) was observed.

INDUSTRIAL APPLICABILITY

The compound of the invention is useful as a light-emitting material. Accordingly, the compound of the invention may be effectively used as a light-emitting material of an organic light-emitting device, such as an organic electroluminescent device. The compound of the invention includes a compound that emits delayed fluorescent light, and thus is capable of providing an organic light-emitting device having a high light emission efficiency. Accordingly, the invention has high industrial applicability.

REFERENCE SIGNS LIST

1 substrate
2 anode
3 hole injection layer
4 hole transporting layer
5 light-emitting layer
6 electron transporting layer
7 cathode

The invention claimed is:
1. A compound having a structure represented by the following general formula (1):

General Formula (1)

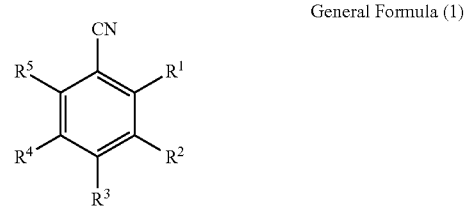

wherein:
one or more of $R^1$, $R^2$, $R^3$, $R^4$, and $R^5$ each independently represent a 9-carbazolyl group having a substituent at at least one of 1-position and 8-position, a 10-phenoxazyl group having a substituent at at least one of 1-position and 9-position or a 10-phenothiazyl group having a substituent at at least one of 1-position and 9-position, the balance thereof represents a hydrogen atom or a substituent, provided that the substituent excludes a 9-carbazolyl group having a substituent at at least one of 1-position and 8-position, a 10-phenoxazyl group having a substituent at at least one of 1-position and 9-position or a 10-phenothiazyl group having a substituent at at least one of 1-position and 9-position;
two to four of $R^1$, $R^2$, $R^3$, $R^4$, and $R^5$ each independently represent a substituted or unsubstituted 9-carbozolyl group, a substituted or unsubstituted 10-phenoxazyl group or a substituted or unsubstituted 10-phenothiazyl group; and
$R^2$ and $R^4$ each independently represent a substituted or unsubstituted 9-carbazolyl group, a substituted or unsubstituted 10-phenoxazyl group or a substituted or unsubstituted 10-phenothiazyl group, and at least one of $R^1$, $R^3$ and $R^5$ is a hydrogen atom, or alternatively $R^2$ and $R^4$ are a hydrogen atom; and one or more of carbon atoms constituting ring skeletons of all of said respective 9-carbazolyl group, all of said respective 10-phenoxazyl group, and the 10-phenothiazyl group may be replaced by a nitrogen atom.

2. The compound according to claim 1, wherein the substituent represents a substituted or unsubstituted alkyl group, a substituted or unsubstituted alkoxy group, a substituted or unsubstituted thioalkoxy group, a substituted or unsubstituted aryl group, a substituted or unsubstituted heteroaryl group, a substituted or unsubstituted aryloxy group, a substituted or unsubstituted heteroaryloxy group, a substituted or unsubstituted thioaryloxy group, a substituted or unsubstituted thioheteroaryloxy group, a secondary amino group, a tertiary amino group, or a substituted or unsubstituted silyl group.

3. The compound according to claim 1, wherein $R^1$, $R^3$, and $R^5$ each independently represent a substituted or unsubstituted 9-carbazolyl group, a substituted or unsubstituted 10-phenoxazyl group or a substituted or unsubstituted 10-phenothiazyl group.

4. The compound according to claim 3, wherein $R^3$ represents a 9-carbazolyl group having a substituent at at least one of 1-position and 8-position, a 10-phenoxazyl group having a substituent at at least one of 1-position and 9-position or a 10-phenothiazyl group having a substituent at at least one of 1-position and 9-position.

5. The compound according to claim 4, wherein $R^1$ and $R^5$ each independently represent a 9-carbazolyl group unsubstituted at the 1-position and the 8-position, a 10-phenoxazyl group unsubstituted at the 1-position and the 9-position or a 10-phenothiazyl group unsubstituted at the 1-position and the 9-position.

6. The compound according to claim 1, wherein $R^2$ and $R^4$ each independently represent a substituted or unsubstituted 9-carbazolyl group, a substituted or unsubstituted 10-phenoxazyl group or a substituted or unsubstituted 10-phenothiazyl group.

7. The compound according to claim 6, wherein $R^2$ and $R^4$ each independently represent a 9-carbazolyl group having a substituent at at least one of 1-position and 8-position, a 10-phenoxazyl group having a substituent at at least one of 1-position and 9-position or a 10-phenothiazyl group having a substituent at at least one of 1-position and 9-position.

8. An organic light-emitting device containing a substrate having thereon a light-emitting layer containing the compound according to claim 1.

9. The organic light-emitting device according to claim 8, wherein the organic light-emitting device is an organic electroluminescent device.

10. The organic light-emitting device according to claim 8, wherein the light-emitting layer contains the compound and a host material.

11. The organic light-emitting device according to claim 8 which emits a delayed fluorescence.

* * * * *